(12) United States Patent
Park et al.

(10) Patent No.: US 9,567,594 B2
(45) Date of Patent: Feb. 14, 2017

(54) **SITE-SPECIFIC INCORPORATION OF PHOSPHOSERINE INTO PROTEINS IN *ESCHERICHIA COLI***

(71) Applicant: Yale University, New Haven, CT (US)

(72) Inventors: Hee-Sung Park, Daejeon (KR); Dieter Söll, Guilford, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 14/795,434

(22) Filed: Jul. 9, 2015

(65) Prior Publication Data

US 2015/0307912 A1 Oct. 29, 2015

Related U.S. Application Data

(63) Continuation of application No. 13/877,628, filed as application No. PCT/US2011/055414 on Oct. 7, 2011, now Pat. No. 9,090,928.

(60) Provisional application No. 61/470,332, filed on Mar. 31, 2011, provisional application No. 61/390,853, filed on Oct. 7, 2010.

(51) Int. Cl.

| | |
|---|---|
| *C12N 15/67* | (2006.01) |
| *C12P 21/02* | (2006.01) |
| *C12P 21/00* | (2006.01) |
| *C12N 9/00* | (2006.01) |
| *C07K 14/245* | (2006.01) |
| *C07K 14/435* | (2006.01) |

(52) U.S. Cl.
CPC ............ *C12N 15/67* (2013.01); *C07K 14/245* (2013.01); *C07K 14/435* (2013.01); *C12N 9/93* (2013.01); *C12P 21/00* (2013.01); *C12P 21/02* (2013.01); *C12Y 601/01027* (2013.01)

(58) Field of Classification Search
None
See application file for complete search history.

(56) References Cited

U.S. PATENT DOCUMENTS

| 6,503,729 B1 | 1/2003 | Bult |
| 7,723,069 B2 | 5/2010 | Söll |
| 2003/0082575 A1 | 5/2003 | Schultz |
| 2014/0154744 A1 | 6/2014 | Söll |

FOREIGN PATENT DOCUMENTS

| EP | 2246428 | 11/2010 | |
| JP | 2008061538 | 3/2008 | |
| WO | 0044906 | 8/2000 | |
| WO | WO 0044906 A2 * | 8/2000 | ........... C07K 14/245 |
| WO | 2006107813 | 10/2006 | |

OTHER PUBLICATIONS

Altschul et al., "Basic local alignment search tool", J. Mol. Biol., 215 (3):403-410 (1990).
Ambrogelly, et al., "Cys-tRNACys formation and cycteine biosynthesis in methanogenic archaea: two faces of the same problem?", Cell. Mol. LifeSci., 61:2437-45 (2004).
Arslan, et al., "Structurally modified firefly luciferase. Effects of amino acid subsitution at position 286", Journal of the American Chemical Sciety, 119 (45): 10877-10887 (1997).
Balch, et al., "Transport of coenzyrne M (2-mercaptoethanesulfonic acid) in Methanobacterium ruminantium", J. Bacteriol., 137:264 (1979).
Basurko, et al., Phosphoserine aminotransferase, the second step-catalyzing enzyme for serine biosynthesis\, IUBMB Life, 48:525-9 (1999).
Bentin, et al., "Photoreactive bicyclic amino acids as substrates for mutant *Escherichia coli* phenylalanyl-tRNA synthetases", J. Biol. Chem. 279:19839-45 (2004).
Bilokapic, et al., "The unusual methanogenic seryl-tRNA synthetase recognizes tRNASer species from all three kingdoms of life", Eur. Journ. Biochemistry, 271 (4):694-702 (2004).
Blight, et al., "Direct charging of tRNA(CUA) with pyrrolysine in vitro and in vivo", Nature, 431(7006):333-5 (2004).
Boyington, et al., "Crystal structure of formate dehydrogenase H: cataysis involving Mo, molybdopterin, selenosyteine, and an Fe4S4 cluster", Science, 275:1305-08 (1997).
Buchner, et al., "A method for increasing the yield of properly folded recombinant fusion proteins: single-chain immunotoxins from renaturation of bacterial inclusion bodies", Anal. Biochem., 205: 263-270 (1992).
Calendar and Berg, "Purification and physical characterization of tyrosyl ribonucleic acid synthetases from *Escherichia coli* and Bacillus subtilis", Biochemistry, 5(5):1681-90 (1966a).
Calendar and Berg, "The catalytic properties of tyrosyl ribonucleic acid synthetases from *Escherichia coli* and Bacillus subtilis", Biochemistry, 5 (5):1690-5 (1966b).

(Continued)

*Primary Examiner* — Mindy G Brown
(74) *Attorney, Agent, or Firm* — Pabst Patent Group LLP

(57) ABSTRACT

Nucleic acids encoding mutant elongation factor proteins (EF-Sep), phosphoseryl-tRNA synthetase (SepRS), and phosphoseryl-tRNA (tRNA$^{Sep}$) and methods of use in site specific incorporation of phosphoserine into a protein or polypeptide are described. Typically, SepRS preferentially aminoacylates tRNA$^{Sep}$ with O-phosphoserine and the tRNA$^{Sep}$ recognizes at least one codon such as a stop codon. Due to the negative charge of the phosphoserine, Sept-tRNA$^{Sep}$ does not bind elongation factor Tu (EF-Tu). However, mutant EF-Sep proteins are disclosed that bind Sep-tRNA$^{Sep}$ and protect Sep-tRNA$^{Sep}$ from deacylation. In a preferred embodiment the nucleic acids are on vectors and are expressed in cells such as bacterial cells, archeaebacterial cells, and eukaryotic cells. Proteins or polypeptides containing phosphoserine produced by the methods described herein can be used for a variety of applications such as research, antibody production, protein array manufacture and development of cell-based screens for new drug discovery.

18 Claims, 7 Drawing Sheets

(56) References Cited

OTHER PUBLICATIONS

Carlson, et al., "Transfer RNAs that insert selenocysteine", Methods Enzymol, 347:24-39 (2002).
Chatterji and Pachter, "Large multiple organism gene finding by collapsed Gibbs sampling", J Comput Biol., 12(6):599-608 (2005).
Daly and Hearn, "Expression of heterologous proteins in Pichia pastoris: a useful experimental tool in protein engineering and production", J. Mol. Recognit., 18(2):119-38 (2005).
Das and Vothknecht, "Phenylalanyl-tRNA synthetase from the archeon Methanobacterium thermoautotrophicum is an (alphabeta)2 heterotetrameric protein", Biochimie, 81(11):1037-9 (1999).
Debinski, et al., "A wide range of human cancers express interleukin 4 (IL4) receptors that can be targeted with chimeric toxin composed of IL4 and Pseudomonas exotoxin", J. Biol. Chem., 268: 14065-14070 (1993).
Diamond, et al., "Dietary selenium affects methylation of the wobble nucleoside in the anticodon of selenocysteine tRNA([Ser]Sec)", J. Biol. Chem., 268:14215-23 (1993).
Ellman, et al., "Biosynthetic method for introducing unnatural amino acids site-specifically into proteins", methods Enzymol., 202:301-36 (1991).
Engelhard, et al., "The insect tracheal system: a conduit for the systemic spread of Autographa californica M nuclear polyhedrosis virus", Proc. Natl. Acad. Sci. USA, 91:3224-3227 (1994).
Fabrega, et al., "An aminoacyl tRNA synthetase whose sequence fits into neither of the two known classes", Nature, 411:110-4 (2001).
Fleer, et al., "High-level secretion of correctly processed recombinant human interleukin-1 beta in Kluyveromyces lactis", Gene, 107:285-95 (1991).
Florens, et al., A proteomic view of the Plasmodium falciparum life cycle Nature, 419, 520-6 (2002).
Fromm, et al., "Expression of genes transferred into monocot and dicot plant cells by electroporation"Proc. Natl. Acad. Sci. USA, 82, 5824-8 (1985).
Giometti, et al., "Global analysis of a "Simple" ptoteome: Methanococcus jannaschii", J. Chromatogr. B Anal. Technol Biomed. Life Sci., 782(1-2):227-43 (2002).
Harrington, et al., "Formation of de novo centromeres and construction of first-generation human artificial microchromosomes", Nat Genet., 15:345-355 (1997).
Hitzeman, et al., "Isolation and characterization of the yeast 3-phosphoglycerokinase gene (PGK) by an immunological screening technique", J. Biol. Chem., 255:12073-80 (1980).
Hofer, et al., "An engineered selenocysteine defines a unique class of antibody derivatives",PNAS, 105(34):12451-6 (2008).
Hohsaka, et al., "Five-base codons for incorporation of nonnatural amino acids into proteins", Nucleic Acids Res., 29:3646-51 (2001).
Holland and Holland, "Isolation and identification of yeast messenger ribonucleic acids coding for enclase gylceraldehyde-3-phosphate dehydrogenase, and phosphoglycerate kinase", Biochem., 17:4900-7 (1978).
Ibba, et al., "The adaptor hypothesis revisted", Trends Biochem. Sci., 25:311-6 (2000).
Jacob, et al., "Sulfur and selenium: the role of oxidation state in protein structure and function", Angew. Chem. Int. Ed. Engl., 42:4742-58 (2003).
Jansen, et al., "Drag&Drop cloning in yeast", Gene, 344:43-51 (2005).
Johannson, et al., "Selenocysteine in proteins-properties and biotechnological use", Biochim Biophys Acta., 1726:1-13 (2005).
Karlin and Altschul, "Applications and statistics for multiple high-scoring segments in molecular sequences", Proc. Nat'l. Acad. Sci. USA, 90:5873-5787 (1993).
Kim, et al., "Sequence Divergence of Seryl-tRNA Synthetase in Archaea", J. Bacteriol., 180:6446-49 (1998).
Klein, et al., "High velocity microprojectiles for delivering nucleic acids into living cells", Nature, 327:70-73 (1987).
Kreitman and Pastan, "Purification and characterization of IL6-PE4E, a recombinant fusion of interleukin 6 with Pseudomonas exotoxin", Bioconjug. Chem., 4:581-585 (1993).
Kryukov, et al, "Characterization of mammalian selenoproteomas", Science, 300:1439-43 (2003).
Lee, et al., "The discriminator base influence tRNA structure at the end of the acceptor stem and possibly its interaction with proteins", PNAS, 90(15):7149-52 (1993).
Li, et al., "Cysteinyl-tRNA formation: the last puzzle of aminoacyl-tRNA synthesis", FEBS Lett., 462:302 (1999).
Li, et al., "Usage of an intronic promoter for stable gene expression in Saccharomyces cerevisiae", Lett Appl Microbiol , 40(5):347-52 (2005).
Lipman, et al., "Synthesis of cysteinyl-tRNA(Cys) by a genome that lacks the normal cycteine-tRNA synthetase" Biochemistry 39:7792-8 (2000).
Liu, et al., "Catalytic mechanism of Sep-tRNA:Cys-tRNA synthase: sulfur transfer is mediated by disulfide and persulfide", J. Biol. Chem., 287:5426-33 (2012).
Logan and Shenk, "Adenovirus tripartite leader sequence enhances translation of mRNAs late after infection" Proc. Natl. Acad. Sci. USA, 81:3655-3859 (1984).
Maccoss, et al., "Probability-based validation of protein indentifications using a modified SEQUEST algorithm", Anal. Chem., 74:5593-9 (2002).
Margelevicius and Venclovas, "PSI-BLAST-ISS: an intermediate sequence search tool for estimation of the position-specific alignment reliability", BMC Bioinformatics, 6:185 (2005).
Min, et al., "Transfer RNA-dependent amino acid biosynthesis: an essential route to asparagine formation", Proc. Natl. Acad. Sci. U.S.A., 99:2678 (2002).
Mino and Ishikawa, "A novel O-phospho-L-serine sulfhydrylation reaction catalyzed by O-acetylserine sulfhydrylase from Aeropyrum pemix K1", FEBS Lett., 551:133-8 (2003).
Mizutani, et al., "Possible incorporation of phosphoserine into globin reathrough protein via bovine opal suppressor phosphoseryl-tRNA", FEBS Lett., 207(1):162-6 (1986).
Moore, "On the Determination of Cystine as Cysteic Acid", J. Biol. Chem., 238:235-7 (1963).
Needleman and Wunsch, "A general method applicable to the search for similarities in the amino acid sequence of two proteins", J. Mol. Biol., 4(3):443-53 (1970).
Palioura, et al., "The human SepSecS-tRNASec complex reveals the mechanism of selenocysteine formation", Science, 325:321-5 (2009).
Pearson and Lipman, "Improved tools for biological sequence comparison", Proc. Nat'l. Acad. Sci. USA, 85:2444-8 (1988).
Polycarpo, et al., "Activation of the pyrrolysine suppressor tRNA requires formation of a ternary complex with class I and Class II lysl-tRNA synthetases", Mol. Cell, 12:287-94 (2003).
Polycarpo, et al., "An aminocyl-tRNA synthetase that specifically activates pyrrolysine", Proc. Natl. Acad. Sci. U.S.A., 101;12450 (2004).
Raffa, "Diselenium, instead of disulfide, bonded analogs of conotoxins: novel synthesis and pharmacotherapeutic potential", Life Sci., 87(15-16):451-6 (2010).
Riaz and Mehmood, "Selenium in Human Health and Disease: A Review", JPMI, 26(02):120-33 (2012).
Ruan, et al., "Cysteinyl-tRNA(Cys) formation in Methanocaldococcus jannaschil: the mechanism is still unknown", J. Bacteriol. 186, 8-14 (2004).
Rudinger, et al., "Antideterminants present in minihelix(Sec) hinder its recognition by prokaryotic elongation factor Tu", EMBO J., 15(3):650-57 (1996).
Sadygov and Yates, A hypergeometric probability model for protein indentification and validation using tandem mass spectral data and protein sequence databases\, Anal. Chem., 75:3792-8 (2003).
Sandig, et al., "Gene transfer into hepatocytes and human liver tissue by baculovirus vectors", Hum. Gene Ther., 7:1937-1945 (1996).
Schon, et al., "The selenocysteine-inserting opal suppressor serine tRNA from E. coli is highly unusal in structure and modification", Nucleic Acids Res., 17 (18):7159-65 (1989).

(56) References Cited

OTHER PUBLICATIONS

Shchedrina, et al., "Indentification and characterization of a selenoprotein family containing a diselenide bond in a redox motif", PNAS, 104(35):13919-24 (2007).
Sherrer, et al., "Characterization and evolutionary history of an archeal kinase involved in selenocysteinyl-tRNA formation", Nucleic Acids Res., 36(4): 1247-59 (2008b).
Sherrer, et al., "Divergence of selenocysteine tRNA recognition by archeal and eukaryotic O-phosphoseryl-tRNASec kinase", Nucleic Acids Res, 36:1871-80 (2008a).
Smith and Waterman, "Comparison of Biosequences", Adv. Appl. Math., 2:482-89 (1981).
Stathopoulos, et al., "Cysteinyl-tRNA synthetase is not essential for viability of the archeon methanococcus maripaludis", Proc. Natl. Acad. Sci. U.S.A., 98:14292-7 (2001).
Stathpoulos, et al., "One polypeptide with two aminoacyl-tRNA synthetase activities", Science, 287(5452):479-82 (2000).
Tabb, et al., "DTASelect and Contrast: tools for assembling and comparing protein indentifications from shotgun proteomics", J. Proteome Res., 1:21-6 (2002).
Takamatsu, et al., "Expression of bacterial chloramphenicol acetyltransferase gene in tobacco plants mediated by TMV-RNA", EMBO J., 6:307-311 (1987).
Tapiero, et al., "The antioxidant role of selenium and seleno-compounds", Biomed Pharmacother., 57:134-44 (2003).
Tomari, et al., "The role of tightly bound ATP in *Escherichia coli* tRNA nucleotidyltransferase", Genes Cells, 5:68998 (2000).
Tumbula, et al., "Transformation of Methanococcus maripaludis and indentification of a PstI-like restriction system", FEMS Microbiol. Lett., 121:309-14 (1994).
Van Heeke and Schuster, "Expression of human asparagine synthetase in *Escherichia coli*", J. Biol. Chem., 264:5503-5509 (1989).
Varshney, et al., "Direct analysis of aminoacylation levels of tRNAs In Vivo. Application to studying recognition of *Escherichia coli* initiator tRNA mutants by glutaminyl-tRNA synthetase", J. Biol. Chem. 266:24712(1991).
White, "The biosynthesis of cysteine and homocysteine in Methanococcus jannaschii", Biochim. Biophys. Acta. 1624:46-53 (2003).
Whitman, et al., "Isolation and characterization of 22 mesophillic methanococci", Syst. Appl. Microbiol. 7:235-40 (1986).
Wolfson and Uhlenbeck, "Modulation of tRNAAla identity by inorganic pyrophosphatase", Proc. Natl. Acad. Sci. U.S.A., 99:5965-70 (2002).
Wu and Gross, "The length and the secondary structure of the D-stem of human selenocysteine tRNA are the major identity determinants for serine phosphorylation", EMBO J., 13:241-8 (1994).
Xu, et al., "New developments in selenium biochemistry: selenocysteine biosynthesis in eukaryotes and archaea", Biol TraceElem Res., 119(3):234-41 (2007).
Yoshizawa and Böck, "The many levels of control on bacterial selenoprotein synthesis", Biochim Biophys Acta., 1790:1404-14 (2009).
Yuan, et al., "Distinct genetic code expansion strategies for selenocysteine and pyrrolysine are reflected in diffrent aminoacyl-tRNA formation systems", FEBS Lett., 584(2):342-9 (2010).
Yuan, et al., "RNA-dependent conversion of phosphoserine forms selenocysteine in eukaryotes and archaea", PNAS, 103:18923-7 (2006).
Zhang and Hou, "Synthesis of cysteinyl-tRNACys by a prolyl-tRNA synthetase", RNA Biol., 1:35-41 (2004).
Zhu, et al., Shotgun Proteomics of Methanococcus jannaschii and insights into methanogenesis\, J. Proteome Res., 3:538 (2004).
Alessi, et al., "dentification of the sites in MAP kinase kinase-1 phosphorylated by p74raf-1", EMBO J., 13:1610-9 (1994).
Bajaj, et al., "Mutagenesis-based definitions and probes of residue burial in protein", PNAS, 102(45):16221-6 (2005).
Bernard, et al., "Positive-selection vectors using the F plasmid ccdB killer gene", Gene, 148:71-4 (1994).
Bunjun, et al., "A dual-specificity aminoacyl-tRNA synthetase in the deep-rooted eukaryote Giardia lamblia", PNAS, 97:12997-13002 (2000).
Dale, et al., "The affinity of elongation factor Tu for an aminoacyl-tRNA is modulated by the esterified amino acid", Biochemistry 43:6159-66 (2004).
Datsenko, et al., "One-step inactivation of chromosomal genes in *Escherichia coli* K-12 using PCR products", PNAS, 97:6640-5 (2000).
Eargle, et al., "Dynamics of Recognition between tRNA and elongation factor Tu", J Mol Biol., 377(5):1382-1405 (2008).
Fukunaga, et al., "Structural insights into the first steps of RNA-dependent cysteine biosynthesis in archaea", Nat Struct Mol Biol., 14:272-9 (2007).
Hohn, et al., "Emergence of the universal genetic code imprinted in an RNA record", PNAS, 103(48):18095-100 (2006).
Kamtekar, et al., "Toward understanding phosphoseryl-tRNACys formation: the crystal structure of Methanococcus maripaludis phosphoseryl-tRNA synthetase", PNAS, 104(8):2620-5 (2007).
LaRiviere, et al., "Uniform binding of aminoacyl-tRNAs to elongation factor Tu by thermodynamic compensation", Science, 294(5540):165-8 (2001).
Ling, et al., "Pathogenic mechanism of a human mitochondrial tRNAPhe mutation associated with myoclonic epilepsy with ragged red fibers syndrome", PNAS, 104(39):15299-304 (2007a).
Ling , et al., "Phenylalanyl-tRNA synthetase editing defects result in efficient mistranslation of phenylalanine codons as tyrosine", RNA., 13(11):1881-6(2007b).
Nissen, et al., "Crystal structure of the ternary complex of Phe-tRNAPhe, EF-Tu, and a GTP analog", Science, 270(5241)1464-72 (1995).
Normanly , et al., "Changing the indentity of a transfer RNA", Nature, 321:213-9 (1986).
Park, et al., "Design and evolution of new catalytic activity with an existing protein scaffold", Science 311(5760):535-8 (2006).
Park, et al., "Expanding the genetic code of *Escherichia coli* with phosphoserine", Science, 33(6046):1151-4 (2011).
Rothman, et al., "Caged phosphoproteins", J Am Chem Soc., 127(3):846-7 (2005).
Sauerwald, et al., "RNA-dependent cysteine biosynthesis in archaea", Science, 307(5717):1969-72 (2005).
Sebolt-Leopold, et al., "Targeting the mitogen-activated protein kinase cascade to treat cancer", Nat Rev Cancer, 4:937-47 (2004).
Studier, "Protein production by auto-induction in high density shaking cultures", Protein Expr Purif.,41(1):207-34 (2005).
Wang, et al., "Expanding the genetic code of *Escherichia coli* ", Science, 292 (5516):498-500 (2001).
Wanner, "Molecular genetic studies of a 10.9-kb operon in *Escherichia coli* for phosphonate uptake and biodegradation", FEMS Microbiol Lett., 79(1-):133-9 (1992).
Zhang, et al., "Aminoacylation of tRNA with phosphoserine for synthesis of cysteinyl-tRNA(Cys", Nat. Struct Mol. Biol., 15(5):507-14 (2008).

\* cited by examiner

SEQUENCE LISTING

```
<160> NUMBER OF SEQ ID NOS: 46

<210> SEQ ID NO 1
<211> LENGTH: 409
<212> TYPE: PRT
<213> ORGANISM: Artificial Sequence
<220> FEATURE:
<223> OTHER INFORMATION: Synthetic Construct

<400> SEQUENCE: 1

Met Ser Lys Glu Lys Phe Glu Arg Thr Lys Pro His Val Asn Val Gly
1               5                   10                  15

Thr Ile Gly His Val Asp His Gly Lys Thr Thr Leu Thr Ala Ala Ile
            20                  25                  30

Thr Thr Val Leu Ala Lys Thr Tyr Gly Gly Thr Ala Arg Ala Phe Asp
        35                  40                  45

Gln Ile Asp Asn Ala Pro Glu Glu Lys Ala Arg Gly Ile Thr Ile Asn
    50                  55                  60

Thr Ser Arg Val Glu Tyr Asp Thr Pro Thr Arg His Tyr Ala His Val
65                  70                  75                  80

Asp Cys Pro Gly His Ala Asp Tyr Val Lys Asn Met Ile Thr Gly Ala
                85                  90                  95

Ala Gln Met Asp Gly Ala Ile Leu Val Val Ala Ala Thr Asp Gly Pro
            100                 105                 110
```

```
Met Pro Gln Thr Arg Glu His Ile Leu Leu Gly Arg Gln Val Gly Val
            115                 120                 125

Pro Tyr Ile Ile Val Phe Leu Asn Lys Cys Asp Met Val Asp Asp Glu
        130                 135                 140

Glu Leu Glu Leu Val Glu Met Glu Val Arg Glu Leu Leu Ser Gln
145                 150                 155                 160

Tyr Asp Phe Pro Gly Asp Asp Thr Pro Ile Val Arg Gly Ser Ala Leu
                165                 170                 175

Lys Ala Leu Glu Gly Asp Ala Glu Trp Glu Ala Lys Ile Leu Glu Leu
            180                 185                 190

Ala Gly Phe Leu Asp Ser Tyr Ile Pro Glu Pro Glu Arg Ala Ile Asp
        195                 200                 205

Lys Pro Phe Leu Leu Pro Ile Thr Arg Val Tyr Ser Ile Ser Gly Arg
    210                 215                 220

Gly Thr Val Val Ser Gly Arg Val Glu Arg Gly Ile Ile Lys Val Gly
225                 230                 235                 240

Glu Glu Val Glu Ile Val Gly Ile Lys Glu Thr Gln Lys Ser Thr Cys
                245                 250                 255

Thr Gly Val Glu Met Phe Arg Lys Leu Leu Asp Glu Gly Arg Ala Gly
            260                 265                 270

Glu Phe Val Gly Val Leu Leu Arg Gly Ile Lys Arg Glu Glu Ile Glu
        275                 280                 285

Arg Gly Gln Val Leu Ala Lys Pro Gly Thr Ile Lys Pro His Thr Lys
    290                 295                 300

Phe Glu Ser Glu Val Tyr Ile Leu Ser Lys Asp Glu Gly Gly Arg His
305                 310                 315                 320

Thr Pro Phe Phe Lys Gly Tyr Arg Pro Gln Phe Tyr Phe Arg Thr Thr
                325                 330                 335

Asp Val Thr Gly Thr Ile Glu Leu Pro Glu Gly Val Glu Met Val Met
            340                 345                 350

Pro Gly Asp Asn Ile Lys Met Val Val Thr Leu Ile His Pro Ile Ala
        355                 360                 365

Met Asp Asp Gly Leu Arg Phe Ala Ile Arg Glu Gly Gly Arg Thr Val
    370                 375                 380

Gly Ala Gly Val Val Ala Lys Val Leu Arg Asp Pro Asn Ser Ser Ser
385                 390                 395                 400

Val Asp Lys Leu Ala Ala Ala Leu Glu
                405

<210> SEQ ID NO 2
<211> LENGTH: 409
<212> TYPE: PRT
<213> ORGANISM: Artificial Sequence
<220> FEATURE:
<223> OTHER INFORMATION: Synthetic Construct

<400> SEQUENCE: 2

Met Ser Lys Glu Lys Phe Glu Arg Thr Lys Pro His Val Asn Val Gly
1               5                   10                  15

Thr Ile Gly His Val Asp His Gly Lys Thr Thr Leu Thr Ala Ala Ile
            20                  25                  30

Thr Thr Val Leu Ala Lys Thr Tyr Gly Gly Ala Ala Arg Ala Phe Asp
        35                  40                  45

Gln Ile Asp Asn Ala Pro Glu Glu Lys Ala Arg Gly Ile Thr Ile Asn
    50                  55                  60
```

```
Thr Ser Arg Val Glu Tyr Asp Thr Pro Thr Arg His Tyr Ala His Val
 65                  70                  75                  80

Asp Cys Pro Gly His Ala Asp Tyr Val Lys Asn Met Ile Thr Gly Ala
                 85                  90                  95

Ala Gln Met Asp Gly Ala Ile Leu Val Ala Ala Thr Asp Gly Pro
            100                 105                 110

Met Pro Gln Thr Arg Glu His Ile Leu Leu Gly Arg Gln Val Gly Val
            115                 120                 125

Pro Tyr Ile Ile Val Phe Leu Asn Lys Cys Asp Met Val Asp Asp Glu
        130                 135                 140

Glu Leu Leu Glu Leu Val Glu Met Glu Val Arg Glu Leu Leu Ser Gln
145                 150                 155                 160

Tyr Asp Phe Pro Gly Asp Asp Thr Pro Ile Val Arg Gly Ser Ala Leu
                165                 170                 175

Lys Ala Leu Glu Gly Asp Ala Glu Trp Glu Ala Lys Ile Leu Glu Leu
            180                 185                 190

Ala Gly Phe Leu Asp Ser Tyr Ile Pro Glu Pro Glu Arg Ala Ile Asp
        195                 200                 205

Lys Pro Phe Leu Leu Pro Ile Thr Tyr Val Tyr Ser Ile Ser Gly Arg
210                 215                 220

Gly Thr Val Val Ser Gly Arg Val Glu Arg Gly Ile Ile Lys Val Gly
225                 230                 235                 240

Glu Glu Val Glu Ile Val Gly Ile Asn Glu Thr Gln Lys Ser Thr Cys
                245                 250                 255

Thr Gly Val Glu Met Phe Arg Lys Leu Leu Asp Glu Gly Arg Ala Gly
            260                 265                 270

Glu Ala Val Gly Val Leu Leu Arg Gly Ile Lys Arg Glu Glu Ile Glu
        275                 280                 285

Arg Gly Gln Val Leu Ala Lys Pro Gly Thr Ile Lys Pro His Thr Lys
290                 295                 300

Phe Glu Ser Glu Val Tyr Ile Leu Ser Lys Asp Glu Gly Gly Arg His
305                 310                 315                 320

Thr Pro Phe Phe Lys Gly Tyr Arg Pro Gln Phe Tyr Phe Arg Thr Thr
                325                 330                 335

Asp Val Thr Gly Thr Ile Glu Leu Pro Glu Gly Val Glu Met Val Met
            340                 345                 350

Pro Gly Asp Asn Ile Lys Met Val Val Thr Leu Ile His Pro Ile Ala
        355                 360                 365

Met Asp Asp Gly Leu Arg Phe Ala Ile Arg Glu Gly Gly Arg Thr Val
    370                 375                 380

Gly Ala Gly Val Val Ala Lys Val Leu Arg Asp Pro Asn Ser Ser Ser
385                 390                 395                 400

Val Asp Lys Leu Ala Ala Ala Leu Glu
                405

<210> SEQ ID NO 3
<211> LENGTH: 409
<212> TYPE: PRT
<213> ORGANISM: Artificial Sequence
<220> FEATURE:
<223> OTHER INFORMATION: Synthetic Construct

<400> SEQUENCE: 3

Met Ser Lys Glu Lys Phe Glu Arg Thr Lys Pro His Val Asn Val Gly
1               5                   10                  15
```

-continued

```
Thr Ile Gly His Val Asp His Gly Lys Thr Thr Leu Thr Ala Ala Ile
             20                  25                  30

Thr Thr Val Leu Ala Lys Thr Tyr Gly Gly Ala Ala Arg Ala Phe Asp
         35                  40                  45

Gln Ile Asp Asn Ala Pro Glu Glu Lys Ala Arg Gly Ile Thr Ile Asn
 50                  55                  60

Thr Ser Arg Val Glu Tyr Asp Thr Pro Thr Arg His Tyr Ala His Val
 65                  70                  75                  80

Asp Cys Pro Gly His Ala Asp Tyr Val Lys Asn Met Ile Thr Gly Ala
                 85                  90                  95

Ala Gln Met Asp Gly Ala Ile Leu Val Val Ala Ala Thr Asp Gly Pro
            100                 105                 110

Met Pro Gln Thr Arg Glu His Ile Leu Leu Gly Arg Gln Val Gly Val
            115                 120                 125

Pro Tyr Ile Ile Val Phe Leu Asn Lys Cys Asp Met Val Asp Asp Glu
130                 135                 140

Glu Leu Glu Leu Val Glu Met Glu Val Arg Glu Leu Leu Ser Gln
145                 150                 155                 160

Tyr Asp Phe Pro Gly Asp Asp Thr Pro Ile Val Arg Gly Ser Ala Leu
                165                 170                 175

Lys Ala Leu Glu Gly Asp Ala Glu Trp Glu Ala Lys Ile Leu Glu Leu
            180                 185                 190

Ala Gly Phe Leu Asp Ser Tyr Ile Pro Glu Pro Glu Arg Ala Ile Asp
                195                 200                 205

Lys Pro Phe Leu Leu Pro Ile Asn Gly Val Tyr Ser Ile Ser Gly Arg
210                 215                 220

Gly Thr Val Val Ser Gly Arg Val Glu Arg Gly Ile Ile Lys Val Gly
225                 230                 235                 240

Glu Glu Val Glu Ile Val Gly Ile Lys Glu Thr Gln Lys Ser Thr Cys
                245                 250                 255

Thr Gly Val Glu Met Phe Arg Lys Leu Leu Asp Glu Gly Arg Ala Gly
            260                 265                 270

Glu Trp Val Gly Val Leu Leu Arg Gly Ile Lys Arg Glu Glu Ile Glu
        275                 280                 285

Arg Gly Gln Val Leu Ala Lys Pro Gly Thr Ile Lys Pro His Thr Lys
290                 295                 300

Phe Glu Ser Glu Val Tyr Ile Leu Ser Lys Asp Glu Gly Gly Arg His
305                 310                 315                 320

Thr Pro Phe Phe Lys Gly Tyr Arg Pro Gln Phe Tyr Phe Arg Thr Thr
                325                 330                 335

Asp Val Thr Gly Thr Ile Glu Leu Pro Glu Gly Val Glu Met Val Met
            340                 345                 350

Pro Gly Asp Asn Ile Lys Met Val Val Thr Leu Ile His Pro Ile Ala
            355                 360                 365

Met Asp Asp Gly Leu Arg Phe Ala Ile Arg Glu Gly Gly Arg Thr Val
        370                 375                 380

Gly Ala Gly Val Val Ala Lys Val Leu Arg Asp Pro Asn Ser Ser Ser
385                 390                 395                 400

Val Asp Lys Leu Ala Ala Ala Leu Glu
                405
```

<210> SEQ ID NO 4
<211> LENGTH: 409
<212> TYPE: PRT

<213> ORGANISM: Artificial Sequence
<220> FEATURE:
<223> OTHER INFORMATION: Synthetic Construct

<400> SEQUENCE: 4

```
Met Ser Lys Glu Lys Phe Glu Arg Thr Lys Pro His Val Asn Val Gly
1               5                   10                  15

Thr Ile Gly His Val Asp His Gly Lys Thr Thr Leu Thr Ala Ala Ile
            20                  25                  30

Thr Thr Val Leu Ala Lys Thr Tyr Gly Gly Ala Ala Arg Ala Phe Asp
        35                  40                  45

Gln Ile Asp Asn Ala Pro Glu Glu Lys Ala Arg Gly Ile Thr Ile Asn
50                  55                  60

Thr Ser Arg Val Glu Tyr Asp Thr Pro Thr His Tyr Ala His Val
65                  70                  75                  80

Asp Cys Pro Gly His Ala Asp Tyr Val Lys Asn Met Ile Thr Gly Ala
                85                  90                  95

Ala Gln Met Asp Gly Ala Ile Leu Val Val Ala Ala Thr Asp Gly Pro
            100                 105                 110

Met Pro Gln Thr Arg Glu His Ile Leu Leu Gly Arg Gln Val Gly Val
        115                 120                 125

Pro Tyr Ile Ile Val Phe Leu Asn Lys Cys Asp Met Val Asp Asp Glu
130                 135                 140

Glu Leu Leu Glu Leu Val Glu Met Glu Val Arg Glu Leu Leu Ser Gln
145                 150                 155                 160

Tyr Asp Phe Pro Gly Asp Asp Thr Pro Ile Val Arg Gly Ser Ala Leu
                165                 170                 175

Lys Ala Leu Glu Gly Asp Ala Glu Trp Glu Ala Lys Ile Leu Glu Leu
            180                 185                 190

Ala Gly Phe Leu Asp Ser Tyr Ile Pro Glu Pro Glu Arg Ala Ile Asp
        195                 200                 205

Lys Pro Phe Leu Leu Pro Ile Thr Ala Val Tyr Ser Ile Ser Gly Arg
210                 215                 220

Gly Thr Val Val Ser Gly Arg Val Glu Arg Gly Ile Ile Lys Val Gly
225                 230                 235                 240

Glu Glu Val Glu Ile Val Gly Ile Lys Glu Thr Gln Lys Ser Thr Cys
                245                 250                 255

Thr Gly Val Glu Met Phe Arg Lys Leu Leu Asp Glu Gly Arg Ala Gly
            260                 265                 270

Glu Ala Val Gly Val Leu Leu Arg Gly Ile Lys Arg Glu Glu Ile Glu
        275                 280                 285

Arg Gly Gln Val Leu Ala Lys Pro Gly Thr Ile Lys Pro His Thr Lys
290                 295                 300

Phe Glu Ser Glu Val Tyr Ile Leu Ser Lys Asp Glu Gly Gly Arg His
305                 310                 315                 320

Thr Pro Phe Phe Lys Gly Tyr Arg Pro Gln Phe Tyr Phe Arg Thr Thr
                325                 330                 335

Asp Val Thr Gly Thr Ile Glu Leu Pro Glu Gly Val Glu Met Val Met
            340                 345                 350

Pro Gly Asp Asn Ile Lys Met Val Thr Leu Ile His Pro Ile Ala
        355                 360                 365

Met Asp Asp Gly Leu Arg Phe Ala Ile Arg Glu Gly Gly Arg Thr Val
370                 375                 380

Gly Ala Gly Val Val Ala Lys Val Leu Arg Asp Pro Asn Ser Ser Ser
```

```
                385                 390                 395                 400
Val Asp Lys Leu Ala Ala Ala Leu Glu
                            405
```

<210> SEQ ID NO 5
<211> LENGTH: 1227
<212> TYPE: DNA
<213> ORGANISM: Artificial Sequence
<220> FEATURE:
<223> OTHER INFORMATION: Synthetic Construct

<400> SEQUENCE: 5

```
atgtctaaag aaaagtttga acgtacaaaa ccgcacgtta acgtcggtac tatcggccac    60
gttgaccatg gtaaaacaac gctgaccgct gcaatcacta ccgtactggc taaaacctac   120
ggcggtactc tcgcgcatt cgaccagatc gataacgcgc ggaagaaaa agctcgtggt   180
atcaccatca acacttctcg ggttgaatac gacacccccga cccgtcacta cgcacacgta   240
gactgcccgg ggcacgccga ctatgttaaa aacatgatca ccggtgctgc gcagatggac   300
ggcgcgatcc tggtagttgc tgcgactgac ggcccgatgc cgcagactcg tgagcacatc   360
ctgctgggtc gtcaggtagg cgttccgtac atcatcgtgt tcctgaacaa atgcgacatg   420
gttgatgacg aagagctgct ggaactggtt gaaatggaag ttcgtgaact tctgtctcag   480
tacgacttcc cgggcgacga cactccgatc gttcgtggtt ctgctctgaa agcgctggaa   540
ggcgacgcag agtgggaagc gaaaatcctg gaactggctg gcttcctgga ttcttacatt   600
ccggaaccag agcgtgcgat tgacaagccg ttcctgctgc cgatcacccg ggtatactcc   660
atctccggtc gtggtaccgt tgtttcgggt cgtgtagaac gcggtatcat caaagttggt   720
gaagaagttg aaatcgttgg tatcaaagag actcagaagt ctacctgtac tggcgttgaa   780
atgttccgca aactgctgga cgaaggccgt gctggtgagt cgtaggtgt tctgctgcgt   840
ggtatcaaac gtgaagaaat cgaacgtggt caggtactgg ctaagccggg caccatcaag   900
ccgcacacca agttcgaatc tgaagtgtac attctgtcca agatgaagg cggccgtcat   960
actccgttct tcaaaggcta ccgtccgcag ttctacttcc gtactactga cgtgactggt  1020
accatcgaac tgccggaagg cgtagagatg gtaatgccgg cgacaacat caaaatggtt  1080
gttaccctga tccacccgat cgcgatggac gacggtctgc gtttcgcaat ccgtgaaggc  1140
ggccgtaccg ttggcgcggg cgttgtagca aagttctga gggatccgaa ttcgagctcc  1200
gtcgacaagc ttgcggccgc actcgag                                     1227
```

<210> SEQ ID NO 6
<211> LENGTH: 1227
<212> TYPE: DNA
<213> ORGANISM: Artificial Sequence
<220> FEATURE:
<223> OTHER INFORMATION: Synthetic Construct

<400> SEQUENCE: 6

```
atgtctaaag aaaagtttga acgtacaaaa ccgcacgtta acgtcggtac tatcggccac    60
gttgaccatg gtaaaacaac gctgaccgct gcaatcacta ccgtactggc taaaacctac   120
ggcggtgctc tcgcgcatt cgaccagatc gataacgcgc ggaagaaaa agctcgtggt   180
atcaccatca acacttctag ggttgaatac gacacccccga cccgtcacta cgcacacgta   240
gactgcccgg ggcacgccga ctatgttaaa aacatgatca ccggtgctgc gcagatggac   300
ggcgcgatcc tggtagttgc tgcgactgac ggcccgatgc cgcagactcg tgagcacatc   360
```

```
ctgctgggtc gtcaggtagg cgttccgtac atcatcgtgt tcctgaacaa atgcgacatg      420
gttgatgacg aagagctgct ggaactggtt gaaatggaag ttcgtgaact tctgtctcag      480
tacgacttcc cgggcgacga cactccgatc gttcgtggtt ctgctctgaa agcgctggaa      540
ggcgacgcag agtgggaagc gaaaatcctg gaactggctg gcttcctgga ttcttacatt      600
ccggaaccag agcgtgcgat tgacaagccg ttcctgctgc cgatcaccta cgtatactcc      660
atctccggtc gtggtaccgt tgtttcgggt cgtgtagaac gcggtatcat caaagttggt      720
gaagaagttg aaatcgttgg tatcaatgag actcagaagt ctacctgtac tggcgttgaa      780
atgttccgca actgctgga cgaaggccgt gctggtgagg cggtaggtgt tctgctgcgt       840
ggtatcaaac gtgaagaaat cgaacgtggt caggtactgg ctaagccggg caccatcaag      900
ccgcacacca gttcgaatc tgaagtgtac attctgtcca aagatgaagg cggccgtcat       960
actccgttct tcaaaggcta ccgtccgcag ttctacttcc gtactactga cgtgactggt     1020
accatcgaac tgccggaagg cgtagagatg gtaatgccgg gcgacaacat caaaatggtt     1080
gttaccctga tccacccgat cgcgatggac gacggtctgc gtttcgcaat ccgtgaaggc     1140
ggccgtaccg ttggcgcggg cgttgtagca aaagttctga gggatccgaa ttcgagctcc     1200
gtcgacaagc ttgcggccgc actcgag                                         1227

<210> SEQ ID NO 7
<211> LENGTH: 1227
<212> TYPE: DNA
<213> ORGANISM: Artificial Sequence
<220> FEATURE:
<223> OTHER INFORMATION: Synthetic Construct

<400> SEQUENCE: 7
atgtctaaag aaaagtttga acgtacaaaa ccgcacgtta acgtcggtac tatcggccac       60
gttgaccatg gtaaaacaac gctgaccgct gcaatcacta ccgtactggc taaaacctac      120
ggcggtgctg ctcgcgcatt cgaccagatc gataacgcgc cggaagaaaa agctcgtggt      180
atcaccatca acacttctcg ggttgaatac gacaccccga cccgtcacta cgcacacgta      240
gactgcccgg gcacgccgga ctatgttaaa aacatgatca ccggtgctgc gcagatggac      300
ggcgcgatcc tggtagttgc tgcgactgac ggcccgatgc cgcagactcg tgagcacatc      360
ctgctgggtc gtcaggtagg cgttccgtac atcatcgtgt tcctgaacaa atgcgacatg      420
gttgatgacg aagagctgct ggaactggtt gaaatggaag ttcgtgaact tctgtctcag      480
tacgacttcc cgggcgacga cactccgatc gttcgtggtt ctgctctgaa agcgctggaa      540
ggcgacgcag agtgggaagc gaaaatcctg gaactggctg gcttcctgga ttcttacatt      600
ccggaaccag agcgtgcgat tgacaagccg ttcctgctgc cgatcaacgg gtatactcc       660 atctccggtc gtggtaccgt tgtttcgggt cgtgtagaac gcggtatcat caaagttggt      720
gaagaagttg aaatcgttgg tatcaaagag actcagaagt ctacctgtac tggcgttgaa      780
atgttccgca actgctgga cgaaggccgt gctggtgagt gggtaggtgt tctgctgcgt       840
ggtatcaaac gtgaagaaat cgaacgtggt caggtactgg ctaagccggg caccatcaag      900
ccgcacacca gttcgaatc tgaagtgtac attctgtcca aagatgaagg cggccgtcat       960
actccgttct tcaaaggcta ccgtccgcag ttctacttcc gtactactga cgtgactggt     1020
accatcgaac tgccggaagg cgtagagatg gtaatgccgg gcgacaacat caaaatggtt     1080
gttaccctga tccacccgat cgcgatggac gacggtctgc gtttcgcaat ccgtgaaggc     1140
ggccgtaccg ttggcgcggg cgttgtagca aaagttctga gggatccgaa ttcgagctcc     1200
```

```
gtcgacaagc ttgcggccgc actcgag                                       1227

<210> SEQ ID NO 8
<211> LENGTH: 1227
<212> TYPE: DNA
<213> ORGANISM: Artificial Sequence
<220> FEATURE:
<223> OTHER INFORMATION: Synthetic Construct

<400> SEQUENCE: 8
atgtctaaag aaaagtttga acgtacaaaa ccgcacgtta acgtcggtac tatcggccac     60
gttgaccatg gtaaaacaac gctgaccgct gcaatcacta ccgtactggc taaaacctac    120
ggcggtgctg ctcgcgcatt cgaccagatc gataacgcgc ggaagaaaa agctcgtggt     180
atcaccatca acacttctcg ggttgaatac gacaccccga cccgtcacta cgcacacgta    240
gactgcccgg ggcacgccga ctatgttaaa aacatgatca ccggtgctgc gcagatggac    300
ggcgcgatcc tggtagttgc tgcgactgac ggcccgatgc cgcagactcg tgagcacatc    360
ctgctgggtc gtcaggtagg cgttccgtac atcatcgtgt tcctgaacaa atgcgacatg    420
gttgatgacg aagagctgct ggaactggtt gaaatggaag ttcgtgaact tctgtctcag    480
tacgacttcc cgggcgacga cactccgatc gttcgtggtt ctgctctgaa agcgctggaa    540
ggcgacgcag agtgggaagc gaaaatcctg gaactggctg gcttcctgga ttcttacatt    600
ccggaaccag agcgtgcgat tgacaagccg ttcctgctgc cgatcaccgc ggtatactcc    660
atctccggtc gtggtaccgt tgtttcgggt cgtgtagaac gcggtatcat caaagttggt    720
gaagaagttg aaatcgttgg tatcaaagag actcagaagt ctacctgtac tggcgttgaa    780
atgttccgca actgctgga cgaaggccgt gctggtgagg ccgtaggtgt tctgctgcgt    840
ggtatcaaac gtgaagaaat cgaacgtggt caggtactgg ctaagccggg caccatcaag    900
ccgcacacca gttcgaatc tgaagtgtac attctgtcca agatgaagg cggccgtcat     960
actccgttct tcaaaggcta ccgtccgcag ttctacttcc gtactactga cgtgactggt   1020
accatcgaac tgccggaagg cgtagagatg gtaatgccgg cgacaacat caaaatggtt   1080
gttaccctga tccacccgat cgcgatggac gacggtctgc gtttcgcaat ccgtgaaggc   1140
ggccgtaccg ttggcgcggg cgttgtagca aaagttctga gggatccgaa ttcgagctcc   1200
gtcgacaagc ttgcggccgc actcgag                                       1227

<210> SEQ ID NO 9
<211> LENGTH: 36
<212> TYPE: DNA
<213> ORGANISM: Artificial Sequence
<220> FEATURE:
<223> OTHER INFORMATION: Synthetic Construct

<400> SEQUENCE: 9
tgcgcaatgc ggccgcccgt agcgccgatg gtagtg                               36

<210> SEQ ID NO 10
<211> LENGTH: 33
<212> TYPE: DNA
<213> ORGANISM: Artificial Sequence
<220> FEATURE:
<223> OTHER INFORMATION: Synthetic Construct

<400> SEQUENCE: 10
acacggagat ctctaaagta tatatgagta aac                                  33
```

<210> SEQ ID NO 11
<211> LENGTH: 37
<212> TYPE: DNA
<213> ORGANISM: Artificial Sequence
<220> FEATURE:
<223> OTHER INFORMATION: Synthetic Construct

<400> SEQUENCE: 11
tgcgcaatgc ggccgcccgg gtcgaatttg ctttcga                              37

<210> SEQ ID NO 12
<211> LENGTH: 33
<212> TYPE: DNA
<213> ORGANISM: Artificial Sequence
<220> FEATURE:
<223> OTHER INFORMATION: Synthetic Construct

<400> SEQUENCE: 12
acacggagat ctatgccccg cgcccaccgg aag                                  33

<210> SEQ ID NO 13
<211> LENGTH: 38
<212> TYPE: DNA
<213> ORGANISM: Artificial Sequence
<220> FEATURE:
<223> OTHER INFORMATION: Synthetic Construct

<400> SEQUENCE: 13
tgcagcaatg cggccgcttt caccgtcatc accgaaac                             38

<210> SEQ ID NO 14
<211> LENGTH: 32
<212> TYPE: DNA
<213> ORGANISM: Artificial Sequence
<220> FEATURE:
<223> OTHER INFORMATION: Synthetic Construct

<400> SEQUENCE: 14
gggacgctag caaacaaaaa gagtttgtag aa                                   32

<210> SEQ ID NO 15
<211> LENGTH: 32
<212> TYPE: DNA
<213> ORGANISM: Artificial Sequence
<220> FEATURE:
<223> OTHER INFORMATION: Synthetic Construct

<400> SEQUENCE: 15
gggacgctag cttttctctg gtcccgccgc at                                   32

<210> SEQ ID NO 16
<211> LENGTH: 37
<212> TYPE: DNA
<213> ORGANISM: Artificial Sequence
<220> FEATURE:
<223> OTHER INFORMATION: Synthetic Construct

<400> SEQUENCE: 16
tgcgcaatgc ggccgcggtg gcactttcg gggaaat                               37

<210> SEQ ID NO 17
<211> LENGTH: 30
<212> TYPE: DNA
<213> ORGANISM: Artificial Sequence
<220> FEATURE:
<223> OTHER INFORMATION: Synthetic Construct

<400> SEQUENCE: 17
gcatgcgccg ccagctgttg cccgtctcgc                                      30

<210> SEQ ID NO 18
<211> LENGTH: 31
<212> TYPE: DNA
<213> ORGANISM: Artificial Sequence
<220> FEATURE:
<223> OTHER INFORMATION: Synthetic Construct

<400> SEQUENCE: 18
gcatagatct tcagctggcg aaagggggat g                                    31

<210> SEQ ID NO 19
<211> LENGTH: 41
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (21)..(23)
<223> OTHER INFORMATION: n is a, c, g, or t

<400> SEQUENCE: 19
gtatcaccat caacacttct nnngttgaat acgacacccc g                         41

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct

<400> SEQUENCE: 20
agaagtgttg atggtgatac                                                 20

<210> SEQ ID NO 21
<211> LENGTH: 48
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (19)..(24)
<223> OTHER INFORMATION: n is a, c, g, or t
<220> FEATURE:
<221> NAME/KEY: misc_feature
<222> LOCATION: (28)..(30)
<223> OTHER INFORMATION: n is a, c, g, or t

<400> SEQUENCE: 21
ccgttcctgc tgccgatcnn nnnngtannn tccatctccg gtcgtggt                  48

<210> SEQ ID NO 22
<211> LENGTH: 18
<212> TYPE: DNA
<213> ORGANISM: Artificial Sequence
<220> FEATURE:
<223> OTHER INFORMATION: Synthetic Construct

<400> SEQUENCE: 22
gatcggcagc aggaacgg                                                   18

<210> SEQ ID NO 23

```
<211> LENGTH: 38
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (19)..(21)
<223> OTHER INFORMATION: n is a, c, g, or t

<400> SEQUENCE: 23
ggtcgtggta ccgttgttnn nggtcgtgta gaacgcgg                                38

<210> SEQ ID NO 24
<211> LENGTH: 18
<212> TYPE: DNA
<213> ORGANISM: Artificial Sequence
<220> FEATURE:
<223> OTHER INFORMATION: Synthetic Construct

<400> SEQUENCE: 24
aacaacggta ccacgacc                                                     18

<210> SEQ ID NO 25
<211> LENGTH: 38
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (19)..(21)
<223> OTHER INFORMATION: n is a, c, g, or t

<400> SEQUENCE: 25
gaaggccgtg ctggtgagnn ngtaggtgtt ctgctgcg                                38

<210> SEQ ID NO 26
<211> LENGTH: 18
<212> TYPE: DNA
<213> ORGANISM: Artificial Sequence
<220> FEATURE:
<223> OTHER INFORMATION: Synthetic Construct

<400> SEQUENCE: 26
ctcaccagca cggccttc                                                     18

<210> SEQ ID NO 27
<211> LENGTH: 28
<212> TYPE: DNA
<213> ORGANISM: Artificial Sequence
<220> FEATURE:
<223> OTHER INFORMATION: Synthetic Construct

<400> SEQUENCE: 27
ggaattccat atggcggcgg cggcggcg                                          28

<210> SEQ ID NO 28
<211> LENGTH: 27
<212> TYPE: DNA
<213> ORGANISM: Artificial Sequence
<220> FEATURE:
<223> OTHER INFORMATION: Synthetic Construct

<400> SEQUENCE: 28
ccgctcgagt taagatctgt atcctgg                                           27
```

```
<210> SEQ ID NO 29
<211> LENGTH: 30
<212> TYPE: DNA
<213> ORGANISM: Artificial Sequence
<220> FEATURE:
<223> OTHER INFORMATION: Synthetic Construct

<400> SEQUENCE: 29
aaggaaatta atgaaaatcg aagaaggtaa                                       30

<210> SEQ ID NO 30
<211> LENGTH: 18
<212> TYPE: DNA
<213> ORGANISM: Artificial Sequence
<220> FEATURE:
<223> OTHER INFORMATION: Synthetic Construct

<400> SEQUENCE: 30
ctagaggatc cggcgcgc                                                    18

<210> SEQ ID NO 31
<211> LENGTH: 1215
<212> TYPE: DNA
<213> ORGANISM: Artificial Sequence
<220> FEATURE:
<223> OTHER INFORMATION: Synthetic Construct

<400> SEQUENCE: 31
atgccgaaga agaaaccgac cccgatccag ctgaacccgg ctccggacgg ttctgctgtt      60
aacggcacct cttctgctga aaccaacctg gaagctctgc aaaagaaact ggaagaactg     120
gaactggacg aacagcagcg taaacgtctg gaagcgttcc tgacccagaa acagaaagtt     180
ggtgaactga agacgacga cttcgaaaaa atctctgaac tgggtgctgg taacggtggt     240
gttgttttca agtttctca caaaccgtcc ggtctggtta tggctcgtaa actgatccac      300
ctggaaatca aaccggctat ccgtaaccag atcatccgtg aactgcaagt tctgcacgaa     360
tgcaactctc cgtacatcgt tggtttctac ggtgctttct actctgacgg tgaaatctct     420
atctgcatgg aacacatgga cggtggttct ctggaccagg ttctgaaaaa agctggtcgt     480
atcccggaac agatcctggg taaagtttct atcgctgtta tcaaaggtct gacctacctg     540
cgtgaaaaac acaaaatcat gcaccgtgac gttaaaccgt ctaacatcct ggttaactct     600
cgtggtgaaa tcaaactgtg cgacttcggt gtttctggtc agctgatcga ctctatggct     660
aactctttcg ttggcacccg ttcttacatg tctccggaac gtctgcaagg cacccactac     720
tctgttcagt ctgacatctg gtctatgggt ctgtctctgg ttgaaatggc tgttggtcgt     780
tacccgatcc cgccgccgga cgctaaagaa ctggaactga tgttcggttg ccaggttgaa     840
ggtgacgctg ctgaaacccc gccgcgtccg cgtactccgg tcgtccgct gtcttcttac      900 ggtatggact ctcgtccgcc gatggctatc ttcgaactgc tggactacat cgttaacgaa     960
ccgccgccga aactgccgtc tggtgttttc tctctggagt ccaggactt cgttaacaaa     1020 tgcctgatca aaaacccggc tgaacgtgct gacctgaaac agctgatggt tcacgctttc    1080
atcaaacgtt ctgacgctga agaagttgac ttcgctggtt ggctgtgctc taccatcggt    1140
ctgaaccagc cgtctacccc gacccacgct gctggtgtgg cagccgcagc tgcgcatcat    1200
caccaccatc actaa                                                    1215

<210> SEQ ID NO 32
<211> LENGTH: 36
<212> TYPE: DNA
```

<213> ORGANISM: Artificial Sequence
<220> FEATURE:
<223> OTHER INFORMATION: Synthetic Construct

<400> SEQUENCE: 32
ataagaatgc ggccgcgccg cagccgaacg accgag                            36

<210> SEQ ID NO 33
<211> LENGTH: 29
<212> TYPE: DNA
<213> ORGANISM: Artificial Sequence
<220> FEATURE:
<223> OTHER INFORMATION: Synthetic Construct

<400> SEQUENCE: 33
ctagctagcg tctgacgctc agtggaacg                                    29

<210> SEQ ID NO 34
<211> LENGTH: 27
<212> TYPE: DNA
<213> ORGANISM: Artificial Sequence
<220> FEATURE:
<223> OTHER INFORMATION: Synthetic Construct

<400> SEQUENCE: 34
ctagctagct cactcggtcg ctacgct                                      27

<210> SEQ ID NO 35
<211> LENGTH: 36
<212> TYPE: DNA
<213> ORGANISM: Artificial Sequence
<220> FEATURE:
<223> OTHER INFORMATION: Synthetic Construct

<400> SEQUENCE: 35
ataagaatgc ggccgctgaa atctagagcg gttcag                            36

<210> SEQ ID NO 36
<211> LENGTH: 34
<212> TYPE: DNA
<213> ORGANISM: Artificial Sequence
<220> FEATURE:
<223> OTHER INFORMATION: Synthetic Construct

<400> SEQUENCE: 36
aaaaggcgcc gccagcctag ccgggtcctc aacg                              34

<210> SEQ ID NO 37
<211> LENGTH: 26
<212> TYPE: DNA
<213> ORGANISM: Artificial Sequence
<220> FEATURE:
<223> OTHER INFORMATION: Synthetic Construct

<400> SEQUENCE: 37
aactgcagcc aatccggata tagttc                                       26

<210> SEQ ID NO 38
<211> LENGTH: 37
<212> TYPE: DNA
<213> ORGANISM: Artificial Sequence
<220> FEATURE:
<223> OTHER INFORMATION: Synthetic Construct

<400> SEQUENCE: 38
ggaattccat atgaccaaga ccccgccggc agcagtt                           37

<210> SEQ ID NO 39
<211> LENGTH: 24
<212> TYPE: DNA
<213> ORGANISM: Artificial Sequence
<220> FEATURE:
<223> OTHER INFORMATION: Synthetic Construct

<400> SEQUENCE: 39
aggcgcgcct tagtcctcca ctac                                            24

<210> SEQ ID NO 40
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (13)..(13)
<223> OTHER INFORMATION: PHOSPHORYLATION

<400> SEQUENCE: 40

Leu Cys Asp Phe Gly Val Ser Gly Gln Leu Ile Asp Ser Met Ala Asn
1               5                   10                  15

Ser Phe Val Gly Thr Arg
            20

<210> SEQ ID NO 41
<211> LENGTH: 72
<212> TYPE: DNA
<213> ORGANISM: Artificial Sequence
<220> FEATURE:
<223> OTHER INFORMATION: Synthetic Construct

<400> SEQUENCE: 41
gccggggtag tctaggggtt aggcagcgga ctgcagatcc gccttacgtg ggttcaaatc      60
ccacccccgg ct                                                         72

<210> SEQ ID NO 42
<211> LENGTH: 1650
<212> TYPE: DNA
<213> ORGANISM: Methanocaldococcus jannaschii

<400> SEQUENCE: 42
atgaaattaa acataaaag ggatgataaa atgagatttg atataaaaaa ggttttagag       60
ttagcagaga aggattttga cacggcatgg agagagacaa gggcattaat aaaggataaa    120
catattgaca ataaatatcc aagattaaag cctgtctatg aaagccaca tccagtgatg     180 gagacgatag agagattaag acaagcttat ctaagaatgg gatttgaaga gatgattaat    240
ccagttatcg ttgatgagat ggagatttat aagcaatttg gaccagaagc aatggcagtt    300
ttagatagat gtttttactt ggctggatta ccaaggccag atgttggttt aggaaatgag    360
aaggttgaga ttataaaaaa tttgggcata gatatagatg aggagaaaaa agagaggttg    420
agagaagttt tacatttata caaaaaagga gctatagatg gggatgattt agtctttgag    480
attgccaaag ctttaaatgt gagtaatgaa atgggattga aggttttaga aactgcattt    540
cctgaattta agatttgaa gccagaatca acaactctaa ctttaagaag ccacatgaca    600 tctggggtggt ttataactct aagcagttta ataagaaga gaaaactgcc tttaaagtta    660
ttctctatag atagatgttt tagaagggag caaagagagg atagaagcca tttaatgagt    720

```
tatcactctg catcttgtgt agttgttggt gaagatgtta gtgtagatga tggaaaggta     780
gttgctgaag gattgttggc tcaatttgga tttacaaaat ttaagtttaa gccagatgag     840
aaaaagagta agtattatac accagaaact caaacagagg tttatgccta tcatccaaag     900
ttgggagagt ggattgaagt agcaacccttt ggagtttatt caccaattgc attagctaaa    960
tataacatag atgtgccagt tatgaaccct ggcttaggag ttgagaggtt ggcaatgatt    1020
atttacggct atgaggatgt tagggcaatg gtttatcctc aatttttatga atacaggttg   1080 agtgatagag atatagctgg gatgataaga gttgataaag ttcctatatt ggatgaattc    1140
tacaactttg caaatgagct tattgatata tgcatagcaa ataaagataa ggaaagccca    1200
tgttcagttg aagttaaaag ggaattcaat ttcaatgggg agagaagagt aattaaagta    1260
gaaatatttg agaatgaacc aaataaaaag cttttaggtc cttctgtgtt aaatgaggtt    1320
tatgtctatg atggaaatat atatggcatt ccgccaacgt tgaaggggt taagaacag      1380 tatatcccaa ttttaaagaa agctaaggaa gaaggagttt ctacaaacat tagatacata    1440
gatgggatta tctataaatt agtagctaag attgaagagg ctttagtttc aaatgtggat    1500
gaatttaagt tcagagtccc aatagttaga agtttgagtg acataaacct aaaaattgat    1560
gaattggctt taaacagat aatggggag aataaggtta tagatgttag gggaccagtt     1620
ttcttaaatg caaaggttga gataaaatag                                    1650
```

<210> SEQ ID NO 43
<211> LENGTH: 549
<212> TYPE: PRT
<213> ORGANISM: Methanocaldococcus jannaschii

<400> SEQUENCE: 43

```
Met Lys Leu Lys His Lys Arg Asp Asp Lys Met Arg Phe Asp Ile Lys
 1               5                  10                  15

Lys Val Leu Glu Leu Ala Glu Lys Asp Phe Glu Thr Ala Trp Arg Glu
                20                  25                  30

Thr Arg Ala Leu Ile Lys Asp Lys His Ile Asp Asn Lys Tyr Pro Arg
            35                  40                  45

Leu Lys Pro Val Tyr Gly Lys Pro His Pro Val Met Glu Thr Ile Glu
        50                  55                  60

Arg Leu Arg Gln Ala Tyr Leu Arg Met Gly Phe Glu Glu Met Ile Asn
 65                  70                  75                  80

Pro Val Ile Val Asp Glu Met Glu Ile Tyr Lys Gln Phe Gly Pro Glu
                85                  90                  95

Ala Met Ala Val Leu Asp Arg Cys Phe Tyr Leu Ala Gly Leu Pro Arg
            100                 105                 110

Pro Asp Val Gly Leu Gly Asn Glu Lys Val Glu Ile Ile Lys Asn Leu
        115                 120                 125

Gly Ile Asp Ile Asp Glu Glu Lys Lys Glu Arg Leu Arg Glu Val Leu
    130                 135                 140

His Leu Tyr Lys Lys Gly Ala Ile Asp Gly Asp Asp Leu Val Phe Glu
145                 150                 155                 160

Ile Ala Lys Ala Leu Asn Val Ser Asn Glu Met Gly Leu Lys Val Leu
                165                 170                 175

Glu Thr Ala Phe Pro Glu Phe Lys Asp Leu Lys Pro Glu Ser Thr Thr
            180                 185                 190

Leu Thr Leu Arg Ser His Met Thr Ser Gly Trp Phe Ile Thr Leu Ser
        195                 200                 205
```

```
Ser Leu Ile Lys Lys Arg Lys Leu Pro Leu Lys Leu Phe Ser Ile Asp
    210                 215                 220
Arg Cys Phe Arg Arg Glu Gln Arg Glu Asp Arg Ser His Leu Met Ser
225                 230                 235                 240
Tyr His Ser Ala Ser Cys Val Val Gly Glu Asp Val Ser Val Asp
                245                 250                 255
Asp Gly Lys Val Val Ala Glu Gly Leu Leu Ala Gln Phe Gly Phe Thr
                260                 265                 270
Lys Phe Lys Phe Lys Pro Asp Glu Lys Lys Ser Lys Tyr Tyr Thr Pro
            275                 280                 285
Glu Thr Gln Thr Glu Val Tyr Ala Tyr His Pro Lys Leu Gly Glu Trp
        290                 295                 300
Ile Glu Val Ala Thr Phe Gly Val Tyr Ser Pro Ile Ala Leu Ala Lys
305                 310                 315                 320
Tyr Asn Ile Asp Val Pro Val Met Asn Leu Gly Leu Val Glu Arg
                325                 330                 335
Leu Ala Met Ile Ile Tyr Gly Tyr Glu Asp Val Arg Ala Met Val Tyr
                340                 345                 350
Pro Gln Phe Tyr Glu Tyr Arg Leu Ser Asp Arg Asp Ile Ala Gly Met
            355                 360                 365
Ile Arg Val Asp Lys Val Pro Ile Leu Asp Glu Phe Tyr Asn Phe Ala
370                 375                 380
Asn Glu Leu Ile Asp Ile Cys Ile Ala Asn Lys Asp Lys Glu Ser Pro
385                 390                 395                 400
Cys Ser Val Glu Val Lys Arg Glu Phe Asn Phe Asn Gly Glu Arg Arg
                405                 410                 415
Val Ile Lys Val Glu Ile Phe Glu Asn Glu Pro Asn Lys Lys Leu Leu
                420                 425                 430
Gly Pro Ser Val Leu Asn Glu Val Tyr Val Tyr Asp Gly Asn Ile Tyr
            435                 440                 445
Gly Ile Pro Pro Thr Phe Glu Gly Val Lys Glu Gln Tyr Ile Pro Ile
        450                 455                 460
Leu Lys Lys Ala Lys Glu Glu Gly Val Ser Thr Asn Ile Arg Tyr Ile
465                 470                 475                 480
Asp Gly Ile Ile Tyr Lys Leu Val Ala Lys Ile Glu Glu Ala Leu Val
                485                 490                 495
Ser Asn Val Asp Glu Phe Lys Phe Arg Val Pro Ile Val Arg Ser Leu
                500                 505                 510
Ser Asp Ile Asn Leu Lys Ile Asp Glu Leu Ala Leu Lys Gln Ile Met
            515                 520                 525
Gly Glu Asn Lys Val Ile Asp Val Arg Gly Pro Val Phe Leu Asn Ala
        530                 535                 540
Lys Val Glu Ile Lys
545

<210> SEQ ID NO 44
<211> LENGTH: 492
<212> TYPE: DNA
<213> ORGANISM: Artificial Sequence
<220> FEATURE:
<223> OTHER INFORMATION: Synthetic Construct

<400> SEQUENCE: 44
atggttctgt ctgaaggtga atggcagctg gttctgcacg tttgggctaa agttgaagct      60
gacgttgctg gtcacggtca ggacatcctg atccgtctgt tcaaatctca cccggaaacc     120
```

```
ctggaaaaat tcgaccgttt caaacacctg aaaaccgaag ctgaaatgaa ggcttctgaa    180
gacctgaaaa aacacggtgt taccgttctg accgctctgg gtgctatcct gaagaaaaag    240
ggtcaccacg aagctgaact gaaaccgctg gctcagtctc acgctaccaa acacaaaatc    300
ccgatcaaat acctggagtt catctctgaa gctatcatcc acgttctgca ctctcgtcat    360
ccgggtaact tcggtgctga cgctcagggt gctatgaaca aagctctgga actgttccgt    420
aaagacatcg ctgctaaata caagaactg gttaccagg gtggttctgg tcatcaccat    480
caccatcact aa                                                        492
```

\<210\> SEQ ID NO 45
\<211\> LENGTH: 1614
\<212\> TYPE: DNA
\<213\> ORGANISM: Methanococcus maripaludis

\<400\> SEQUENCE: 45

```
atgtttaaaa gagaagaaat cattgaaatg gccaataagg actttgaaaa agcatggatc     60
gaaactaaag accttataaa agctaaaaag ataaacgaaa gttacccaag aataaaacca    120 gttttttggaa aaacacaccc tgtaaatgac actattgaaa atttaagaca ggcatatctt    180
agaatgggtt ttgaagaata tataaaccca gtaattgtcg atgaaagaga tatttataaa    240
caattcggcc cagaagctat ggcagttttg atagatgct tttatttagc gggacttcca    300
agacctgacg ttggtttgag cgatgaaaaa atttcacaga ttgaaaaact tggaattaaa    360
gtttctgagc acaaagaaag tttacaaaaa atacttcacg gatacaaaaa aggaactctt    420
gatggtgacg atttagtttt agaaatttca aatgcacttg aaatttcaag cgagatgggt    480
ttaaaaattt tagaagatgt tttcccagaa tttaaggatt taaccgcagt tcttcaaaa    540 ttaactttaa gaagccacat gacttcagga tggttcctta ctgtttcaga cctcatgaac    600
aaaaaaccct tgccatttaa actcttttca atcgatagat gttttagaag agaacaaaaa    660
gaagataaaa gccacttaat gacataccac tctgcatcct gtgcaattgc aggtgaaggc    720
gtggatatta atgatggaaa agcaattgca gaaggattat tatcccaatt tggctttaca    780
aactttaaat tcattcctga tgaaagaaa agtaaatact acaccctga acacagact    840 gaagtttacg cataccaccc aaaattaaaa gaatggctcg aagttgctac atttggagta    900
tattcgccag ttgcattaag caaatacgga atagatgtac ctgtaatgaa tttgggtctt    960
ggtgttgaaa gacttgcaat gatttctgga aatttcgcag atgttcgaga atggtatat   1020 cctcagtttt acgaacacaa acttaatgac cggaatgtcg cttcaatggt aaaactcgat   1080
aaagttccag taatggatga aatttacgat ttaacaaaag aattaattga gtcatgtgtt   1140
aaaaacaaag atttaaaatc cccttgtgaa ttagctattg aaaaaacgtt ttcatttgga   1200
aaaaccaaga aaatgtaaa aataaacatt tttgaaaag aagaaggtaa aaatttactc   1260
ggaccttcaa ttttaaacga atctacgtt tacgatggaa atgtaattgg aattcctgaa   1320
agctttgacg gagtaaaaga agaatttaaa gacttcttag aaaaaggaaa atcagaaggg   1380
gtagcaacag gcattcgata tatcgatgcg ctttgcttta aaattacttc aaaattagaa   1440
gaagcatttg tgtcaaacac tactgaattc aaagttaaag ttccaattgt cagaagttta   1500
agcgacatta acttaaaaat cgatgatatc gcattaaaac agatcatgag caaaaataaa   1560
gtaatcgacg ttagaggccc agtcttttta aatgtcgaag taaaaattga ataa          1614
```

\<210\> SEQ ID NO 46

<211> LENGTH: 537
<212> TYPE: PRT
<213> ORGANISM: Methanococcus maripaludis

<400> SEQUENCE: 46

| | | | | | | | | | | | | | | | |
|---|---|---|---|---|---|---|---|---|---|---|---|---|---|---|---|
| Met | Phe | Lys | Arg | Glu | Glu | Ile | Ile | Glu | Met | Ala | Asn | Lys | Asp | Phe | Glu |
| 1 | | | | 5 | | | | | 10 | | | | | 15 | |
| Lys | Ala | Trp | Ile | Glu | Thr | Lys | Asp | Leu | Ile | Lys | Ala | Lys | Lys | Ile | Asn |
| | | | 20 | | | | | 25 | | | | | 30 | | |
| Glu | Ser | Tyr | Pro | Arg | Ile | Lys | Pro | Val | Phe | Gly | Lys | Thr | His | Pro | Val |
| | | | 35 | | | | | 40 | | | | | 45 | | |
| Asn | Asp | Thr | Ile | Glu | Asn | Leu | Arg | Gln | Ala | Tyr | Leu | Arg | Met | Gly | Phe |
| | 50 | | | | | 55 | | | | | 60 | | | | |
| Glu | Glu | Tyr | Ile | Asn | Pro | Val | Ile | Val | Asp | Glu | Arg | Asp | Ile | Tyr | Lys |
| 65 | | | | | 70 | | | | | 75 | | | | | 80 |
| Gln | Phe | Gly | Pro | Glu | Ala | Met | Ala | Val | Leu | Asp | Arg | Cys | Phe | Tyr | Leu |
| | | | | 85 | | | | | 90 | | | | | 95 | |
| Ala | Gly | Leu | Pro | Arg | Pro | Asp | Val | Gly | Leu | Ser | Asp | Glu | Lys | Ile | Ser |
| | | | 100 | | | | | 105 | | | | | 110 | | |
| Gln | Ile | Glu | Lys | Leu | Gly | Ile | Lys | Val | Ser | Glu | His | Lys | Glu | Ser | Leu |
| | | | 115 | | | | | 120 | | | | | 125 | | |
| Gln | Lys | Ile | Leu | His | Gly | Tyr | Lys | Lys | Gly | Thr | Leu | Asp | Gly | Asp | Asp |
| | 130 | | | | | 135 | | | | | 140 | | | | |
| Leu | Val | Leu | Glu | Ile | Ser | Asn | Ala | Leu | Glu | Ile | Ser | Ser | Glu | Met | Gly |
| 145 | | | | | 150 | | | | | 155 | | | | | 160 |
| Leu | Lys | Ile | Leu | Glu | Asp | Val | Phe | Pro | Glu | Phe | Lys | Asp | Leu | Thr | Ala |
| | | | | 165 | | | | | 170 | | | | | 175 | |
| Val | Ser | Ser | Lys | Leu | Thr | Leu | Arg | Ser | His | Met | Thr | Ser | Gly | Trp | Phe |
| | | | 180 | | | | | 185 | | | | | 190 | | |
| Leu | Thr | Val | Ser | Asp | Leu | Met | Asn | Lys | Lys | Pro | Leu | Pro | Phe | Lys | Leu |
| | | | 195 | | | | | 200 | | | | | 205 | | |
| Phe | Ser | Ile | Asp | Arg | Cys | Phe | Arg | Arg | Glu | Gln | Lys | Glu | Asp | Lys | Ser |
| | 210 | | | | | 215 | | | | | 220 | | | | |
| His | Leu | Met | Thr | Tyr | His | Ser | Ala | Ser | Cys | Ala | Ile | Ala | Gly | Glu | Gly |
| 225 | | | | | 230 | | | | | 235 | | | | | 240 |
| Val | Asp | Ile | Asn | Asp | Gly | Lys | Ala | Ile | Ala | Glu | Gly | Leu | Leu | Ser | Gln |
| | | | | 245 | | | | | 250 | | | | | 255 | |
| Phe | Gly | Phe | Thr | Asn | Phe | Lys | Phe | Ile | Pro | Asp | Glu | Lys | Lys | Ser | Lys |
| | | | 260 | | | | | 265 | | | | | 270 | | |
| Tyr | Tyr | Thr | Pro | Glu | Thr | Gln | Thr | Glu | Val | Tyr | Ala | Tyr | His | Pro | Lys |
| | | | 275 | | | | | 280 | | | | | 285 | | |
| Leu | Lys | Glu | Trp | Leu | Glu | Val | Ala | Thr | Phe | Gly | Val | Tyr | Ser | Pro | Val |
| | 290 | | | | | 295 | | | | | 300 | | | | |
| Ala | Leu | Ser | Lys | Tyr | Gly | Ile | Asp | Val | Pro | Val | Met | Asn | Leu | Gly | Leu |
| 305 | | | | | 310 | | | | | 315 | | | | | 320 |
| Gly | Val | Glu | Arg | Leu | Ala | Met | Ile | Ser | Gly | Asn | Phe | Ala | Asp | Val | Arg |
| | | | | 325 | | | | | 330 | | | | | 335 | |
| Glu | Met | Val | Tyr | Pro | Gln | Phe | Tyr | Glu | His | Lys | Leu | Asn | Asp | Arg | Asn |
| | | | 340 | | | | | 345 | | | | | 350 | | |
| Val | Ala | Ser | Met | Val | Lys | Leu | Asp | Lys | Val | Pro | Val | Met | Asp | Glu | Ile |
| | | | 355 | | | | | 360 | | | | | 365 | | |
| Tyr | Asp | Leu | Thr | Lys | Glu | Leu | Ile | Glu | Ser | Cys | Val | Lys | Asn | Lys | Asp |
| | 370 | | | | | 375 | | | | | 380 | | | | |
| Leu | Lys | Ser | Pro | Cys | Glu | Leu | Ala | Ile | Glu | Lys | Thr | Phe | Ser | Phe | Gly |

```
385                 390                 395                 400
Lys Thr Lys Lys Asn Val Lys Ile Asn Ile Phe Glu Lys Glu Glu Gly
                405                 410                 415

Lys Asn Leu Leu Gly Pro Ser Ile Leu Asn Glu Ile Tyr Val Tyr Asp
                420                 425                 430

Gly Asn Val Ile Gly Ile Pro Glu Ser Phe Asp Gly Val Lys Glu Glu
                435                 440                 445

Phe Lys Asp Phe Leu Glu Lys Gly Lys Ser Glu Gly Val Ala Thr Gly
    450                 455                 460

Ile Arg Tyr Ile Asp Ala Leu Cys Phe Lys Ile Thr Ser Lys Leu Glu
465                 470                 475                 480

Glu Ala Phe Val Ser Asn Thr Thr Glu Phe Lys Val Lys Val Pro Ile
                485                 490                 495

Val Arg Ser Leu Ser Asp Ile Asn Leu Lys Ile Asp Asp Ile Ala Leu
                500                 505                 510

Lys Gln Ile Met Ser Lys Asn Lys Val Ile Asp Val Arg Gly Pro Val
                515                 520                 525

Phe Leu Asn Val Glu Val Lys Ile Glu
    530                 535
```

SITE-SPECIFIC INCORPORATION OF PHOSPHOSERINE INTO PROTEINS IN ESCHERICHIA COLI

CROSS REFERENCE TO RELATED APPLICATIONS

This application is a continuation of pending application Ser. No. 13/877,628, filed Apr. 3, 2013, which is a 371 of International Application No. PCT/US2011/055414, filed Oct. 7, 2011, which claims benefit of U.S. Provisional Application No. 61/390,853, filed on Oct. 7, 2010, and U.S. Provisional Application No. 61/470,332, filed on Mar. 31, 2011.

STATEMENT REGARDING FEDERALLY SPONSORED RESEARCH OR DEVELOPMENT

This invention was made with Government Support under Agreement R01 GM022854 awarded by the National Institutes of Health and Agreement 0654283 awarded by the National Science Foundation. The Government has certain rights in the invention.

REFERENCE TO SEQUENCE LISTING

The Sequence Listing submitted as a text file named "YU_5254_PCT_ST25.txt," created on Sep. 22, 2011, and having a size of 44,989 bytes is hereby incorporated by reference pursuant to 37 C.F.R. §1.52(e)(5).

FIELD OF THE INVENTION

The field of the present invention generally relates to methods for the site specific phosphorylation of proteins in vitro and in vivo.

BACKGROUND OF THE INVENTION

Signal transduction is any process by which a cell converts one kind of signal or stimulus into another. Processes referred to as signal transduction often involve a sequence of biochemical reactions inside the cell, which are carried out by enzymes and linked through second messengers. Signal transduction is often accomplished by the activation of enzymes that can act upon other enzymes and change their catalytic activity. This may lead to increases or decreases in the activity of certain metabolic pathways, or may lead to even large intracellular changes, for example, the initiation of specific patterns of gene expression and/or changes in cell proliferation.

The most common covalent modification used in signal transduction processes is phosphorylation, which results in the alteration of the activity of those enzymes which become phosphorylated. Phosphorylation is the addition of a phosphate ($PO_4$) group to a protein or a small molecule. Any of several amino acids in a protein may be phosphorylated. Phosphorylation on serine is the most common, followed by threonine. Tyrosine phosphorylation is relatively rare. However, since tyrosine phosphorylated proteins are relatively easy to purify using antibodies, tyrosine phosphorylation sites are relatively well understood. Histidine and aspartate phosphorylation occurs in prokaryotes as part of two-component signaling. Other types of phosphorylation include oxidative phosphorylation. Adenosine triphosphate (ATP), the "high-energy" exchange medium in the cell, is synthesized in the mitochondrion by addition of a third phosphate group to Adenosine diphosphate (ADP) in a process referred to as oxidative phosphorylation. ATP is also synthesized by substrate level phosphorylation during glycolysis. ATP is synthesized at the expense of solar energy by photophosphorylation in the chloroplasts of plant cells.

In eukaryotes, protein phosphorylation is probably the most important regulatory event. Many enzymes and receptors are switched "on" or "off" by phosphorylation and dephosphorylation. Phosphorylation is catalyzed by enzymes known as ATP-dependent phosphotransferases which are often simply referred to as "kinases." These include, among others, protein kinases, lipid kinases, inositol kinases, non-classical protein kinases, histidine kinases, aspartyl kinases, nucleoside kinases, and polynucleotide kinases.

Phosphorylation regulates protein function, for example, by affecting conformation. This in turn regulates such processes as enzyme activity, protein-protein interactions, subcellular distribution, and stability and degradation. The stoichiometry of phosphorylation of a given site is controlled by the relative activities of a cell's repertoire of protein kinases and phosphatases. Thus phosphorylation can often generate extremely rapid and reversible changes in the activity of target proteins. The ability to assay the state of phosphorylation of specific proteins is of great utility in the quest to establish the function of a given protein. Such assays are also critical for the identification of drugs that can influence the phosphorylation, and hence the function, of specific proteins.

In general, phosphoproteins are highly unstable and difficult to produce, both in terms of specific phosphorylation of biologically relevant amino acids and subsequent purification of protein. A means to specify and drive a targeted phosphorylation event with a high degree of certainty and efficiency is needed. This is particularly important for recombinant proteins expressed in bacterial or fungal expression systems which do not phosphorylate proteins in the same way as mammalian cells.

Therefore, it is an object of the present invention to provide a method for the site specific phosphorylation of proteins.

It is further an object of the present invention to provide a method for the site specific phosphorylation of proteins in vivo.

In particular, it is an object of the present invention to provide a method for the site specific incorporation of phosphoserine into a protein.

SUMMARY OF THE INVENTION

Mutant elongation factor proteins (EF-Sep) are described for use with phosphoseryl-tRNA synthetase (SepRS) and phosphoseryl-tRNA (tRNA$^{Sep}$) in site specific incorporation of phosphoserine into a protein or polypeptide. Typically, SepRS preferentially aminoacylates tRNA$^{Sep}$ with O-phosphoserine and the tRNA$^{Sep}$ recognizes at least one codon such as a stop codon. Due to the negative charge of the phosphoserine, Sep-tRNA$^{Sep}$ does not bind elongation factor Tu (EF-Tu). However, the disclosed EF-Sep proteins can bind Sep-tRNA$^{Sep}$ and protect Sep-tRNA$^{Sep}$ from deacylation and catalyze the covalent transfer of the phosphoserine amino acid onto the polypeptide.

In some embodiments, EF-Sep is a mutant form of bacterial EF-Tu having a mutation at one or more amino acid residues corresponding to His67, Glu216, Asp217, Phe219, Thr229, and Asn274 in E. coli EF-Tu, which are located in the amino acid binding pocket for aminoacylated tRNA. In some embodiments, EF-Sep is a mutant form of eukaryotic elongation factor 1A (eEF1A) with mutations in positions equivalent to bacterial counterpart. In preferred embodiments, the EF-Sep has the amino acid sequence SEQ ID NO:1, SEQ ID NO:2, SEQ ID NO:3, SEQ ID NO:4, or a conservative variant thereof. Nucleic acids encoding EF-Sep are also disclosed. For example, in some embodiments, the nucleic acid sequence encoding EF-Sep has the nucleic acid sequence SEQ ID NO:5, SEQ ID NO:6, SEQ ID NO:7, SEQ ID NO:8, or a conservative variant thereof.

In a preferred embodiment, "tRNA$^{Sep}$" and "SepRS" refer to the cysteinyl-tRNA from *Methanocaldococcus jannaschii* and the phosphoseryl-tRNA synthetase from *Methanococcus maripaludis*, respectively and variants thereof having conservative substitutions, additions, and/or deletions therein not affecting the structure or function. Typically, SepRS preferentially aminoacylates tRNA$^{Sep}$ with O-phosphoserine and the tRNA$^{Sep}$ recognizes at least one codon. In a preferred embodiment, the tRNA$^{Sep}$ recognizes a stop codon or an unconventional or non-native codon.

Methods for producing target proteins that contain at least one phosphoserine are described. The method results in proteins that have a phosphoserine incorporated into a protein in a manner indistinguishable from the phosphorylation of a serine by a kinase. Nucleic acids encoding genes with SepRS and tRNA$^{Sep}$ activity are provided, preferably on vectors, such as cloning vectors and expression vectors. These vectors can be in the form of a plasmid, a bacterium, a virus, a naked polynucleotide, or a conjugated polynucleotide. In one embodiment, the vectors are expressed in cells such as bacterial cells (e.g., *Escherichia coli*), archeaebacterial cells, and eukaryotic cells (e.g., yeast cells, mammalian cells, plant cells, insect cells, fungal cells). The cells preferably lack a protein with Sep-tRNA:Cys-tRNA synthase (SepCysS) activity that converts tRNA-bound phosphoserine to cysteine. In an alternative embodiment, the vectors are expressed in an in vitro transcription/translation system. In this embodiment the vectors are transcribed and translated prior to or along with nucleic acids encoding one or more proteins or polypeptides.

In some embodiments, the target protein containing phosphoserine is produced and modified in a cell-dependent manner. This provides for the production of proteins that are stably folded, glycosylated, or otherwise modified by the cell.

Kits for producing polypeptides and/or proteins containing phosphoserine are also provided.

The proteins or polypeptides containing phosphoserine and antibodies to such polypeptides or proteins have a variety of uses including the study of kinases, phosphotases, and target proteins in signal transduction pathways, antibody production, protein array manufacture and development of cell-based screens for new drug discovery and the development of therapeutic agents, agricultural products, or peptide-based libraries such as phage display libraries.

DETAILED DESCRIPTION OF THE INVENTION

I. Definitions

Figure 1A:
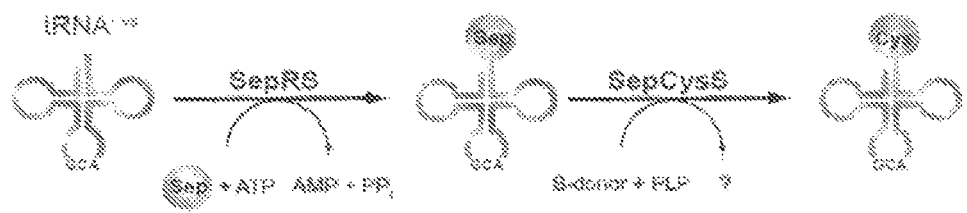
FIG. 1A is a diagram showing the indirect pathway for the synthesis of Cys-tRNA$^{Cys}$ in methanogenic archaea.

The term "transfer RNA (tRNA)" refers to a set of genetically encoded RNAs that act during protein synthesis as adaptor molecules, matching individual amino acids to their corresponding codon on a messenger RNA (mRNA). In higher eukaryotes such as mammals, there is at least one tRNA for each of the 20 naturally occurring amino acids. The 3' end of a tRNA is aminoacylated by a tRNA synthetase so that an amino acid is attached to the 3'end of the tRNA. This amino acid is delivered to a growing polypeptide chain as the anticodon sequence of the tRNA reads a codon triplet in an mRNA.

The term "aminoacyl tRNA synthetase (AARS)" refers to an enzyme that catalyzes the esterification of a specific amino acid or its precursor to one of all its compatible cognate tRNAs to form an aminoacyl-tRNA. These charged aminoacyl tRNAs then participate in mRNA translation and protein synthesis. The AARS show high specificity for charging a specific tRNA with the appropriate amino acid. In general, there is at least one AARS for each of the twenty amino acids.

The term "tRNA$^{Sep}$" refers to a tRNA that can be aminoacylated with O-phosphoserine (Sep) and recognize at least one codon such that the phosphoserine is incorporated into a protein or polypeptide. In some embodiments, the tRNA$^{Sep}$ is a tRNA$^{Cys}$ from *Methanocaldococcus jannaschii* containing a C20U mutation that improves aminoacylation by SepRS without affecting CysRS recognition. In some embodiments, the tRNA$^{Sep}$ contains an anticodon that binds a stop codon.

The term "Sep-tRNA$^{Sep}$" refers to a tRNA$^{Sep}$ that has been aminoacylated with O-phosphoserine (Sep).

The term "O-phosphoseryl-tRNA synthetase (SepRS)" refers to an O-phosphoseryl-tRNA synthetase that preferentially aminoacylates tRNA$^{Sep}$ with O-phosphoserine (Sep) to form Sep-tRNA$^{Sep}$.

The term "EF-Sep" refers to a mutant elongation factor protein that binds Sep-tRNA$^{Sep}$ and catalyzes the covalent transfer of the phosphoserine amino acid onto the polypeptide. Due to the negative charge of the phosphoserine, Sep-tRNA$^{Sep}$ does not bind elongation factor Tu (EF-Tu). EF-Sep proteins can bind Sep-tRNA$^{Sep}$, protect Sep-tRNA$^{Sep}$ from deacylation, and catalyze the covalent transfer of the phosphoserine amino acid onto the polypeptide.

As used herein "suppressor tRNA" refers to a tRNA that alters the reading of a messenger RNA (mRNA) in a given translation system. For example, a suppressor tRNA can read through a stop codon.

The term "anticodon" refers to a unit made up of three nucleotides that correspond to the three bases of a codon on the mRNA. Each tRNA contains a specific anticodon triplet sequence that can base-pair to one or more codons for an amino acid or "stop codon." Known stop codons include but are not limited to, the three codon bases UAA (known as ochre), UAG (known as amber), and UGA (known as opal), which do not code for an amino acid but act as signals for the termination of protein synthesis.

The term "protein" "polypeptide" or "peptide" refers to a natural or synthetic molecule comprising two or more amino acids linked by the carboxyl group of one amino acid to the alpha amino group of another.

The term "residue" as used herein refers to an amino acid that is incorporated into a protein. The amino acid may be a naturally occurring amino acid and, unless otherwise limited, may encompass known analogs of natural amino acids that can function in a similar manner as naturally occurring amino, acids.

The term "polynucleotide" or "nucleic acid sequence" refers to a natural or synthetic molecule comprising two or more nucleotides linked by a phosphate group at the 3' position of one nucleotide to the 5' end of another nucleotide. The polynucleotide is not limited by length, and thus the polynucleotide can include deoxyribonucleic acid (DNA) or ribonucleic acid (RNA).

The term "gene" refers to a polynucleotide that encodes a protein or functional RNA molecule.

The term "vector" or "construct" refers to a polynucleotide capable of transporting into a cell another polynucleotide to which the vector sequence has been linked. The term "expression vector" includes any vector, (e.g., a plasmid, cosmid or phage chromosome) containing a gene construct in a form suitable for expression by a cell (e.g., linked to a transcriptional control element). "Plasmid" and "vector" are used interchangeably, as a plasmid is a commonly used form of vector.

The term "operatively linked to" refers to the functional relationship of a nucleic acid with another nucleic acid sequence. Promoters, enhancers, transcriptional and translational stop sites, and other signal sequences are examples of nucleic acid sequences operatively linked to other sequences. For example, operative linkage of gene to a transcriptional control element refers to the physical and functional relationship between the gene and promoter such that the transcription of the gene is initiated from the promoter by an RNA polymerase that specifically recognizes, binds to and transcribes the DNA.

The terms "transformation" and "transfection" refer to the introduction of a polynucleotide, e.g., an expression vector, into a recipient cell including introduction of a polynucleotide to the chromosomal DNA of the cell.

The term "variant" refers to an amino acid or nucleic acid sequence having conservative substitutions, non-conservative substitutions (i.e. a degenerate variant), substitutions within the wobble position of a codon encoding an amino acid, amino acids added to the C-terminus of a peptide, or a peptide having 60%, 70%, 80%, 90%, 95%, 96%, 97%, 98%, or 99% sequence identity to an amino acid sequence.

The term "conservative variant" refers to a particular nucleic acid sequence that encodes identical or essentially identical amino acid sequences. Conservative substitution tables providing functionally similar amino acids are well known in the art. The following sets forth exemplary groups which contain natural amino acids that are "conservative substitutions" for one another. Conservative Substitution Groups 1 Alanine (A) Serine (S) Threonine (T); 2 Aspartic acid (D) Glutamic acid (E); 3 Asparagine (N) Glutamine (Q); 4 Arginine (R) Lysine (K); 5 Isoleucine (I) Leucine (L) Methionine (M) Valine (V); and 6 Phenylalanine (F) Tyrosine (Y) Tryptophan (W).

The term "percent (%) sequence identity" or "homology" refers to the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

The term "translation system" refers to the components necessary to incorporate an amino acid into a growing polypeptide chain (protein). Components of a translation system generally include amino acids, ribosomes, tRNAs, synthetases, and mRNA. The components described herein can be added to a translation system, in vivo or in vitro, to incorporate phosphoserine into a protein.

The term "transgenic organism" refers to any organism, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. Suitable transgenic organisms include, but are not limited to, bacteria, cyanobacteria, fungi, plants and animals. The nucleic acids described herein can be introduced into the host by methods known in the art, for example infection, transfection, transformation or transconjugation.

The term "eukaryote" or "eukaryotic" refers to organisms or cells or tissues derived from these organisms belonging to the phylogenetic domain Eukarya such as animals (e.g., mammals, insects, reptiles, and birds), ciliates, plants (e.g., monocots, dicots, and algae), fungi, yeasts, *flagellates*, microsporidia, and protists.

The term "prokaryote" or "prokaryotic" refers to organisms including, but not limited to, organisms of the Eubacteria phylogenetic domain, such as *Escherichia coli, Thermus thermophilus,* and *Bacillus stearothermophilus,* or organisms of the Archaea phylogenetic domain such as, *Methanococcus jannaschii, Methanobacterium thermoauto-* trophicum, Halobacterium such as *Haloferax volcanii* and *Halobacterium* species NRC-1, *Archaeoglobus fulgidus*, *Pyrococcus furiosus*, *Pyrococcus horikoshii*, and *Aeuropyrum pernix*.

II. Compositions

A. Aminoacyl-tRNA Synthetases

A tRNA that can be aminoacylated with O-phosphoserine ("tRNA$^{Sep}$") is disclosed for use in incorporating phosphoserine into a protein. The tRNA$^{Sep}$ recognizes at least one codon in the mRNA for the protein such that a phosphoserine can incorporated into the protein. For example, the tRNA$^{Sep}$ can contain an anticodon that binds a stop codon or an unconventional or non-native codon. In some embodiments, the tRNA$^{Sep}$ is a tRNA$^{Cys}$ from an achaea, such as *Methanocaldococcus jannaschii* or *Methanococcus maripaludis*. tRNA$^{Cys}$ is also found in *Methanopyrus kandleri*, *Methanococcoides burtonii*, *Methanospirillum hungatei*, *Methanocorpusculum labreanum*, *Methanoregula boonei*, *Methanococcus aeolicus*, *Methanococcus vannieli*, *Methanosarcina mazei*, *Methanosarcina barkeri*, *Methanosarcina acetivorans*, *Methanosaeta thermophila*, *Methanoculleus marisnigri*, *Methanocaldococcus vulcanius*, *Methanocaldococcus fervens*, and *Methanosphaerula palustris*. In preferred embodiments, the tRNA$^{Sep}$ contains a mutation (e.g., C20U mutation) that improves aminoacylation by SepRS without affecting CysRS recognition. In particularly preferred embodiments, the tRNA$^{Sep}$ is encoded by the nucleic acid sequence SEQ ID NO:41, or a conservative variant thereof.

tRNA$^{Sep}$ from *Methanocaldococcus jannaschii* (FIG. 1B):

```
                                      (SEQ ID NO: 41)
GCCGGGGTAGTCTAGGGGTTAGGCAGCGGACTGCAGATCCGCCTT

ACGTGGGTTCAAATCCCACCCCCGGCT
```

A phosphoseryl-tRNA synthetase (SepRS) that preferentially aminoacylates tRNA$^{Sep}$ with phosphoserine is also disclosed for use in incorporating phosphoserine into a protein. In some embodiments, the SepRS is a phosphoseryl-tRNA synthetase from an achaea, such as *Methanococcus maripaludis* or *Methanocaldococcus jannaschii*. SepRS is also found in *Methanopyrus kandleri*, *Methanococcoides burtonii*, *Methanospirillum hungatei*, *Methanocorpusculum labreanum*, *Methanoregula boonei*, *Methanococcus aeolicus*, *Methanococcus vannieli*, *Methanosarcina mazei*, *Methanosarcina barkeri*, *Methanosarcina acetivorans*, *Methanosaeta thermophila*, *Methanoculleus marisnigri*, *Methanocaldococcus vulcanius*, *Methanocaldococcus fervens*, and *Methanosphaerula palustris*.

In particularly preferred embodiments, the SepRS has the amino acid sequence SEQ ID NO:43 or 46, or a conservative variant thereof. For example, the SepRS can be encoded by the nucleic acid sequence SEQ ID NO:42 or 45, or a variant thereof.

SepRS from *Methanocaldococcus jannaschii*:

```
                                      (SEQ ID NO: 42)
ATGAAATTAAAACATAAAAGGGATGATAAAATGAGATTTG

ATATAAAAAGGTTTTAGAGTTAGCAGAGAAGGATTTTGAGACG

GCATGGAGAGACAAGGGCATTAATAAAGGATAAACATATTGA

CAATAAATATCCAAGATTAAAGCCTGTCTATGGAAAGCCACATCC

AGTGATGGAGACGATAGAGAGATTAAGACAAGCTTATCTAAGAA

TGGGATTTGAAGAGATGATTAATCCAGTTATCGTTGATGAGATGG

AGATTTATAAGCAATTTGGACCAGAGCAATGGCAGTTTTAGATA

GATGTTTTTACTTGGCTGGATTACCAAGGCCAGATGTTGGTTTAGG

AAATGAGAAGGTTGAGATTATAAAAAATTTGGGCATAGATATAG

ATGAGGAGAAAAAAGAGAGGTTGAGAGAAGTTTTACATTTATAC

AAAAAAGGAGCTATAGATGGGGATGATTTAGTCTTTGAGATTGCC

AAAGCTTTAAATGTGAGTAATGAAATGGGATTGAAGGTTTTAGAA

ACTGCATTTCCTGAATTTAAAGATTTGAAGCCAGAATCAACAACT

CTAACTTTAAGAAGCCACATGACATCTGGGTGGTTTATAACTCTA

AGCAGTTTAATAAAGAAGAGAAAACTGCCTTTAAAGTTATTCTCT

ATAGATAGATGTTTTAGAAGGGAGCAAAGAGAGGATAGAAGCCA

TTTAATGAGTTATCACTCTGCATCTTGTGTAGTTGTTGGTGAAGAT

GTTAGTGTAGATGATGGAAAGGTAGTTGCTGAAGGATTGTTGGCT

CAATTTGGATTTACAAAATTTAAGTTTAAGCCAGATGAGAAAAAG

AGTAAGTATTATACACCAGAAACTCAAACAGAGGTTTATGCCTAT

CATCCAAAGTTGGGAGAGTGGATTGAAGTAGCAACCTTTGGAGTT

TATTCACCAATTGCATTAGCTAAATATAACATAGATGTGCCAGTT

ATGAACCTTGGCTTAGGAGTTGAGAGGTTGGCAATGATTATTTAC

GGCTATGAGGATGTTAGGGCAATGGTTTATCCTCAATTTTATGAA

TACAGGTTGAGTGATAGAGATATAGCTGGGATGATAAGAGTTGAT

AAAGTTCCTATATTGGATGAATTCTACAACTTTGCAAATGAGCTT

ATTGATATATGCATAGCAAATAAAGATAAGGAAAGCCCATGTTCA

GTTGAAGTTAAAAGGGAATTCAATTTCAATGGGGAGAGAAGAGT

AATTAAAGTAGAAATATTTGAGAATGAACCAAATAAAAAGCTTTT

AGGTCCTTCTGTGTTAAATGAGGTTTATGTCTATGATGGAAATATA

TATGGCATTCCGCCAACGTTTGAAGGGGTTAAAGAACAGTATATC

CCAATTTTAAAGAAAGCTAAGGAAGAAGGAGTTTCTACAAACATT

AGATACATAGATGGGATTATCTATAAATTAGTAGCTAAGATTGAA

GAGGCTTTAGTTTCAAATGTGGATGAATTTAAGTTCAGAGTCCCA

ATAGTTAGAAGTTTGAGTGACATAAACCTAAAAATTGATGAATTG

GCTTTAAAACAGATAATGGGGGAGAATAAGGTTATAGATGTTAG

GGGACCAGTTTTCTTAAATGCAAAGGTTGAGATAAAATAG;

(SEQ ID NO: 43)
MKLKHKRDDKMRFDIKKVLELAEKDFETAWRETRALIKDKH

IDNKYPRLKPVYGKPHPVMETIERLRQAYLRMGFEEMINPVIVDEME

IYKQFGPEAMAVLDRCFYLAGLPRPDVGLGNEKVEIIKNLGIDIDEEK

KERLREVLHLYKKGAIDGDDLVFEIAKALNVSNEMGLKVLETAFPEF

KDLKPESTTLTLRSHMTSGWFITLSSLIKKRKLPLKLFSIDRCFRREQR

EDRSHLMSYHSASCVVVGEDVSVDDGKVVAEGLLAQFGFTKFKFKP
```

-continued

DEKKSKYYPETQTEVYAYHPKLGEWIEVATFGVYSPIALAKYNIDV

PVMNLGLGVERLAMIIYGYEDVRAMVYPQFYEYRLSDRDIAGMIRV

DKVPILDEFYNFANELIDIDIANKDKESPCSVEVKREFNFNGERRVIKV

EIFENEPNKKLLGPSVLNEVYVYDGNIYGIPPTFEGVKEQYIPILKKAK

EEGVSTNIRYIDGIIYKLVAKIEEALVSNVDEFKFRVPIVRSLSDINLKI

DELALKQIMGENKVIDVRGPVFLNAKVEIK.

SepRS from *Methanococcus maripaludis*:

(SEQ ID NO: 45)
ATGTTTAAAAGAGAAGAAATCATTGAAATGGCCAATAAGG

ACTTTGAAAAAGCATGGATCGAAACTAAAGACCTTATAAAAGCTA

AAAAGATAAACGAAAGTTACCCAAGAATAAAACCAGTTTTTGGA

AAAACACACCCTGTAAATGACACTATTGAAAATTTAAGACAGGCA

TATCTTAGAATGGGTTTTGAAGAATATATAAACCCAGTAATTGTC

GATGAAAGATATTTATAAACAATTCGGCCCAGAAGCTATGGCA

GTTTTGGATAGATGCTTTTATTTAGCGGGACTTCCAAGACCTGACG

TTGGTTTGAGCGATGAAAAAATTTCACAGATTGAAAAACTTGGAA

TTAAAGTTTCTGAGCACAAAGAAAGTTTACAAAAAATACTTCACG

GATACAAAAAAGGAACTCTTGATGGTGACGATTTAGTTTTAGAAA

TTTCAAATGCACTTGAAATTTCAAGCGAGATGGGTTTAAAAATTT

TAGAAGATGTTTTCCCAGAATTTAAGGATTTAACCGCAGTTTCTTC

AAAATTAACTTTAAGAAGCCACATGACTTCAGGATGGTTCCTTAC

TGTTTCAGACCTCATGAACAAAAAACCCTTGCCATTTAAACTCTTT

TCAATCGATAGATGTTTTAGAAGAGAACAAAAAGAAGATAAAAG

CCACTTAATGACATACCACTCTGCATCCTGTGCAATTGCAGGTGA

AGGCGTGGATATTAATGATGGAAAAGCAATTGCAGAAGGATTATT

ATCCCAATTTGGCTTTACAAACTTTAAATTCATTCCTGATGAAAAG

AAAAAGTAAATACTACACCCCTGAAACACAGACTGAAGTTTACGCA

TACCACCCAAAATTAAAAGAATGGCTCGAAGTTGCTACATTTGGA

GTATATTCGCCAGTTGCATTAAGCAAATACGGAATAGATGTACCT

GTAATGAATTTGGGTCTTGGTGTTGAAAGACTTGCAATGATTTCTG

GAAATTTCGCAGATGTTCGAGAAATGGTATATCCTCAGTTTTACG

AACACAAACTTAATGACCGGAATGTCGCTTCAATGGTAAAACTCT

ATAAAGTTCCAGTAATGGATGAAATTTACGATTTAACAAAAGAAT

TAATTGAGTCATGTGTTAAAACAAAGATTTAAAATCCCCTTGTG

AATTAGCTATTGAAAAAACGTTTTCATTTGGAAAAACCAAGAAAA

ATGTAAAAATAAACATTTTTGAAAAAGAAGAAGGTAAAAATTTA

CTCGGACCTTCAATTTTAAACGAAATCTACGTTTACGATGGAAAT

GTAATTGGAATTCCTGAAAGCTTTGACGGAGTAAAAGAAGAATTT

AAAGACTTCTTAGAAAAAGGAAAATCAGAAGGGGTAGCAACAGG

CATTCGATATATCGATGCGCTTTGCTTTAAAATTACTTCAAAATTA

-continued

GAAGAAGCATTTGTGTCAAACACTACTGAATTCAAAGTTAAAGTT

CCAATTGTCAGAAGTTTAAGCGACATTAACTTAAAAATCGATGAT

ATCGCATTAAAACAGATCATGAGCAAAAATAAAGTAATCGACGTT

AGAGGCCCAGTCTTTTTAAATGTCGAAGTAAAAATTGAATAA;

(SEQ ID NO: 46)
MFKREEIIEMANKDFEKAWIETKDLIKAKKINESYPRIKPVFGK

THPVNDTIENLRQAYLRMGFEEYINPVIVDERDIYKQFGPEAMAVLD

RCFYLAGLPRPDVGLSDEKISQIEKLGIKVSEHKESLQKILHGYKKGT

LDGDDLVLEISNALEISSEMGLKILEDVFPEFKDLTAVSSKLTLRSHM

TSGWFLTVSDLMNKKPLPFKLFSIDRCFRREQKEDKSHLMTYHSASC

AIAGEGVDINDGKAIAEGLLSQFGFTNFKFIPDEKKSKYYTPETQTEV

YAYHPKLKEWLEVATFGVYSPVALSKYGIDVPVMNLGLGVERLAMI

SGNFADVREMVYPQFYEHKLNDRNVASMVKLDKVPVMDEIYDLTK

ELIESCVKNKDLKSPCELAIEKTFSFGKTKKNVKINIFEKEEGKNLLGP

SILNEIYVYDGNVIGIPESFDGVKEEFKDFLEKGKSEGVATGIRYIDAL

CFKITSKLEEAFVSNTTEFKVKVPIVRSLSDINLKISSIALKQIMSKNK

VIDVRGPVFLNVEVKIE.

B. Elongation Factor Proteins

Nucleic acid sequences encoding mutant elongation factor proteins (EF-Sep) are described for use with phosphoseryl-tRNA synthetase (SepRS) and phosphoseryl-tRNA (tRNA$^{Sep}$) in site specific incorporation of phosphoserine into a protein or polypeptide. Typically, SepRS preferentially aminoacylates tRNA$^{Sep}$ with O-phosphoserine and the tRNA$^{Sep}$ recognizes at least one codon such as a stop codon. Due to the negative charge of the phosphoserine, Sep-tRNA$^{Sep}$ does not bind elongation factor Tu (EF-Tu). However, the disclosed EF-Sep proteins can bind Sep-tRNA$^{Sep}$ and protect Sep-tRNA$^{Sep}$ from deacylation.

In some embodiments, EF-Sep is a mutant form of bacterial EF-Tu having a mutation at one or more of amino acid residues corresponding to His67, Glu216, Asp217, Phe219, Thr229, and Asn274 in *E. coli* EF-Tu, which are located in the amino acid binding pocket for aminoacylated tRNA. In some embodiment, EF-Sep is a mutant form of eukaryotic elongation factor 1A (eEF1A) with mutations in positions equivalent to bacterial counterpart.

In preferred embodiments, EF-Sep has the amino acid sequence SEQ ID NO:1, SEQ ID NO:2, SEQ ID NO:3, SEQ ID NO:4, or a conservative variant thereof. For example, in some embodiments, the nucleic acid sequence encoding EF-Sep has the nucleic acid sequence SEQ ID NO:5, SEQ ID NO:6, SEQ ID NO:7, SEQ ID NO:8, or a conservative variant thereof.

C. Variants

Also disclosed are variants of the disclosed proteins and polynucleotides that include conservative substitutions, additions, and deletions therein not affecting the structure or function. For example, biologically active sequence variants of tRNA$^{Sep}$, SepRS, and EF-Sep and in vitro generated covalent derivatives of tRNA$^{Sep}$, SepRS, and EF-Sep that demonstrate tRNA$^{Sep}$, SepRS, and EF-Sep activity are disclosed.

Various types of mutagenesis can be used to modify a nucleic acid. They include, but are not limited to, sitedirected, random point mutagenesis, homologous recombination (DNA shuffling), mutagenesis using uracil containing templates, oligonucleotide-directed mutagenesis, phosphorothioate-modified DNA mutagenesis, and mutagenesis using methods such as gapped duplex DNA. Additional suitable methods include point mismatch repair, mutagenesis using repair-deficient host strains, restriction-selection and restriction-purification, deletion mutagenesis, mutagenesis by total gene synthesis and double-strand break repair.

Sequence variants of tRNA$^{Sep}$, SepRS, and EF-Sep fall into one or more of three classes: substitutional, insertional and/or deletional variants. Sequence variants of tRNA$^{Sep}$ include nucleotide variants, while sequence variants of SepRS and EF-Sep include nucleotide and/or amino acid variants. Insertions include amino and/or carboxyl terminal fusions as well as intrasequence insertions of single or multiple residues. tRNA$^{Sep}$, SepRS, and EF-Sep include, for example, hybrids of mature tRNA$^{Sep}$, SepRS, and EF-Sep with nucleotides or polypeptides that are homologous with tRNA$^{Sep}$, SepRS, and EF-Sep. tRNA$^{Sep}$, SepRS, and EF-Sep also include hybrids of tRNA$^{Sep}$, SepRS, and EF-Sep with nucleotides or polypeptides homologous to the host cell but not to tRNA$^{Sep}$, SepRS, and EF-Sep, as well as nucleotides or polypeptides heterologous to both the host cell and tRNA$^{Sep}$, SepRS, and EF-Sep. Fusions include amino or carboxy terminal fusions with either prokaryotic nucleotides or peptides or signal peptides of prokaryotic, yeast, viral or host cell signal sequences.

Insertions can also be introduced within the mature coding sequence of tRNA$^{Sep}$, SepRS, and EF-Sep. These, however, ordinarily will be smaller insertions than those of amino or carboxyl terminal fusions, on the order of one to four residues. Insertional sequence variants of tRNA$^{Sep}$, SepRS, and EF-Sep are those in which one or more residues are introduced into a predetermined site in the target tRNA$^{Sep}$, SepRS, and EF-Sep.

Deletion variants are characterized by the removal of one or more nucleotides or amino acid residues from the tRNA$^{Sep}$, SepRS, and EF-Sep sequence. For SepRS and EF-Sep, deletions or substitutions of cysteine or other labile residues may be desirable, for example in increasing the oxidative stability or selecting the preferred disulfide bond arrangement of SepRS or EF-Sep. Deletions or substitutions of potential proteolysis sites, e.g. Arg Arg, are accomplished, for example, by deleting one of the basic residues or substituting one by glutaminyl or histidyl residues. Variants ordinarily are prepared by site specific mutagenesis of nucleotides in the DNA encoding the tRNA$^{Sep}$, SepRS, and EF-Sep, thereby producing DNA encoding the variant, and thereafter expressing the DNA in recombinant cell culture. Variant tRNA$^{Sep}$, SepRS, and EF-Sep fragments may also be prepared by in vitro synthesis. The variants typically exhibit the same qualitative biological activity as the naturally-occurring analogue, although variants also are selected in order to modify the characteristics of tRNA$^{Sep}$, SepRS, and EF-Sep.

Substitutional variants are those in which at least one residue sequence has been removed and a different residue inserted in its place. Owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, conservative amino acid substitutions are also readily identified. Such conservative variations are a feature of each disclosed sequence. The substitutions which in general are expected to produce the greatest changes in SepRS or EF-Sep protein properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

While the site for introducing a nucleotide or amino acid sequence variation is predetermined, the mutation per se need not be predetermined. For example, in order to optimize the performance of a mutation at a given site, random mutagenesis may be conducted at the target codon or region and the expressed tRNA$^{Sep}$, SepRS, and EF-Sep variants screened for the optimal combination of desired activity. Techniques for making substitution mutations at predetermined sites in DNA having a known sequence are well known.

Substitutions are typically of single residues; insertions usually will be on the order of about from 1 to 10 residues; and deletions will range about from 1 to 30 residues. Substitutions, deletion, insertions or any combination thereof may be combined to arrive at a final construct. The mutations that will be made in the DNA encoding the variant SepRS and EF-Sep must not place the sequence out of reading frame and preferably will not create complementary regions that could produce secondary mRNA structure.

A DNA isolate is understood to mean chemically synthesized DNA, cDNA or genomic DNA with or without the 3' and/or 5' flanking regions. DNA encoding tRNA$^{Sep}$, SepRS, and EF-Sep can be obtained from other sources than *Methanocaldococcus jannaschii* by screening a cDNA library from cells containing mRNA using hybridization with labeled DNA encoding *Methanocaldococcus jannaschii* tRNA$^{Sep}$, SepRS, and EF-Sep, or fragments thereof (usually, greater than 10 bp).

The precise percentage of similarity between sequences that is useful in establishing sequence identity varies with the nucleic acid and protein at issue, but as little as 25% sequence similarity is routinely used to establish sequence identity. Higher levels of sequence similarity, e.g., 30%, 40%, 50%, 60%, 70%, 80%, 90%, 95% or 99% or more can also be used to establish sequence identity. Methods for determining sequence similarity percentages (e.g., BLASTP and BLASTN using default parameters) are generally available.

Alignment of sequences for comparison can be conducted by many well-known methods in the art, for example, by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), by the Gibbs sampling method (Chatterji and Pachter, *J Comput Biol.* 12(6):599-608 (2005)), by PSI-BLAST-ISS (Margelevicius and Venclovas, *BMC Bioinformatics* 21; 6:185 (2005)), or by visual inspection. One algorithm that is suitable for determining percent sequence identity and sequence similarity is the BLAST algorithm, which is described in Altschul et al., *J. Mol. Biol.* 215:403-

410 (1990). Software for performing BLAST analyses is publicly available through the National Center for Biotechnology Information website.

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

D. Expression or Translation Systems

Also disclosed are expression or translation systems for incorporate phosphoserine into a growing polypeptide chain (protein). Components of a translation system generally include amino acids, ribosomes, tRNAs, synthetases, and mRNA. The disclosed tRNA$^{Sep}$, SepRS, and EF-Sep can be added to a translation system, in vivo or in vitro to incorporate phosphoserine into a protein.

In some embodiments, a cell-based (in vivo) expression system is used. In these embodiments, nucleic acids encoding one or more of tRNA$^{Sep}$, SepRS, and EF-Sep are delivered to cells under conditions suitable for translation and/or transcription of tRNA$^{Sep}$, SepRS, EF-Sep, or a combination thereof. The cells can in some embodiments be prokaryotic, e.g., an *E. coli* cell, or eukaryotic, e.g., a yeast, mammalian, plant, or insect or cells thereof.

In some embodiments, a cell-free (in vitro) expression system is used. The most frequently used cell-free translation systems involve extracts containing all the macromolecular components (70S or 80S ribosomes, tRNAs, aminoacyl-tRNA synthetases, initiation, elongation and termination factors, etc.) required for translation of exogenous RNA. To ensure efficient translation, each extract is supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors ($Mg^{2+}$, $K^+$, etc.).

i) Promoters and Enhancers

Nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Therefore, also disclosed is a polynucleotide encoding one or more of tRNA$^{Sep}$, SepRS, and EF-Sep, operably linked to an expression control sequence.

Suitable promoters are generally obtained from viral genomes (e.g., polyoma, Simian Virus 40 (SV40), adenovirus, retroviruses, hepatitis-B virus, and cytomegalovirus) or heterologous mammalian genes (e.g. beta actin promoter). Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 bp in length, and they function in cis. Enhancers function to increase transcription from nearby promoters. Enhancers also often contain response elements that mediate the regulation of transcription. Many enhancer sequences are now known from mammalian genes (globin, elastase, albumin, α-fetoprotein and insulin). However, enhancer from a eukaryotic cell virus are preferably used for general expression. Suitable examples include the SV40 enhancer on the late side of the replication origin, the cytomegalovirus early promoter enhancer, the polyoma enhancer on the late side of the replication origin, and adenovirus enhancers.

In certain embodiments the promoter and/or enhancer region can act as a constitutive promoter and/or enhancer to maximize expression of the region of the transcription unit to be transcribed. In certain constructs the promoter and/or enhancer region is active in all eukaryotic cell types, even if it is only expressed in a particular type of cell at a particular time. A preferred promoter of this type is the CMV promoter. In other embodiments, the promoter and/or enhancer is tissue or cell specific.

In certain embodiments the promoter and/or enhancer region is inducible. Induction can occur, e.g., as the result of a physiologic response, a response to outside signals, or as the result of artificial manipulation. Such promoters are well known to those of skill in the art. For example, in some embodiments, the promoter and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs.

ii) Cell Delivery Systems

There are a number of compositions and methods which can be used to deliver nucleic acids to cells, either in vitro or in vivo. These methods and compositions can largely be broken down into two classes: viral based delivery systems and non-viral based delivery systems. For example, nucleic acids can be delivered through a number of direct delivery systems such as electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are well known in the art and readily adaptable for use with the compositions and methods described herein.

Transfer vectors can be any nucleotide construction used to deliver genetic material into cells. In some embodiments the vectors are derived from either a virus or a retrovirus. Viral vectors include, for example, Adenovirus, Adenoassociated virus, Herpes virus, Vaccinia virus, Polio virus, AIDS virus, neuronal trophic virus, Sindbis and other RNA viruses, including these viruses with the HIV backbone.

Typically, viral vectors contain nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA. The necessary functions of the removed early genes are typically supplied by cell lines which have been engineered to express the gene products of the early genes in trans.

Nucleic acids can also be delivered through electroporation, sonoporation, lipofection, or calcium phosphate precipitation. Lipofection involves the use liposomes, including cationic liposomes (e.g., DOTMA, DOPE, DC-cholesterol) and anionic liposomes, to delivery genetic material to a cell. Commercially available liposome preparations include LIPOFECTIN, LIPOFECTAMINE (GIBCO-BRL, Inc., Gaithersburg, Md.), SUPERFECT (Qiagen, Inc. Hilden, Germany), and TRANSFECTAM (Promega Biotec, Inc., Madison, Wis.).

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome. Techniques for integration of genetic material into a host genome are also known and include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

iii) Markers

The vectors used to deliver the disclosed nucleic acids to cells can further include nucleic acid sequence encoding a marker product. This marker product is used to determine if the gene has been delivered to the cell and once delivered is being expressed. In some embodiments the marker is a detectable label. Exemplary labels include the E. coli lacZ gene, which encodes β-galactosidase, and green fluorescent protein (GFP).

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line.

These schemes typically use a drug to arrest growth of a host cell. Those cells which have a novel gene would express a protein conveying drug resistance and would survive the selection.

III. Methods

A. Site-Specific Phosphorylation of Proteins

Methods for incorporating phosphoserine into polypeptides are disclosed. The method involves the use of tRNA$^{Sep}$, SepRS, and EF-Sep in the translation process for a target polypeptide from mRNA. SepRS preferentially aminoacylates tRNA$^{Sep}$ with O-phosphoserine. The resulting Sep-tRNA$^{Sep}$ recognizes at least one codon in the mRNA for the target protein, such as a stop codon. EF-Sep mediates the entry of the Sep-tRNA$^{Sep}$ into a free site of the ribosome. If the codon-anticodon pairing is correct, EF-Sep hydrolyzes guanosine triphosphate (GTP) into guanosine diphosphate (GDP) and inorganic phosphate, and changes in conformation to dissociate from the tRNA molecule. The Sep-tRNA$^{Sep}$ then fully enters the A site, where its amino acid is brought near the P site's polypeptide and the ribosome catalyzes the covalent transfer of the amino acid onto the polypeptide.

In preferred embodiments, the tRNA$^{Sep}$ is a tRNA$^{Cys}$ from a methanogenic archaea, such as *Methanocaldococcus jannaschii*, containing a mutation (e.g., C20U) that improves aminoacylation of the tRNA by SepRS without affecting CysRS recognition. In some embodiments, the tRNA$^{Sep}$ contains an anticodon that binds a codon other than a Cys codon, such as a stop codon. In some embodiments, the tRNA$^{Sep}$ is encoded the nucleic acid sequence SEQ ID NO:41, or a conservative variant thereof.

In some embodiments, the SepRS is any tRNA synthetase that preferentially aminoacylates tRNA$^{Sep}$ with a phosphoserine. In preferred embodiments, the SepRS is a tRNA synthetase from a methanogenic archaea, such as *Methanococcus maripaludis* or *Methanocaldococcus jannaschii*. In some embodiments, the SepRS has the amino acid sequence SEQ ID NO:43 or 46, or a conservative variant thereof.

In some embodiments, the EF-Sep is any elongation factor protein that binds Sep-tRNA$^{Sep}$ and catalyzes the covalent transfer of the phosphoserine amino acid onto the polypeptide. EF-Sep proteins can bind Sep-tRNA$^{Sep}$ and can preferably protect Sep-tRNA$^{Sep}$ from deacylation. In some embodiments, EF-Sep is a mutant form of bacterial EF-Tu having a mutation at one or more of amino acid residues corresponding to His67, Glu216, Asp217, Phe219, Thr229, and Asn274 in *E. coli* EF-Tu, which are located in the amino acid binding pocket for aminoacylated tRNA. In some embodiments, EF-Sep has the amino acid sequence SEQ ID NO:1, SEQ ID NO:2, SEQ ID NO:3, SEQ ID NO:4, or a conservative variant thereof. In some embodiments, EF-Sep is a mutant form of eukaryotic elongation factor 1A (eEF1A) with mutations in positions equivalent to bacterial counterpart.

i) In Vitro Transcription/Translation

In one embodiment, the nucleic acids encoding tRNA$^{Sep}$ and SepRS activity are synthesized prior to translation of the target protein and are used to incorporate phosphoserine into a target protein in a cell-free (in vitro) protein synthesis system.

In vitro protein synthesis systems involve the use crude extracts containing all the macromolecular components (70S or 80S ribosomes, tRNAs, aminoacyl-tRNA synthetases, initiation, elongation and termination factors, etc.) required for translation of exogenous RNA. For the current method, the tRNAs, aminoacyl-tRNA synthetases, and elongation factors in the crude extract are supplemented with tRNA$^{Sep}$, SepRS, and EF-Sep. To ensure efficient translation, each extract must be supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors (Mg2+, K+, etc.).

In vitro protein synthesis does not depend on having a polyadenylated RNA, but if having a poly(A) tail is essential for some other purpose, a vector may be used that has a stretch of about 100 A residues incorporated into the polylinker region. That way, the poly(A) tail is "built in" by the synthetic method. In addition, eukaryotic ribosomes read RNAs that have a 5' methyl guanosine cap more efficiently. RNA caps can be incorporated by initiation of transcription using a capped base analogue, or adding a cap in a separate in vitro reaction post-transcriptionally.

Suitable in vitro transcription/translation systems include, but are not limited to, the rabbit reticulocyte system, the *E. coli* S-30 transcription-translation system, the wheat germ based translational system. Combined transcription/translation systems are available, in which both phage RNA polymerases (such as T7 or SP6) and eukaryotic ribosomes are present. One example of a kit is the TNT® system from Promega Corporation.

ii) In Vivo Methods

Host cells and organisms can also incorporate phosphoserine into proteins or polypeptides via nucleic acids encoding tRNA$^{Sep}$, SepRS, and EF-Sep. Nucleic acids encoding tRNA Sep, SepRS, and EF-Sep, operably linked to one or more expression control sequences are introduced into cells or organisms using a cell delivery system. These cells also contain a gene encoding the target protein operably linked to an expression control sequence.

Suitable organisms include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems.

It will be understood by one of ordinary skill in the art that regardless of the system used (i.e. in vitro or in vivo), expression of genes encoding tRNA$^{Sep}$, SepRS, and EF-Sep activity will result in site specific incorporation of phosphoserine into the target polypeptides or proteins that are translated in the system. Host cells are genetically engineered (e.g., transformed, transduced or transfected) with the vectors encoding tRNA$^{Sep}$, SepRS, and EF-Sep, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation, infection by viral vectors, high velocity ballistic penetration by small particles with the nucleic acid either within the matrix of small beads or particles, or on the surface. Such vectors can optionally contain one or more promoter. A "promoter" as used herein is a DNA regulatory region capable of initiating transcription of a gene of interest.

Kits are commercially available for the purification of plasmids from bacteria, (see, e.g., GFX™ Micro Plasmid Prep Kit from GE Healthcare; Strataprep® Plasmid Miniprep Kit and StrataPrep® EF Plasmid Midiprep Kit from Stratagene; GenElute™ HP Plasmid Midiprep and Maxiprep Kits from Sigma-Aldrich, and, Qiagen plasmid prep kits and QIAfilter™ kits from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems.

Prokaryotes useful as host cells include, but are not limited to, gram negative or gram positive organisms such as *E. coli* or Bacilli. In a prokaryotic host cell, a polypeptide may include an N-terminal methionine residue to facilitate expression of the recombinant polypeptide in the prokaryotic host cell. The N-terminal Met may be cleaved from the expressed recombinant polypeptide. Promoter sequences commonly used for recombinant prokaryotic host cell expression vectors include lactamase and the lactose promoter system.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct an expression vector using pBR322, an appropriate promoter and a DNA sequence are inserted into the pBR322 vector. Other commercially available vectors include, for example, T7 expression vectors from Invitrogen, pET vectors from Novagen and pALTER® vectors and PinPoint® vectors from Promega Corporation.

Yeasts useful as host cells include, but are not limited to, those from the genus *Saccharomyces*, *Pichia*, *K. Actinomycetes* and *Kluyveromyces*. Yeast vectors will often contain an origin of replication sequence, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., J. Biol. Chem. 255:2073, (1980)) or other glycolytic enzymes (Holland et al., Biochem. 17:4900, (1978)) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Fleer et al., Gene, 107:285-195 (1991), in Li, et al., *Lett Appl Microbiol.* 40(5):347-52 (2005), Jansen, et al., Gene 344:43-51 (2005) and Daly and Hearn, *J. Mol. Recognit.* 18(2):119-38 (2005). Other suitable promoters and vectors for yeast and yeast transformation protocols are well known in the art.

Mammalian or insect host cell culture systems well known in the art can also be employed to express recombinant tRNA$^{Sep}$, SepRS, and EF-Sep for producing proteins or polypeptides containing phosphoserine. Commonly used promoter sequences and enhancer sequences are derived from Polyoma virus, Adenovirus 2, Simian Virus 40 (SV40), and human cytomegalovirus. DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are well known in the art.

B. Purifying Proteins Containing Phosphoserine

Proteins or polypeptides containing phosphoserine can be purified, either partially or substantially to homogeneity, according to standard procedures known to and used by those of skill in the art including, but not limited to, ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, and gel electrophoresis. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against proteins containing phosphoserine are used as purification reagents, e.g., for affinity-based purification of proteins containing phosphoserine. Once purified, partially or to homogeneity, as desired, the polypeptides may be used as assay components, therapeutic reagents, immunogens for antibody production, etc.

Those of skill in the art will recognize that, after synthesis, expression and/or purification, proteins can possess conformations different from the desired conformations of the relevant polypeptides. For example, polypeptides produced by prokaryotic systems often are optimized by exposure to chaotropic agents to achieve proper folding. During purification from lysates derived from E. coli, the expressed protein is optionally denatured and then renatured. This is accomplished by solubilizing the proteins in a chaotropic agent such as guanidine HCl.

It is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are well known to those of skill in the art Refolding reagents can be flowed or otherwise moved into contact with the one or more polypeptide or other expression product, or vice-versa.

C. Using Phosphoserine Containing Peptides

Proteins or polypeptides containing phosphoserine and antibodies that bind to such proteins produced by the methods described herein can be used for research involving phosphoproteins such as the study of kinases, phosphotases, and target proteins in signal transduction pathways. Proteins or polypeptides containing phosphoserine produced by the methods described herein can also be used for antibody production, protein array manufacture and development of cell-based screens for new drug discovery.

IV. Kits

Kits for producing polypeptides and/or proteins containing phosphoserine are also provided. For example, a kit for producing a protein that contains phosphoserine in a cell is provided, where the kit includes a polynucleotide sequence encoding tRNA$^{Sep}$, a polynucleotide sequence encoding SepRS, and a polynucleotide sequence encoding EF-Sep. In one embodiment, the kit further includes phosphoserine. In another embodiment, the kit further comprises instructional materials for producing the protein. In another embodiment, a kit for producing a protein that contains phosphoserine in vitro is provided, where the kit includes a polynucleotide sequence encoding tRNA$^{Sep}$, a polynucleotide sequence encoding SepRS, a polynucleotide sequence encoding EF-Sep, and phsophoserine. In another embodiment, the kit further comprises instructional materials for producing the protein in vitro.

The present invention will be further understood by reference to the following non-limiting examples.

EXAMPLES

Example 1

SepRS and tRNA$^{Sep}$ are an Orthogonal Pair in E. coli

Materials and Methods

Constructions of Strains

To prevent possible enzymatic dephosphorylation of O-phospho-L-serine (Sep) in vivo, the gene encoding phosphoserine phosphatase (serB), which catalyzes the last step in serine biosynthesis, was deleted from Escherichia coli strains Top10 and BL21. Markerless gene deletions were carried out using a h-red and FLP recombinase-based gene knockout strategy as described by Datsenko K A, et al. Proc Natl Acad Sci USA. 97:6640 (2000). E. coli strains Top10ΔserB and BL21ΔserB were used for EF-Tu library construction and MEK1 expression experiments.

Construction of Plasmids

To construct plasmid pSepT, the full-length gene encoding tRNA$^{Sep}$ was constructed from overlapping oligonucleotides and ligated immediately downstream of the lpp promoter in pTECH (Bunjun S, et al. Proc Natl Acad Sci USA. 97:12997 (2000)) using EcoRI and BamHI restriction sites. pCysT, encoding the wild type tRNA$^{Cys}$ gene from Methanocaldococcus jannaschii was constructed in the same way.

The gene fragment encoding β-lactamase was PCR-amplified from plasmid pUC18 using primers PBLAF (5'-TGC GCA ATG CGG CCG CCC GTA GCG CCG ATG GTA GTG T-3', SEQ ID NO:9) and PBLAR (5'-ACA CGG AGA TCT CTA AAG TAT ATA TGA GTA AAC-3', SEQ ID NO: 10), and ligated with a NotI and BglII digested PCR product which was constructed from pSepT using primers PSEPF (5'-TGC GCA ATG CGG CCG CCC GGG TCG AAT TTG CTT TCG A-3', SEQ ID NO: 11) and PSEPR (5'-ACA CGG AGA TCT ATG CCC CGC GCC CAC CGG AAG-3', SEQ ID NO:12).

pKD was derived from pKK223-3 (Pharmacia). The ampicillin resistance gene was replaced with a kanamycin resistance gene by combining two PCR products generated from pKK223-3 and pET28a. The following PCR primers were used: PKF (5'-TGC AGCA ATG CGG CCG CTT TCA CCG TCA TCA CCG AAA C-3', SEQ ID NO:13) and PKR (5'-GGG ACG CTA GCA AAC AAA AAG AGT TTG TAG AA-3', SEQ ID NO:14) for pKK223-3 amplification and PKNF (5'-GGG ACG CTA GCT TTT CTC TGG TCC CGC CGC AT-3', SEQ ID NO:15) and PKNR (5'-TGC GCA ATG CGG CCG CGG TGG CAC TTT TCG GGG AAA T-3', SEQ ID NO:16) for $Kan^R$ gene amplification.

The original multiple cloning site (MCS; NcoI-EcoRI-SacI) was modified by adding an additional ribosome binding site (RBS) and a second MCS (NdeI-BamHI-SalI-HindIII), thus enabling simultaneous protein expression from two genes, both under the control of the same tac promoter. The *Methanococcus maripaludis* SepRS gene was cloned into pKD using NcoI and SacI sites to produce pKD-SepRS. The *E. coli* EF-Tu gene (tufB) was ligated into pKD-SepRS using BamHI and SalI sites resulting in pKD-SepRS-EFTu. The *M. maripaludis* pscS gene encoding SepCysS was cloned into pKD-SepRS using BamHI and SalI sites to produce pKD-SepRS-SepCysS and the *M. maripaludis* CysRS gene was cloned into pKD using EcoRI and SalI to yield pKD-CysRS.

pCAT112TAG-SepT was created from pACYC184. The gene encoding chloramphenicol acetyltransferase (CAT) was modified by quickchange mutagenesis to introduce an amber stop codon at position Asp112 (Wang L, et al. Science 292:498 (2001)). The resulting plasmid was PCR amplified using primers PBLAF (5'-TGC GCA ATG CGG CCG CCC GTA GCG CCG ATG GTA GTG T-3', SEQ ID NO:9) and PBLAR (5'-ACA CGG AGA TCT CTA AAG TAT ATA TGA GTA AAC-3', SEQ ID NO:10) and ligated with a PCR product containing a $tRNA^{Sep}$ expression cassette from pSepT, created with primers TSEPF (5'-GCA TGC GCC GCC AGC TGT TGC CCG TCT CGC-3', SEQ ID NO:17) and TSEPR (5'-GCA TAG ATC TTC AGC TGG CGA AAG GGG GAT G-3', SEQ ID NO:18).

Plasmid pCcdB was created by adding a ccdB gene under the control of a lac promoter into pTECH using NotI and BglII sites (Wang L, et al. *Science* 292:498 (2001)). Two amber stop codons were introduced at positions 13 and 44 based on the crystal structure and mutagenesis study of the CcdB protein (Bernard, P., et al. Gene 148:71 (1994); Bajaj K, et al. *Proc Natl Acad Sci USA* 102:16221 (2005)).

Plasmid pL11C-SepT encodes $tRNA^{Sep}$ and the C-terminal domain of the ribosomal protein L11 under control of lpp promoters. Part of the rplK gene was PCR amplified from genomic *E. coli* DNA using primers L11C-F (5'-GGA ATT CCA TAT GAC CAA GAC CCC GCC GGC AGC AGT T-3', SEQ ID NO:38) and L11C-R (5'-AGG CGC GCC TTA GTC CTC CAC TAC-3', SEQ ID NO:39). The PCR product was digested with NdeI and AscI and was ligated into NdeI and AscI digested pMYO127TAG-SepT to replace the myoglobin gene.

To construct pMAL-EFTu and pMAL-EFSep *E. coli* tufB, or the gene encoding EF-Sep, respectively, were cloned between the NdeI and BamHI sites in the pET20b plasmid (Novaven) to add a C-terminal $His_6$ tag. This fusion construct was then PCR-amplified using primers adding MfeI and PstI restriction sites. The PCR product was cloned in-frame between EcoRI and PstI in pMAL-c2x (New England Biolabs) to add an N-terminal maltose binding protein (MBP) tag.

Aminoacylation of tRNA and EF-Sep Binding Assays

In vitro transcript of *Methanocaldococcus jannaschii* $tRNA^{Cys}$ was prepared and acylated with [$^{14}$C]Sep (55 mCi/mmol) using recombinant *Methanococcus maripaludis* SepRS as described previously by Hohn M J, et al. *Proc Natl Acad Sci USA*. 2006 Nov. 28; 103(48):18095-100. Sep-$tRNAc^{Cys}$ was phenol/chlorophorm extracted, and the aqueous phase was passed over Sephadex G25 Microspin columns (GE Healthcare) equilibrated with water.

Protection of Sep-$tRNA^{Cys}$ by EF-Tu was assayed as described earlier with slight modifications (Ling J, et al. *RNA*. 2007 November; 13(11):1881-6.). Briefly, EF-Tu or EF-Sep (both purified as maltose binding protein fusion proteins) were activated for 20 min. at 37° C. in buffer containing 100 mM Tris-HCl (pH 8.2), 120 mM $NH_4Cl$, 7 mM $MgCl_2$, 5 mM DTT, 5 mM phosphoenolpyruvate, 1.5 mM GTP, and 0.12 µg/µl pyruvate kinase. Hydrolysis of 2 M [$^{14}$C]Sep-$tRNA^{Cys}$ was then monitored at 25° C. in the presence of 40 µM EF-Tu (wt), EF-Sep, or BSA, respectively. Aliquots were taken from the reaction mix at indicated time points and spotted on 3MM filter discs presoaked with 10% trichloroacetic acid. Filters were washed with 5% trichloroacetic acid, dried, and radioactivity was measured by liquid scintillation counting.

Results

The Sep-insertion strategy was based on the discovery that most methanogens form Cys-$tRNA^{Cys}$ by an unusual pathway required for cysteine synthesis in these archaea (Sauerwald A. et al., *Science* 307, 1969 (2005)). In this route (FIG. 1A), $tRNA^{Cys}$ first becomes acylated with O-phosphoserine (Sep) by O-phosphoseryl-tRNA synthetase (SepRS), an unusual aminoacyl-tRNA synthetase specific solely for the substrates Sep and $tRNA^{Cys}$ (Hohn, M J., et al. *Proc Natl Acad Sci USA* 103, 18095 (2006)). The resulting product Sep-$tRNA^{Cys}$ is then converted to Cys-$tRNA^{Cys}$ by the enzyme SepCysS in the presence of a sulfur-donor (Sauerwald A. et al., *Science* 307, 1969 (2005)). The exclusive recognition of Sep by SepRS was further confirmed by the structural elucidation of this enzyme and by the biochemical analysis of its catalytic site (Kamtekar S. et al., *Proc Natl Acad Sci USA* 104, 2620 (2007); Fukunaga, R. et al., *Nat Struct Mol Biol* 14, 272 (2007)). The molecular basis of *Methanocaldococcus jannaschii* (Mj) $tRNA^{Cys}$ recognition by SepRS and CysRS from *Methanococcus maripaludis* (Mmp) was also explored, yielding the SepRS-specific tRNA identity elements (Hohn, M J., et al. *Proc Natl Acad Sci USA* 103, 18095 (2006)). Based on these results it was decided to test the applicability of Mj $tRNA^{Cys}$ and Mmp SepRS as an orthogonal pair for UAG-directed translational incorporation of Sep into proteins expressed in *Escherichia coli*. A scheme was sought for co-translational insertion of phosphoserine (Sep) into proteins in *E. coli* in response to the amber codon UAG. Methanogens utilize an aminoacyl-tRNA synthetase (SepRS) that acylates $tRNA^{Cys}$ with Sep during the biosynthesis of Cys-$tRNA^{Cys}$ (FIG. 1A).

Figure 1B:
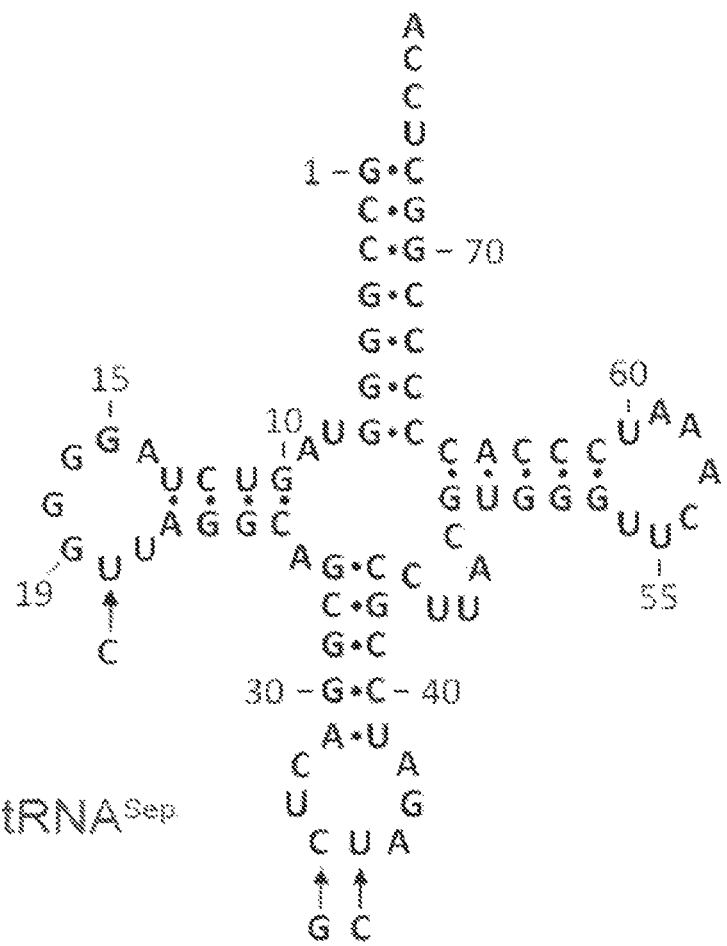
FIG. 1B is a diagram showing the secondary structure (of *Methanocaldococcus jannaschii* tRNA$^{Cys}$ (SEQ ID NO:41) shown in clover leaf form. Mutations introduced to form tRNA$^{Sep}$ are indicated with arrows.

A tRNA ($tRNA^{Sep}$) was designed that could be aminoacylated with phosphoserine (FIG. 1B). $tRNA^{Sep}$ is a tRNA derived from Mj $tRNA^{Cys}$ containing a C20U change that improves 2.5-fold the aminoacylation by SepRS without affecting CysRS recognition. In addition, $tRNA^{Sep}$ was modified to be an amber suppressor by including two mutations in the anticodon (FIG. 1B).

Figure 1C:
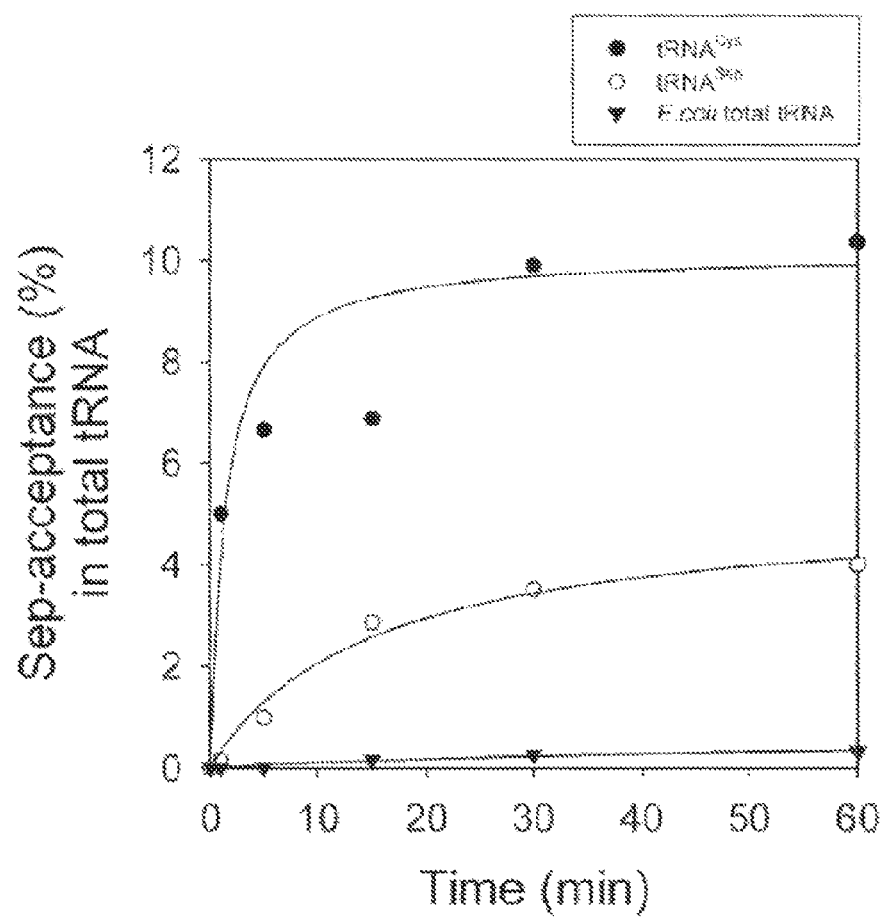
FIG. 1C is a graph showing percent phosphoserine (Sep) acceptance in *M. jannaschii* tRNA as a function of time (min) for unfractionated total tRNA from *E. coli* (triangle) or *E. coli* strains expressing tRNA$^{Cys}$ (closed circle) or tRNA$^{Sep}$ (open circle).

Both $tRNA^{Sep}$ and $tRNA^{Cys}$ were overexpressed in *E. coli*. In vitro aminoacylation by Mmp SepRS showed (FIG. 1C) that the anticodon change lowered (to about 40%) the activity of $tRNA^{Sep}$ when compared to $tRNA^{Cys}$. Total *E. coli* tRNA could not be charged with Sep (FIG. 1C). Based on these in vitro data, Mj $tRNA^{Sep}$ and Mmp SepRS appear to be an orthogonal pair.

Figure 2:
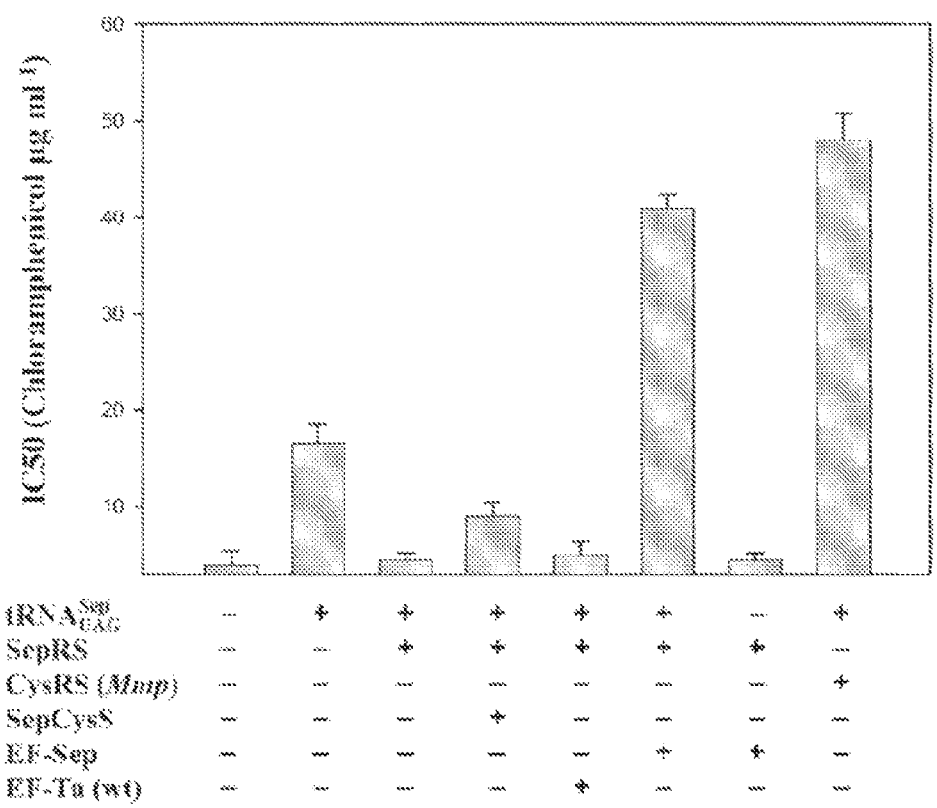
FIG. 2 is a graph showing chloramphenicol resistance (IC50, μg/ml) for *E. coli*. containing 1) a chloramphenicol acetyltransferase (CAT) gene with an amber stop code (UAG) at a permissive site and 2) combinations of tRNA$^{Sep}$, [SepRS or CysRS (Mmp)], SepCysS, and [EF-Sep or and EF-Tu (wt)]. The suppressor tRNA$^{Sep}$ was coexpressed with the indicated enzymes in *E. coli* Top10ΔserB. Selection was carried out on LB agar plates containing 2 mM Sep and various concentrations of chloramphenicol.

Efficient and selective addition of Sep to the *E. coli* genetic repertoire requires exclusive interaction of SepRS with $tRNA^{Sep}$ for Sep-$tRNA^{Sep}$ formation without interfering in the host translation system as well as a sufficient intracellular concentration of Sep. As *E. coli* has a Sep-compatible transporter (Wanner, B L. *FEMS Microbiol Lett* 79, 133 (1992)), Sep (2 mM) was added to the growth medium, and the endogenous serB gene encoding phosphoserine phosphatase was deleted in the *E. coli* test strain. To assess whether the Mj tRNA$^{Sep}$/Mmp SepRS pair is functional and orthogonal in *E. coli*, a suppression assay was performed that employed a chloramphenicol acetyltransferase (CAT) gene with a UAG stop codon at the permissive position 112 (wild-type amino acid: Asp) to produce chloramphenicol (Cm) acetyltransferase; then cell survival was measured in the presence of Sep and varying amounts of Cm. The different IC$_{50}$ values (FIG. 2) relate to suppression efficiency (i.e., amount of CAT made dependent on the various transformed genes). When only tRNA$^{Sep}$ is expressed (FIG. 2, second bar) Cm resistance increases about 3.3-fold over background (FIG. 2, first bar). Thus, tRNA$^{Sep}$ can be aminoacylated to a certain degree by an unknown *E. coli* aminoacyl-tRNA synthetase (Gln is being incorporated at the amber stop codon). In contrast, simultaneous expression of tRNA$^{Sep}$ and SepRS does not provide Cm resistance (FIG. 2, third bar). This may indicate that SepRS can out-compete any endogenous aminoacyl-tRNA synthetase and form Sep-tRNA$^{Sep}$; however, this aminoacyl-tRNA is not delivered to the ribosome or not accommodated on the ribosome. Providing additional EF-Tu does not improve the result (FIG. 2, fifth bar). Co-expression of tRNA$^{Sep}$, SepRS and SepCysS should result in formation of Sep-tRNA$^{Sep}$ and subsequent SepCysS-mediated conversion to Cys-tRNA$^{Sep}$ (A. Sauerwald et al., *Science* 307, 1969 (2005)). Indeed, a 2.3-fold increase in Cm resistance is observed (FIG. 2, sixth bar). This further supports the notion that while Sep-tRNA$^{Sep}$ is synthesized, it cannot be used properly by the *E. coli* protein biosynthesis machinery. On the other hand, co-expression of tRNA$^{Sep}$ and Mmp CysRS generates a 12.3-fold increase in Cm resistance (FIG. 2, eight bar), demonstrating that Cys-tRNA$^{Sep}$ can be readily used for amber codon suppression in the CAT gene.

Figure 3:
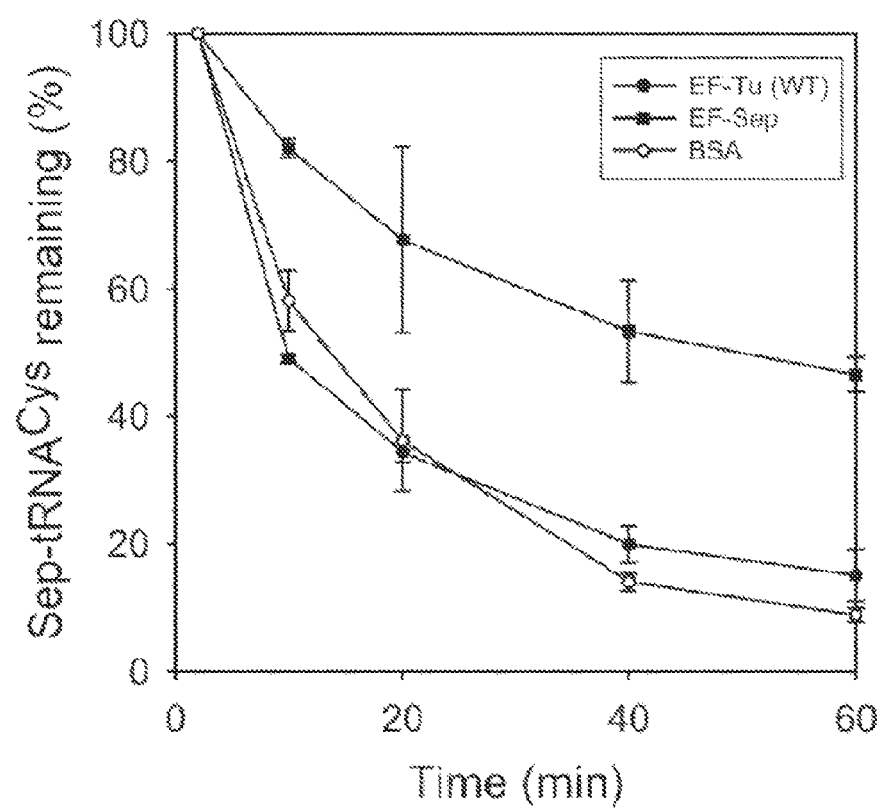
FIG. 3 is a graph showing deacylation of [$^{14}$C]Sep-tRNA$^{Cys}$ (percent Sep-tRNA$^{Cys}$ remaining) as a function of time following incubated in the presence and absence of bovine serum albumin control (open circle), wild type EF-Tu (closed circle), or EF-Sep (square).
Figure 5A:
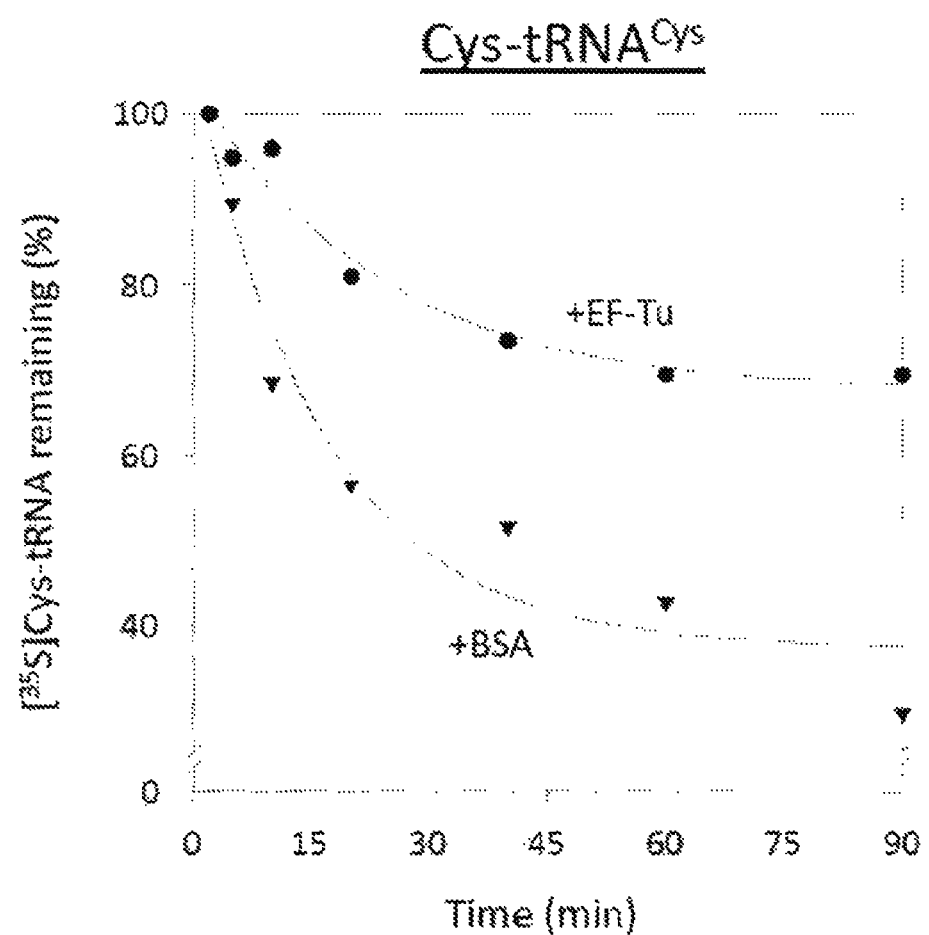
FIGS. 5A and 5B are graphs showing EF-Tu protects Cys-tRNA$^{Cys}$ (FIG. 5A) but not Sep-tRNA$^{Cys}$ (FIG. 5B) from deacylation. Hydrolysis of *M. jannaschii* [$^{35}$S]Cys-tRNA$^{Cys}$ or [$^{14}$C]Sep-tRNA$^{Cys}$ was determined at pH 8.2 and room temperature in the presence or absence of EF-Tu.
Figure 5B:
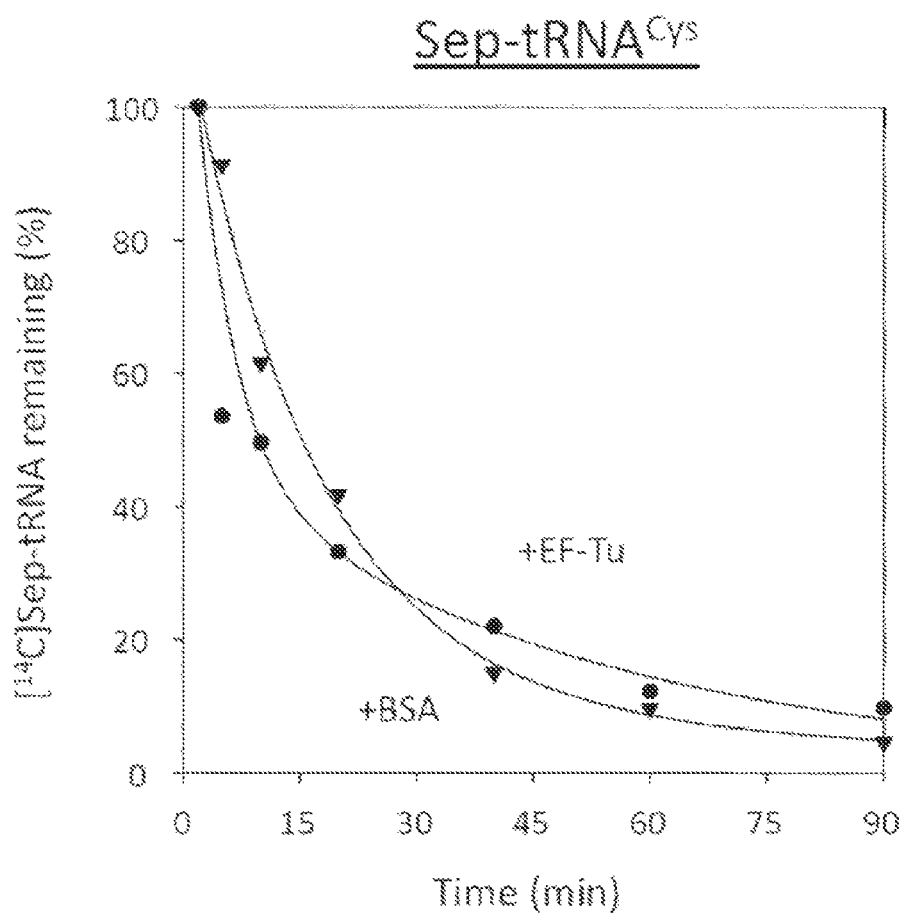

Given that EF-Tu is a component of quality control in protein synthesis (LaRiviere, F J., et al. *Science* 294, 165 (2001)), it is highly plausible that Sep-tRNA$^{Sep}$ may be rejected by EF-Tu in order not to interfere with the complicated cellular mechanism of phosphoprotein production. Chemically synthesized Sep-tRNA$^{Gln}$ was a poor substrate for in vitro protein synthesis (Rothman D M. et al., *J Am Chem Soc* 127, 846 (2005)). tRNAs carrying negatively charged amino acids are bound poorly by EF-Tu (Dale, T., et al. *Biochemistry* 43, 6159 (2004)), and molecular dynamics simulations suggested that Sep-tRNA$^{Cys}$ may not be bound by EF-Tu (Eargle, J., et al. *J Mol Biol* 377, 1382 (2008)). This assumption was tested in EF-Tu mediated Sep-tRNA hydrolysis protection experiments (J. Ling et al., *Proc Natl Acad Sci USA* 104, 15299 (2007)), and incubated recombinant *E. coli* EF-Tu with the Mj tRNA$^{Cys}$ in vitro transcript either acylated with [$^{35}$S]Cys or [$^{14}$C]Sep at pH 8.2. While EF-Tu protected [$^{35}$S]Cys-tRNA$^{Cys}$ from deacylation (FIG. 5A), Sep-tRNA$^{Cys}$ was significantly deacylated irrespective of the presence of EF-Tu (FIG. 3 and FIG. 5B). Thus, insufficient binding of Sep-tRNA$^{Sep}$ to EF-Tu may explain the lack of Sep insertion into protein.

Example 2

Development of EF-Sep

Materials and Methods

Library Construction and Selection of Sep-tRNA Specific EF-Tu

Six residues, His67, Glu216, Asp217, Phe219, Thr229, and Asn274, located in the amino acid binding pocket of the *E. coli* elongation factor EF-Tu were selected for randomization based on the crystal structure of the *E. coli* EF-Tu: Phe-tRNA$^{Phe}$ complex (protein data base accession number 1OB2). Multiple rounds of overlap PCR were carried out to incorporate random codons (NNK) at these positions by using the following primers described in Park H-S et al., *Science* 311:535-538 (2006):

```
67XF,
                                  (SEQ ID NO: 19)
5'-GT ATC ACC ATC AAC ACT TCT NNK GTT GAA

TAC GAC ACC CCG-3';

H67R,
                                  (SEQ ID NO: 20)
5'-AGA AGT GTT GAT GGT GAT AC-3';

216XF,
                                  (SEQ ID NO: 21)
5'-CCT TTC CTG CTG CCG ATC NNK NNK GTA NNK

TCC ATC TCC GGT CGT GGT-3';

216R,
                                  (SEQ ID NO: 22)
5'-GAT CGG CAG CAG GAA CGG-3';

229XF,
                                  (SEQ ID NO: 23)
5'-GGT CGT GGT ACC GTT GTT NNK GGT CGT GTA

GAA CGC GG-3';

229R,
                                  (SEQ ID NO: 24)
5'-AAC AAC GGT ACC ACG ACC-3';

274XF,
                                  (SEQ ID NO: 25)
5'-GAA GGC CGT GCT GGT GAG NNK GTA GGT GTT

CTG CTG CG-3';
and 274R,
                                  (SEQ ID NO: 26)
5'-CTC ACC AGC ACG GCC TTC-3'.
```

The final PCR products were purified and digested with BamHI and SalI, and ligated into pKD-SepRS to generate the EF-Tu library. The ligated vectors were transformed into *E. coli* Top10ΔserB containing pCAT112-SepT to generate a library of 3×10$^8$ mutants. The unbiased mutation of the library was confirmed by selecting twenty random clones and sequencing each mutant tufB insert.

The mutant EF-Tu library was subjected to a first round of selection, in which clones sup-pressing the amber stop codon in the CAT gene can survive on LB plates supplemented with 10 mg/ml tetracycline (Tc), 25 mg/ml Kan, 50 mg/ml chloramphenicol (Cm), 2 mM Sep, and 0.05 mM isopropyl-β-D-thiogalactopyranoside (IPTG). After 48 h incubation at 30° C., a pool of 10$^4$ colonies was collected from the plates for plasmid preparation. The pKD-SepRS-EFTu plasmids were separated from the reporter plasmid by agarose gel electrophosis and isolated using the Qiagen gel purification kit.

There is a possibility that mutations in the amino acid binding site of EF-Tu could induce incorporation of natural amino acids in response to the amber codon in the CAT gene, resulting in false positive clones. To select against these EF-Tu mutants, the pKD-SepRS-EFTu plasmids from the first positive selection were transformed into *E. coli* Top10ΔserB harboring pCcdB. The cells were plated onto LB agar supplemented with 25 mg/ml Kan, 25 mg/ml Cm, and 0.1 mM IPTG. After 48 h incubation at 30° C., twenty individual clones were picked and subjected to plasmid purification to isolate pKD-SepRS-EFTu as described above. The EF-Tu mutant genes were digested from the plasmid and recloned into pKD-SepRS.

Resulting pKD-SepRS-EFTu plasmids were transformed into *E. coli* Top10ΔserB containing pCAT112-SepT for a third round of selection which was carried out under the same conditions as the first. This time, individual colonies were isolated from agar plates and clones were tested for their ability to grow on Cm over a concentration range from 5 to 100 mg/ml. Total plasmid was purified from isolates showing strong Cm resistance, and pKD-SepRS-EFTu plasmids were subjected to sequencing.

To confirm that the observed Cm resistance is dependent on the presence of both, mutant EF-Tu and SepRS, EF-Tu mutant genes were excised from their plasmids, recloned into pKD, and retransformed into *E. coli* Top10ΔserB containing pCAT112-SepT. Cells were then tested for Cm resistance as described above.

Expression and Purification of *M. maripaludis* SepRS and CysRS.

SepRS and CysRS were produced in *E. coli* and purified as described by Hohn, M. J. et al., *Proc Natl Acad Sci USA* 103, 18095 (2006).

Expression and Purification of EF-Tu and EF-Sep.

pMAL-EFTu or pMAL-EFSep were transformed into *E. coli* BL21 (DE3) codon plus (Stratagene). A pre-culture was used to inoculate 1000 ml of LB broth with 100 μg/ml of Amp, 34 μg/ml Cm, 5052 solution, and phosphate buffer for autoinduction as described by Studier, F W. *Protein Expr Purif* 41, 207 (2005). The cells were grown for 6 h at 37° C. and continued at 20° C. for 18 h.

The cells were pelleted and lysed by shaking for 20 min. in BugBuster (Novagen) reagent supplemented with 50 mM Tris-HCl (pH 7.6), 60 mM NH$_4$Cl, 7 mM MgCl$_2$, 14.3 mM 2-mercapto-ethanol, 50 M GDP, 10% glycerol, 25 U ml$^{-1}$ Benzoase, 1 mg ml$^{-1}$ lysozyme, and Protease inhibitor cocktail (Roche).

The extract was clarified by ultracentrifugation and applied to a Ni$^{2+}$-NTA resin (Qiagen) and purified according to the manufacturer's instructions.

The eluted enzymes were dialyzed into 20 mM Hepes-KOH (pH 7.0), 40 mM KCl, 1 mM MgCl$_2$, 5 mM DTT, 50 μM GDP, and 30% glycerol. SDS-PAGE electrophoresis followed by staining with Coomassie blue revealed greater than 95% purity.

Results

Guided by the structure of the *E. coli* EF-Tu:Phe-tRNAPhe complex (P. Nissen et al., *Science* 270, 1464 (1995)) it was decided to randomize certain positions in the amino acid binding pocket to evolve EF-Tu variants that bind Sep-tRNA and promote its delivery to the ribosome. Six residues (His67, Glu216, Asp217, Phe219, Thr229, and Asn274) were selected for complete randomization generating a library of 3×10$^8$ EF-Tu mutants. To select in vivo variants that permits Sep incorporation in the presence of SepRS and tRNA$^{Sep}$ three rounds of selections (positive, negative, positive) were performed that yielded several clones with the desired phenotype. One clone, designated EF-Sep, was tested further in detail. While the combination of SepRS and EF-Sep was not active in the CAT suppression assay (FIG. 2, lane G), the further inclusion of tRNA$^{Sep}$ led to a 10-fold increase in Cm resistance (FIG. 2, lane H). Thus, it appeared that EF-Sep could bind Sep-tRNA$^{Sep}$, a fact that was ascertained in the hydrolysis protection assay (FIG. 3). The DNA sequence of the EF-Sep gene revealed the nature of the mutations.

EF-Tu mutants (EF-Sep) that could bind Sep-tRNA include those having the following amino acid sequences:

```
                                   (EFSep-M6. SEQ ID NO: 1)
MSKEKFERTKPHVNVGTIGHVDHGKTTLTAAITTVLAKTYGG

TARAFDQIDNAPEEKARGITINTSRVEYDTPTRHYAHVDCPGHADYV

KNMITGAAQMDGAILVVAATDGPMPQTREHILLGRQVGVPYIIVFLN

KDNMVDDEELLELVEMEVRELLSQYDFPGDDTPIVRGSALKALEGD

AEWEAKILELAGFLDSYIPEPERAIDKPFLLPITRVYSISGRGTVVSGR

VERGIIKVGEEVEIVGIKETQKSTCTGVEMFRKLLDEGRAGEFVGLL

RGIKREEIERGQVLAKPGTIKPHTKFESEVYILSKDEGGRHTPFFKGYR

PQFYFRTTDVTGTIELPEGVEMVMPGDNIKMVVTLIHPIAMDDGLRF

AIREGGRTVGAGVVAKVLRDPNSSSVDKLAAALE (EFSep-M7, SEQ ID NO: 2)
MSKEKFERTKPHVNVGTIGHVDHGKTTLTAAITTVLAKTYGG

AARAFDQIDNAPEEKARGITINTSRVEYDTPTRHYAHVDCPGHADYV

KNMITGAAQMDGAILVVAATDGPMPQTREHILLGRQVGVPYIIVFLN

KCDMVDDEELLELVEMEVRELLSQYDFPGDDTPIVRGSALKALEGD

AEWEAKILELAGFLDSYIPEPARAIDKPFLLPITYVYSISGRGTVVSGR

VERGIIKVGEEVEIVGINETQKSTCTGVEMFRKLLDEGRAGEAVGVL

LRGIKREEIERGQVLAKPGTIKPHTKFESEVYILSKDEGGRHTPFFKGY

RPQFYFRTTDVTGTIELPEGVEMVMPGDNIKMVVTLIHPIAMDDGLR

FAIREGGRTVGAGVVAKVLRDPNSSSVDKLAAALE (EFSep-M8, SEQ ID NO: 3)
MSKEKFERTKPHVNVGTIGHVDHGKTTLTAAITTVLAKTYGG

AARAFDQIDNAPEEKARGITINTSRVEYDTPTRHYAHVDCPGHADYV

KNMITGAAQMDGAILVVAATDGPMPQTREHILLGRQVGVPYIIVFLN

KCDMVDDEELLELVEMEVRELLSQYDFPGDDTPIVRGSALKALEGD

AEWEAKILELAGFLDSYIPEPERAIDKPFLLPINGVYSISGRGTVVSGR

VERGIIKVGEEVEIVGIKETQKSTCTGVEMFRKLLDEGRAGEWVGVL

LRGIKREEIERGQVLAKPGTIKPHTKFESEVYILSKDEGGRHTPFFKGY

RPQFYFRTTDVTGTIELPEGVEMVMPGDNIKMVVTLIHPIAMDDGLR

FAIREGGRTVGAGVVAKVLRDPNSSSVDKLAAALE (EFSep-M9, SEQ ID NO: 4)
MSKEKFERTKPHVNVGTIGHVDHGKTTLTAAITTVLAKTYGG

AARAFDQIDNAPEEKARGITINTSRVEYDTPTRHYAHVDCPGHADYV

KNMITGAAQMDGAILVVAATDGPMPQTREHILLGRQVGVPYIIVFLN

KCDMVDDEELLELVEMELEVRELLSQYDFPGDDTPIVRGSALKALEGD

AEWEAKILELAGFLDSYIPEPERAIDKPFLLPITAVYSISGRGTVVSGR

VERGIIKVGEEVEIVGIKETQKSTCTGVEMFRKLLDEGRAGEAVGVL

LRGIKREEIERGQVLAKPGTIKPHTKFESEVYILSKDEGGRHTPFFKGY
```

RPQFYFRTTDVTGTIELPEGVEMVMPGDNIKMVVTLIHPIAMDDGLR
FAIREGGRTVGAGVVAKVLRDPNSSSVDKLAAALE

Nucleic acid encoding EF-Tu mutants (EFSep) that could bind Sep-tRNA include those having the following amino acid sequences:

(EFSep-M6, SEQ ID NO: 5)
ATGTCTAAAGAAAAGTTTGAACGTACAAAACCGCACGTTA

ACGTCGGTACTATCGGCCACGTTGACCATGGTAAAACAACGCTGA

CCGCTGCAATCACTACCGTACTGGCTAAAACCTACGGCGGTACTG

CTCGCGCATTCGACCAGATCGATAACGCGCCGGAAGAAAAAGCT

CGTGGTATCACCATCAACACTTCTCGGGTTGAATACGACACCCCG

ACCCGTCACTACGCACACGTAGACTGCCCGGGGCACGCCGACTAT

GTTAAAAACATGATCACCGGTGCTGCGCAGATGGACGGCGCGATC

CTGGTAGTTGCTGCGACTGACGGCCCGATGCCGCAGACTCGTGAG

CACATCCTGCTGGGTCGTCAGGTAGGCGTTCCGTACATCATCGTG

TTCCTGAACAAATGCGACATGGTTGATGACGAAGAGCTGCTGGAA

CTGGTTGAAATGGAAGTTCGTGAACTTCTGTCTCAGTACGACTTCC

CGGGCGACGACACTCCGATCGTTCGTGGTTCTGCTCTGAAAGCGC

TGGAAGGCGACGCAGAGTGGGAAGCGAAAATCCTGGAACTGGCT

GGCTTCCTGGATTCTTACATTCCGGAACCAGAGCGTGCGATTGAC

AAGCCGTTCCTGCTGCCGATCACCCGGGTATACTCCATCTCCGGT

CGTGGTACCGTTGTTTCGGGTCGTGTAGAACGCGGTATCATCAAA

GTTGGTGAAGAAGTTGAAATCGTTGGTATCAAAGAGACTCAGAA

GTCTACCTGTACTGGCGTTGAAATGTTCCGCAAACTGCTGGACGA

AGGCCGTGCTGGTGAGTTCGTAGGTGTTCTGCTGCGTGGTATCAA

ACGTGAAGAAATCGAACGTGGTCAGGTACTGGCTAAGCCGGGCA

CCATCAAGCCGCACACCAAGTTCGAATCTGAAGTGTACATTCTGT

CCAAAGATGAAGGCGGCCGTCATACTCCGTTCTTCAAAGGCTACC

GTCCGCAGTTCTACTTCCGTACTACTGACGTGACTGGTACCATCGA

ACTGCCGGAAGGCGTAGAGATGGTAATGCCGGGCGACAACATCA

AAATGGTTGTTACCCTGATCCACCCGATCGCGATGGACGACGGTC

TGCGTTTCGCAATCCGTGAAGGCGGCCGTACCGTTGGCGCGGGCG

TTGTAGCAAAAGTTCTGAGGGATCCGAATTCGAGCTCCGTCGACA

AGCTTGCGGCCGCACTCGAG (EFSep-M7, SEQ ID NO: 6)

ATGTCTAAAGAAAAGTTTGAACGTACAAAACCGCACGTTA

ACGTCGGTACTATCGGCCACGTTGACCATGGTAAAACAACGCTGA

CCGCTGCAATCACTACCGTACTGGCTAAAACCTACGGCGGTGCTG

CTCGCGCATTCGACCAGATCGATAACGCGCCGGAAGAAAAAGCT

CGTGGTATCACCATCAACACTTCTAGGGTTGAATACGACACCCCG

ACCCGTCACTACGCACACGTAGACTGCCCGGGGCACGCCGACTAT

-continued

GTTAAAAACATGATCACCGGTGCTGCGCAGATGGACGGCGCGATC

CTGGTAGTTGCTGCGACTGACGGCCCGATGCCGCAGACTCGTGAG

CACATCCTGCTGGGTCGTCAGGTAGGCGTTCCGTACATCATCGTG

TTCCTGAACAAATGCGACATGGTTGATGACGAAGAGCTGCTGGAA

CTGGTTGAAATGGAAGTTCGTGAACTTCTGTCTCAGTACGACTTCC

CGGGCGACGACACTCCGATCGTTCGTGGTTCTGCTCTGAAAGCGC

TGGAAGGCGACGCAGAGTGGGAAGCGAAAATCCTGGAACTGGCT

GGCTTCCTGGATTCTTACATTCCGGAACCAGAGCGTGCGATTGAC

AAGCCGTTCTGCTGCCGATCACCTACGTATACTCCATCTCCGGT

CGTGGTACCGTTGTTTCGGGTCGTGTAGAACGCGGTATCATCAAA

GTTGGTGAAGAAGTTGAAATCGTTGGTATCAATGAGACTCAGAAG

TCTACCTGTACTGGCGTTGAAATGTTCCGCAAACTGCTGGACGAA

GGCCGTGCTGGTGAGGCGGTAGGTGTTCTGCTGCGTGGTATCAAA

CGTGAAGAAATCGAACGTGGTCAGGTACTGGCTAAGCCGGGCAC

CATCAAGCCGCACACCAAGTTCGAATCTGAAGTGTACATTCTGTC

CAAAGATGAAGGCGGCCGTCATACTCCGTTCTTCAAAGGCTACCG

TCCGCAGTTCTACTTCCGTACTACTGACGTGACTGGTACCATCGAA

CTGCCGGAAGGCGTAGAGATGGTAATGCCGGGCGACAACATCAA

AATGGTTGTTACCCTGATCCACCCGATCGCGATGGACGACGGTCT

GCGTTTCGCAATCCGTGAAGGCGGCCGTACCGTTGGCGCGGGCGT

TGTAGCAAAAGTTCTGAGGGATCCGAATTCGAGCTCCGTCGACAA

GCTTGCGGCCGCACTCGAG (EFSep-M8, SEQ ID NO: 7)

ATGTCTAAAGAAAAGTTTGAACGTACAAAACCGCACGTTA

ACGTCGGTACTATCGGCCACGTTGACCATGGTAAAACAACGCTGA

CCGCTGCAATCACTACCGTACTGGCTAAAACCTACGGCGGTGCTG

CTCGCGCATTCGACCAGATCGATAACGCGCCGGAAGAAAAAGCT

CGTGGTATCACCATCAACACTTCTCGGGTTGAATACGACACCCCG

ACCCGTCACTACGCACACGTAGACTGCCCGGGGCACGCCGACTAT

GTTAAAAACATGATCACCGGTGCTGCGCAGATGGACGGCGCGATC

CTGGTAGTTGCTGCGACTGACGGCCCGATGCCGCAGACTCGTGAG

CACATCCTGCTGGGTCGTCAGGTAGGCGTTCCGTACATCATCGTG

TTCCTGAACAAATGCGACATGGTTGATGACGAAGAGCTGCTGGAA

CTGGTTGAAATGGAAGTTCGTGAAACTTCTGTCTCAGTACGACTTCC

CGGGCGACGACACTCCGATCGTTCGTGGTTCTGCTCTGAAAGCGC

TGGAAGGCGACGCAGAGTGGGAAGCGAAAATCCTGGAACTGGCT

GGCTTCCTGGATTCTTACATTCCGGAACCAGAGCGTGCGATTGAC

AAGCCGTTCCTGCTGCCGATCAACGGGGTATACTCCATCTCCGGT

CGTGGTACCGTTGTTTCGGGTCGTGTAGAACGCGGTATCATCAAA

GTTGGTGAAGAAGTTGAAATCGTTGGTATCAAAGAGACTCAGAA

GTCTACCTGTACTGGCGTTGAAATGTTCCGCAAACTGCTGGACGA

```
                                                          -continued
AGGCCGTGCTGGTGAGTGGGTAGGTGTTCTGCTGCGTGGTATCAA

ACGTGAAGAAATCGAACGTGGTCAGGTACTGGCTAAGCCGGGCA

CCATCAAGCCGCACACCAAGTTCGAATCTGAAGTGTACATTCTGT

CCAAAGATGAAGGCGGCCGTCATACTCCGTTCTTCAAAGGCTACC

GTCCGCAGTTCTACTTCCGTACTACTGACGTGACTGGTACCATCGA

ACTGCCGGAAGGCGTAGAGATGGTAATGCCGGGCGACAACATCA

AAATGGTTGTTACCCTGATCCACCCGATCGCGATGGACGACGGTC

TGCGTTTCGCAATCCGTGAAGGCGGCCGTACCGTTGGCGCGGGCG

TTGTAGCAAAAGTTCTGAGGGATCCGAATTCGAGCTCCGTCGACA

AGCTTGCGGCCGCACTCGAG (EFSep-M9, SEQ ID NO: 8)
ATGTCTAAAGAAAAGTTTGAACGTACAAAACCGCACGTTA

ACGTCGGTACTATCGGCCACGTTGACCATGGTAAAACAACGCTGA

CCGCTGCAATCACTACCGTACTGGCTAAAACCTACGGCGGTGCTG

CTCGCGCATTCGACCAGATCGATAACGCGCCGGAAGAAAAAGCT

CGTGGTATCACCATCAACACTTCTCGGGTTGAATACGACACCCCG

ACCCGTCACTACGCACACGTAGACTGCCCGGGGCACGCCGACTAT

GTTAAAAACATGATCACCGGTGCTGCGCAGATGGACGGCGCGATC

CTGGTAGTTGCTGCGACTGACGGCCCGATGCCGCAGACTCGTGAG

CACATCCTGCTGGGTCGTCAGGTAGGCGTTCCGTACATCATCGTG

TTCCTGAACAAATGCGACATGGTTGATGACGAAGAGCTGCTGGAA

CTGGTTGAAATGGAAGTTCGTGAACTTCTGTCTCAGTACGACTTCC

CGGGCGACGACACTCCGATCGTTCGTGGTTCTGCTCTGAAAGCGC

TGGAAGGCGACGCAGAGTGGGAAGCGAAAATCCTGGAACTGGCT

GGCTTCCTGGATTCTTACATTCCGGAACCAGAGCGTGCGATTGAC

AAGCCGTTCCTGCTGCCGATCACCGCGGTATACTCCATCTCCGGT

CGTGGTACCGTTGTTTCGGGTCGTGTAGAACGCGGTATCATCAAA

GTTGGTGAAGAAGTTGAAATCGTTGGTATCAAAGAGACTCAGAA

GTCTACCTGTACTGGCGTTGAAATGTTCCGCAAACTGCTGGACGA

AGGCCGTGCTGGTGAGGCCGTAGGTGTTCTGCTGCGTGGTATCAA

ACGTGAAGAAATCGAACGTGGTCAGGTACTGGCTAAGCCGGGCA

CCATCAAGCCGCACACCAAGTTCGAATCTGAAGTGTACATTCTGT

CCAAAGATGAAGGCGGCCGTCATACTCCGTTCTTCAAAGGCTACC

GTCCGCAGTTCTACTTCCGTACTACTGACGTGACTGGTACCATCGA

ACTGCCGGAAGGCGTAGAGATGGTAATGCCGGGCGACAACATCA

AAATGGTTGTTACCCTGATCCACCCGATCGCGATGGACGACGGTC

TGCGTTTCGCAATCCGTGAAGGCGGCCGTACCGTTGGCGCGGGCG

TTGTAGCAAAAGTTCTGAGGGATCCGAATTCGAGCTCCGTCGACA

AGCTTGCGGCCGCACTCGAG
```

Example 3

Demonstration of Sep Incorporation into Myoglobin

Materials and Methods
Construction of Plasmids pMYO127TAG-SepT was constructed by cloning a codon-optimized and C-terminally $His_6$-tagged sperm whale myoglobin gene under the control of the lpp promoter between NotI and BglII in pSepT. An amber stop codon was introduced to the myoglobin gene at position Asp127 by quickchange mutagenesis. The nucleotide sequence of the codon-optimized myoglobin gene is as follows:

```
                                             (SEQ ID NO: 44)
ATGGTTCTGTCTGAAGGTGAATGGCAGCTGGTTCTGCACGT

TTGGGCTAAAGTTGAAGCTGACGTTGCTGGTCACGGTCAGGACAT

CCTGATCCGTCTGTTCAAATCTCACCCGGAAACCCTGGAAAAATT

CGACCGTTTCAAACACCTGAAAACCGAAGCTGAAATGAAGGCTTC

TGAAGACCTGAAAAAACACGGTGTTACCGTTCTGACCGCTCTGGG

TGCTATCCTGAAGAAAAAGGGTCACCACGAAGCTGAACTGAAAC

CGCTGGCTCAGTCTCACGCTACCAAACACAAAATCCCGATCAAAT

ACCTGGAGTTCATCTCTGAAGCTATCATCCACGTTCTGCACTCTCG

TCATCCGGGTAACTTCGGTGCTGACGCTCAGGGTGCTATGAACAA

AGCTCTGGAACTGTTCCGTAAAGACATCGCTGCTAAATACAAAGA

ACTGGGTTACCAGGGTGGTTCTGGTCATCACCATCACCATCACTA

A.
```

Results

To prove that the observed suppression is due to Sep incorporation a myoglobin variant with an amber codon in position 127 (normally Asp) and a C-terminal $His_6$-tag was expressed. The expected full length protein was synthesized (yield is 2 mg/L of culture) only when EF-Sep, SepRS and tRNA$^{Sep}$ were co-expressed. The amino acid incorporated via EF-Sep in response to the amber codon was identified by analyzing both the intact and trypsin-digested Myo-His$_6$ mutant protein. MS-TOF and MS/MS analysis show that Sep is present at the position specified by UAG.

Example 4

Active MEK Synthesis In Vivo

Materials and Methods
Construction of Plasmids pET15-ERK2 encodes N-terminally His$_6$-tagged mitogen-activated protein kinase (Erk2) under the control of a T7 promoter. The human Erk2 gene was PCR amplified from plasmid BC017832 (ATCC) using primers ERK2-F (5'-GGA ATT CCA TAT GGC GGC GGC GGC GGC G-3', SEQ ID NO:27) and ERK2-R (5'-CCG CTC GAG TTA AGA TCT GTA TCC TGG-3', SEQ ID NO:28). The PCR product was cloned between NdeI and XhoI in vector pET15b (Novagen).

pET20-MBPMEK1 encodes a fusion protein consisting of human MEK1 with an N-terminal maltose binding protein (MBP) tag and a C-terminal His$_6$-tag. The gene encoding human MEK1 which was codon-optimized for *E. coli* and custom-synthesized in vitro (Genscript), was cloned between EcoRI and PstI into pMALc2x (New England Biolabs). The resulting MBP-MEK1 fusion construct was then amplified with primers ET20MEKF (5'-AAG GAA ATT AAT GAA AAT CGA AGA AGG TAA-3', SEQ ID NO:29) and ET20MEKR (5'-CTA GAG GAT CCG GCG CGC-3', SEQ ID NO:30) adding AseI and BamHI restriction sites, and the PCR product was ligated between NdeI and BamHI into pET20b.

Nucleotide Sequence of Codon-Optimized MEK:

```
                                    (SEQ ID NO: 31)
ATGCCGAAGAAGAAACCGACCCCGATCCAGCTGAACCCGG

CTCCGGACGGTTCTGCTGTTAACGGCACCTCTTCTGCTGAAACCA

ACCTGGAAGCTCTGCAAAAGAAACTGGAAGAACTGGAACTGGAC

GAACAGCAGCGTAAACGTCTGGAAGCGTTCCTGACCCAGAAACA

GAAAGTTGGTGAACTGAAAGACGACGACTTCGAAAAAATCTCTG

AACTGGGTGCTGGTAACGGTGGTGTTGTTTTCAAAGTTTCTCACA

AACCGTCCGGTCTGGTTATGGCTCGTAAACTGATCCACCTGGAAA

TCAAACCGGCTATCCGTAACCAGATCATCCGTGAACTGCAAGTTC

TGCACGAATGCAACTCTCCGTACATCGTTGGTTTCTACGGTGCTTT

CTACTCTGACGGTGAAATCTCTATCTGCATGGAACACATGGACGG

TGGTTCTCTGGACCAGGTTCTGAAAAAAGCTGGTCGTATCCCGGA

ACAGATCCTGGGTAAAGTTTCTATCGCTGTTATCAAAGGTCTGAC

CTACCTGCGTGAAAAACACAAAATCATGCACCGTGACGTTAAACC

GTCTAACATCCTGGTTAACTCTCGTGGTGAAATCAAACTGTGCGA

CTTCGGTGTTTCTGGTCAGCTGATCGACTCTATGGCTAACTCTTTC

GTTGGCACCCGTTCTTACATGTCTCCGGAACGTCTGCAAGGCACC

CACTACTCTGTTCAGTCTGACATCTGGTCTATGGGTCTGTCTCTGG

TTGAAATGGCTGTTGGTCGTTACCCGATCCCGCCGCCGGACGCTA

AAGAACTGGAACTGATGTTCGGTTGCCAGGTTGAAGGTGACGCTG

CTGAAACCCCGCCGCGTCCGCGTACTCCGGGTCGTCCGCTGTCTTC

TTACGGTATGGACTCTGTCCGCCGATGGCTATCTTCGAACTGCTG

GACTACATCGTTAACGAACCGCCGCCGAAACTGCCGTCTGGTGTT

TTCTCTCTGGAGTTCCAGGACTTCGTTAACAAATGCCTGATCAAA

AACCCGGCTGAACGTGCTGACCTGAAACAGCTGATGGTTCACGCT

TTCATCAAACGTTCTGACGCTGAAGAAGTTGACTTCGCTGGTTGG

CTGTGCTCTACCATCGGTCTGAACCAGCCGTCTACCCCGACCCAC

GCTGCTGGTGTGGCAGCCGCAGCTGCGCATCATCACCACCATCAC

TAA.
``` pCG-MBPMEK1SS was generated by the ligation of three PCR products. One PCR product was derived from pGFIB (Normanly J, et al. *Nature* 321:213 (1986)) using primers GFIB-F (5'-ATA AGA ATG CGG CCG CGC CGC AGC CGA ACG ACC GAG-3', SEQ ID NO:32) and GFIB-R (5'-CTA GCT AGC GCT TCA GTG GAA CG-3', SEQ ID NO:33). The second PCR product was generated from pCDFDuet-1 (Novagen) using primers CDF-F (5'-CTA GCT AGC TCA CTC GGT CGC TAC GCT-3', SEQ ID NO:34) and CDF-R (5'-ATA AGA ATG CGG CCG CTG AAA TCT AGA GCG GTT CAG-3', SEQ ID NO:35). Both PCR products were digested with NheI and NotI and ligated to form plasmid pCG. The third PCR product, encoding an expression cassette for MBP-MEK1-His$_6$ under the control of T7 promoter and T7 terminator, was generated from pET20-MBPMEK1 using primers ETCDGFF (5'-AAA AGG CGC CGC CAG CCT AGC CGG GTC CTC AAC G-3', SEQ ID NO:36) and ETCDGFR (5'-AAC TGC AGC CAA TCC GGA TAT AGT TC-3', SEQ ID NO:37). This PCR product was cloned between the NarI and PstI sites of pCG.

The codon for Ser 222 in MEK1 was then replaced by a GAA codon (encoding Glu) using Quickchange mutagenesis (Stratagene). In the same way, codon Ser 218 was either changed to GAA to generate pCG-MBPMEK1EE, or to an amber stop codon, resulting in pCG-MBPMEK1XE. In pCG-MBPMEK1XS only the codon for Ser218 was changed to UAG and in pCG-MBPMEK1XX both codons for Ser218 and Ser222 were changed to amber.

Expression and Purification of Myoglobin

To express mutant myoglobin, pKD-SepRS-EF-Sep and pKD-SepRS were transformed into *E. coli* Top10ΔserB containing pMYO127TAG-SepT. *E. coli* Top10ΔserB with pMYO, encoding the wild type myoglobin gene was used as a control. Cultures were grown in LB medium supplemented with 2 mM Sep. When $A_{600}$ reached 0.6 protein expression was induced with 0.05 mM IPTG for 12 h at 25° C. The cells were harvested, resuspended in lysis buffer (50 mM Tris-HCl (pH 7.8), 300 mM NaCl, 14.3 mM 2-mercaptoethanol) supplemented with protease inhibitor cocktail (Roche), and subjected to sonication. The lysate was centrifuged at 10,000×g for 30 min and the supernatant was applied to Ni$^{2+}$-NTA agarose (Qiagen) purification according to the manufacturer's instruction.

Expression and Purification of MEK1

To express MEK1 (as a maltose binding protein fusion-protein) *E. coli* BL21ΔserB was transformed with plasmids pKD-SepRS-EFSep, pCAT112TAG-SepT, and pCG-MBPMEK1SS, pCG-MBPMEK1EE, pCG-MBPMEK1XE, pCG-MBPMEK1XS, or pCG-MBPMEK1XX, respectively. Plasmid pCAT112TAG-SepT was replaced by pL11C-SepT in the strain used to produce MBP-MEK1(Sep218,Ser222)-His$_6$ for mass spectrometry analysis.

Cells were grown at 30° C. in 1 liter of LB supplemented with 100 µg/ml of Amp, 50 µg/ml Kan, 12 µg/ml Tc, 2 mM Sep, 5052 solution, and phosphate buffer for autoinduction. When A600 reached 0.6, temperature was changed to 16° C. and incubation continued for 18 h. After harvesting, cells were lysed in 20 ml BugBuster reagent containing 50 mM Tris-HCl (pH 7.8), 500 mM NaCl, 0.5 mM EGTA, 0.5 mM EDTA, 14.3 mM 2-mercapto-ethanol, 10% glycerol, 0.03% Brij-35, protease inhibitors, 25 U ml$^{-1}$ Benzoase, and 1 mg ml$^{-1}$ lysozyme. The lysate was clarified by ultracentrifugation, and applied to a 0.4 ml Ni$^{2+}$-NTA agarose column. The column was washed with 15 ml wash buffer (50 mM Tris-HCl (pH 7.8), 150 mM NaCl, 0.5 mM EGTA, 0.5 mM EDTA, 14.3 mM 2-mercaptoethanol, 10% glycerol, 0.03% Brij-35, and 20 mM imidazole). Proteins were eluted in 0.8 ml of wash buffer supplemented with 300 mM imidazole, dialyzed against 50 mM Tris-HCl (pH 7.8), 150 mM NaCl, 0.1 mM EGTA, 5 mM DTT, 30% glycerol, and 0.03% Brij-35, and stored at −20° C. Purified proteins were analyzed by SDS-PAGE.

Expression and Purification of Erk2

*E. coli* BL21 (DE3) codon plus cells were transformed with pET15-ERK2 and grown at 37° C. in 1 liter LB broth supplemented with 100 g/ml Amp and 34 g/ml Cm. When the cultures reached A600 of 0.6, 0.2 mM IPTG was added and expression was induced for 19 h at 16° C.

Cell lysis, $Ni^{2+}$ purification, and dialysis of Erk2 were carried out as described for MEK1. Erk2 was 99% pure, as judged by Coomassie brilliant blue staining after SDS-PAGE.

Preparation and Aminoacylation of tRNA

Total tRNA from *E. coli* Top10 or from *E. coli* Top10 complemented with pCysT or pSepT, respectively, was purified by standard procedures and acylated with [$^{14}$C]Sep by *M. maripaludis* SepRS as described previously. In vivo synthesized tRNA was for this experiment to ensure that nucleoside modifications introduced into tRNA by *E. coli* modifying enzymes do not affect tRNA recognition by SepRS. *M. jannaschii* tRNA$^{Cys}$ contains m$^1$G37 when isolated from *M. jannaschii*. Since the *E. coli* methylase TrmD is known to methylate G37 of archaeal tRNA$^{Pro}$, it is believed that the in vivo expressed tRNA$^{Sep}$ also carries the m$^1$G37 modification. In vitro transcript of *M. jannaschii* tRNA$^{Cys}$ was prepared and acylated with [$^{14}$C]Sep or [$^{35}$S]Cys using recombinant *M. maripaludis* SepRS or CysRS. *M. jannaschii* tRNA$^{Cys}$ transcript was chosen for these experiments because of the poor folding properties of in vitro transcribed *M. maripaludis* tRNA$^{Cys}$ (Hohn, M. J. *Proc Natl Acad Sci USA* 103, 18095 (2006)).

EF-Tu Hydrolysis Protection Assays

To assay hydrolysis protection of acylated tRNA$^{Cys}$ by EF-Tu, Mmp tRNA$^{Cys}$ in vitro transcripts acylated with [$^{14}$C]Sep or [$^{35}$S]Cys, respectively, were phenol/chlorophorm extracted, and the aqueous phase was passed over Sephadex® G25 Microspin columns (GE Healthcare) equilibrated with water. Protection of aminoacylated tRNA by EF-Tu was assayed as described earlier with slight modifications (Ling J. et al., *Proc Natl Acad Sci USA* 104, 15299 (2007)). Briefly, EF-Tu or EF-Sep (both purified as maltose binding protein fusion proteins) were activated for 20 min. at 37° C. in buffer containing 100 mM Tris-HCl (pH 8.2), 120 mM NH$_4$Cl, 7 mM MgCl$_2$, 5 mM DTT, 5 mM phosphoenolpyruvate, 1.5 mM GTP, and 0.12 µg/µl pyruvate kinase. Hydrolysis of 2 M [$^{14}$C]Sep-tRNA$^{Cys}$ was then monitored at 25° C. in the presence of 40 M EF-Tu (wt), EF-Sep, or BSA, respectively. Aliquots were taken from the reaction mix at indicated time points and spotted on 3MM filter discs presoaked with 10% trichloroacetic acid. Filters were washed with 5% trichloroacetic acid, dried, and radioactivity was measured by liquid scintillation counting.

MEK Activity Assays

Recombinant MEK1 variants were assayed (as maltose binding protein (MBP) fusion-proteins). Briefly, in a first reaction, various amounts (2.5-5000 ng) of recombinant MBP-MEK1 variants were used to phosphorylate (and activate) bacterially expressed MAP kinase (Erk2) for 15 min. at 30° C. in 35 µl kinase assay buffer containing 12 mM MOPS pH 7.2, 20 mM MgCl$_2$, 3 mM EGTA, 15 mM β-glycerol phosphate, 0.6 mM DTT, 140 M ATP, and 1 g Erk2.

After 15 min, a 5 µl aliquot was transferred to a second reaction in which activated Erk2 phosphorylates myelin basic protein (MBP; 570 g ml$^{-1}$) in kinase assay buffer in the presence of [γ-$^{32}$P]ATP. After 15 min. incubation at 30° C. 25 µl aliquots were transferred onto p81 phosphocellulose filters (Whatman). The filters were washed three times with 180 mM phosphoric acid and then rinsed with acetone. Phosphorylation was quantitated by scintillation counting and the specific activity of MEK1 was calculated from the amount of [$^{32}$P]phosphate incorporated into MBP.

LC and MS/MS Conditions for Multiple Reaction Monitoring (MRM)

Purified MEK1 proteins were separated by SDS-PAGE, visualized with Comassie stain, excised, washed in 50% acetonitrile (ACN)/50 mM NH$_4$HCO$_3$, crushed, and digested at 37° C. in a 20 µg/ml trypsin (Promega) solution in 10 mM NH$_4$HCO$_3$. Digested peptides in solution were dried and dissolved in 3 µl of 70% formic acid (FA), and then diluted to 10 µl with 0.1% TFA. Peptides for MRM were synthesized at the KECK peptide synthesis facility at Yale. The human MEK peptide LCDFGVSGQLIDS*MANSFVGTR (SEQ ID NO:40) (*phospho-Ser; YPED peptide ID, SOL14075) was synthesized to permit the development of a specific method for quantitative MRM. Crude synthetic peptides were direct infused at a concentration of ~10 pmol/µl and Collision Energy and Declustering Potentials of the transitions were optimized. LC-MRM was performed on an ABI 5500 QTRAP triple quadrupole mass spectrometer inter-faced with a Waters nanoAcquity UPLC system running Analyst 1.5 software. Peptides were resolved for MRM (LC step) by loading 4 µl of sample onto a Symmetry C18 nanoAcquity trapping column (180 µm×20 mm 5 µm) with 100% water at 15 µl per minute for 1 minute. After trapping, peptides were resolved on a BEH130 C18 nanoAcquity column (75 µm×50 mm 1.7 µm) with a 30 minute, 2-40% ACN/0.1% FA linear gradient (0.5 µl/min flow rate). MRM scanning was carried out with 18 transitions and a cycle time of 1.44 seconds with a 40 millisecond dwell time per transition. An MRM Initiated Detection and Sequencing (MIDAS) was performed. The IDA method consisted of the most intense peak using rolling collision energy. The target ions were excluded after 3 occurrences for 30 seconds. The EPI scan had a scan rate of 20,000 Da/sec with a sum of 3 scans and mass range of 100-1000 Da and a cycle time of 1.4 msec. Files were searched using Mascot version 2.3 with the Swissprot database (08/2010) selected (human taxonomic restriction). Phosphorylated S and T, and propionamide C were variable modifications. Peptide and fragment mass tolerance is 0.6 Da, with 1 missed cleavage. Quantification was performed using MultiQuant 2.0.

Results

To further demonstrate the usefulness of the disclosed strategy for the synthesis of a protein that is naturally phosphorylated at a serine residue, recombinant, Sep containing mitogen-activated ERK activating kinase 1 (MEK1) was produced. This key enzyme of the mitogen-activated signaling cascade in eukaryotic cells plays crucial roles in cell proliferation, cell development and differentiation, cell cycle control and oncogenesis (Sebolt-Leopold, J. S., et al. *Nat Rev Cancer* 4, 937 (2004)). Activation of MEK1 requires post-translational phosphorylation of Ser218 and Ser222 by MEK activating kinases (e.g., Raf-1, MEKK, or MOS). Change of both Ser residues to Glu yields a constitutively active enzyme albeit with lower activity (Alessi D R. et al., *EMBO J* 13, 1610 (1994)).

Figure 4:
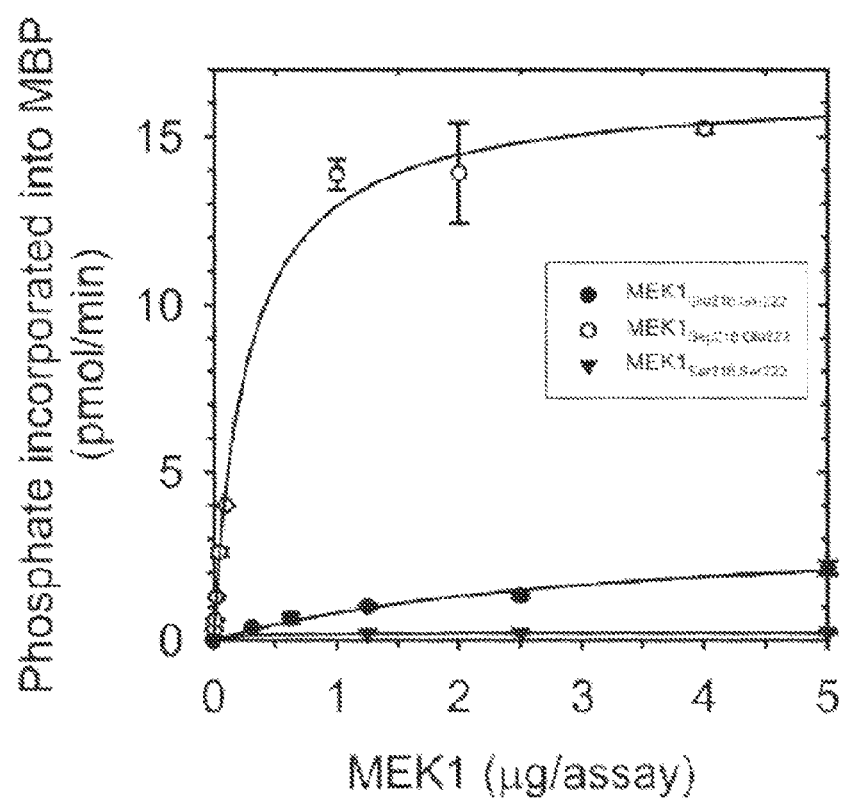
FIG. 4 is a graph showing kinase activity (phosphate incorporation into MyBP (pmol/min)) as a function of MEK1 concentration (μg/assay) for wild type (triangle) and mutant (closed and open circles) MEK1. Human MEK1 was produced as a maltose-binding protein (MBP) fusion-protein in *E. coli*. Residues Ser218 and Ser222, which are targets of phosphorylation by MEK1 activators were either mutated to Glu218/Glu222 (closed circle) or to Sep218/Glu222 (open circle) to produce active MEK1 variants. Various amounts of MBP-MEK1 were used to phosphorylate inactive ERK2 in vitro. ERK2 activity was then measured in a radiometric assay using [$^{32}$P]-γATP and myelin basic protein as substrates.

To improve expression of this human protein in the *E. coli* BL21 ΔserB strain and to allow purification by $Ni^{2+}$-affinity chromatography a MEK1 clone was designed to generate an N-terminal fusion with maltose binding protein (MBP) and with a C-terminal His$_6$-tag. Position 222 was changed to Glu and the codon for Ser218 was replaced by UAG to encode Sep. After expression in the presence of SepRS, tRNA$^{Sep}$ and EF-Sep 25 µg of full-length MBP-MEK1(Sep218, Glu222) were isolated from 1 L of culture. The presence of Sep in this recombinant MEK1-fusion protein was demonstrated by its activity in phosphorylating ERK2. The assay requires the additional component, myelin basic protein (MyBP) which will be phosphorylated by activated ERK2 in the presence of [γ-$^{32}$P]ATP; the amount of [$^{32}$P]MyBP relates to the specific activity of MEK1. As FIG. 4 shows, MBP-MEK1(Sep218,Glu222) had a 2,500-fold higher specific activity than non-phosphorylated MBP-MEK1(Ser218, Ser222), and a 70-fold higher specific activity than the constitutively active MBP-MEK1(Glu218,Glu222) mutant (FIG. 4).

To demonstrate the incorporation of Sep at position 218 an assay was developed utilizing multiple reaction monitoring (MRM) and a triple-quadrupole mass spectrometer. The MRM assay was designed to detect an intact tryptic phosphopeptide ion (m/z 823.4$^{+3}$) derived from MBP-MEK1 (Sep218,Ser222) and 4 fragment ions produced by collision-induced dissociation of this intact phosphopeptide (Table 1). The MRM method included an Information Dependent Acquisition (IDA) step that triggered a full MS/MS scan once the 823.4$^{+3}$ ion, and associated fragment ions, were detected. The IDA MS/MS spectrum confirmed the incorporation of Sep at position 218 and Ser at 222 in MBP-MEK1 (Sep218, Ser222).

TABLE 1

Peptide information for MRM

| Peptide(SEQ ID NO: 40) | precursor/production | CE | DP |
|---|---|---|---|
| LC*DFGVSGQLIDS$^P$MANSFVGTR | 823.4$^{(3+)}$/ 333.2$^{(1+)}$[y3] | 30.85 | 160.9 |
| LC*DFGVSGQLIDS$^P$MANSFVGTR | 823.4$^{(3+)}$/ 666.35$^{(1+)}$[y6] | 38.26 | 160.9 |
| LC*DFGVSGQLIDS$^P$MANSFVGTR | 823.4$^{(3+)}$/ 780.4$^{(1+)}$[y7] | 38.62 | 160.9 |
| LC*DFGVSGQLIDS$^P$MANSFVGTR | 823.4$^{(3+)}$/ 851.4$^{(1+)}$[y8] | 38.12 | 160.9 |

S$^P$, phosphoserine; C*, propionamide; CE, Collision energy; DP, Dilution Potential To determine if our *E. coli* expression system would allow the simultaneous insertion of two Sep residues into the protein, the Ser codons in positions 218 and 222 were changed to UAG. As expected the expression efficiency of MBP-MEK1(Sep218,Sep222) was dramatically reduced compared to wild-type MBP-MEK1 (only about 1 μg of full length protein was obtained from 1 L culture). The presence of Sep at both active site positions of MEK1 was tested by Western blot analysis using a monoclonal antibody specific to the phosphorylated active site of human MEK2. Only recombinant MBP-MEK1(Sep218,Sep222), and to a weaker extent MBP-MEK1(Sep218,Ser222) was detected in this experiment, while neither MBP-MEK1(Ser218,Ser222), MBP-MEK(Sep218,Glu222) or MBP-MEK(Glu218, Glu222) was recognized by this antibody. The presence of full-length MBP-fusion proteins was confirmed by Coomassie staining and by Western hybridization with an MBP-specific antibody. This demonstrates that the addition of SepRS, tRNA$^{Sep}$ and EF-Sep endows *E. coli* with the ability to read UAG as a phosphoserine codon.

Unless defined otherwise, all technical and scientific terms used herein have the same meanings as commonly understood by one of skill in the art to which the disclosed invention belongs.

We claim:

1. A method for site specific incorporation of phosphoserine into a target protein, comprising expressing a messenger RNA (mRNA) encoding the target protein in a system comprising:
   - an O-phosphoseryl-tRNA synthetase (SepRS) that aminoacylates a tRNA (tRNA$^{Sep}$) with phosphoserine;
   - a tRNA$^{Sep}$ that can be aminoacylated with phosphoserine by SepRS to form a Sep-tRNA$^{Sep}$ and recognize at least one codon in the mRNA encoding the target protein; and
   - an elongation factor (EF-Sep) comprising:
     (i) an amino acid sequence at least 90% identical to SEQ ID NO: 1, SEQ ID NO:2, SEQ ID NO:3, or SEQ ID NO:4, wherein the amino acid sequence comprises the amino acids of SEQ ID NO: 1, SEQ ID NO:2, SEQ ID NO:3, or SEQ ID NO:4 at positions corresponding to amino acid number 67, 217, 219, 229, and 274 of SEQ ID NO: 1, SEQ ID NO:2, SEQ ID NO:3, or SEQ ID NO:4, and a substitution mutation corresponding to amino acid number 216 of SEQ ID NO: 1, SEQ ID NO:2, SEQ ID NO:3, or SEQ ID NO:4; or
     (ii) an amino acid binding pocket for aminoacylated tRNA,
   wherein the binding pocket comprises the binding pocket for aminoacylated tRNA of SEQ ID NO:3 with an asparagine-to-valine substitution at amino acid residue 216 (N216V) of SEQ ID NO:3;
   wherein the EF-Sep that binds the Sep-tRNA$^{Sep}$ and catalyzes the covalent transfer of the phosphoserine amino acid of the Sep-tRNA$^{Sep}$ onto a polypeptide;
   wherein the SepRS aminoacylates tRNA$^{Sep}$ with phosphoserine and the tRNA$^{Sep}$ recognizes at least one codon such that phosphoserine is incorporated into a protein or polypeptide, and
   wherein the EF-Sep binds and protects Sep-tRNA$^{Sep}$ from deacylation.

2. The method of claim 1, wherein the EF-Sep comprises an amino acid sequence at least 90% identical to SEQ ID NO: 1, SEQ ID NO:2, SEQ ID NO:3, or SEQ ID NO:4, wherein the amino acid sequence comprises the amino acids of SEQ ID NO: 1, SEQ ID NO:2, SEQ ID NO:3, or SEQ ID NO:4 at positions corresponding to amino acid number 67, 217, 219, 229, and 274 of SEQ ID NO: 1, SEQ ID NO:2, SEQ ID NO:3, or SEQ ID NO:4, and a substitution mutation corresponding to amino acid number 216 of SEQ ID NO: 1, SEQ ID NO:2, SEQ ID NO:3, or SEQ ID NO:4.

3. The method of claim 1, wherein the system comprises a polynucleotide encoding the EF-Sep.

4. The method of claim 1, wherein the tRNA$^{Sep}$ is cysteinyl-tRNA from *Methanocaldococcus jannaschii*.

5. The method of claim 4, wherein the tRNA$^{Sep}$ is encoded by the nucleic acid sequence of SEQ ID NO:41.

6. The method of claim 1, wherein the SepRS is the phosphoseryl-tRNA synthetase from *Methanococcus maripaludis* or *Methanocaldococcus jannaschii*.

7. The method of claim 6, wherein the SepRS comprises the amino acid sequence SEQ ID NO:43 or 46.

8. The method of claim 7, wherein the system comprises a polynucleotide encoding SepRS comprising the nucleic acid sequence of SEQ ID NO:42 or 45.

9. The method of claim 1, wherein the SepRS, the EF-Sep, the tRNA$^{sep}$, or a combination thereof are expressed by a nucleic acid on one or more vectors or integrated into an organism's genome.

10. The method of claim 9, wherein the vector is an expression vector selected from the group consisting of a plasmid, a virus, a naked polynucleotide, and a conjugated polynucleotide.

11. The method of claim 9, wherein the vector is expressed in cells selected from the group consisting of bacterial cells, archeaebacterial cells, and eukaryotic cells.

12. The method of claim 9, wherein the vector is expressed in an in vitro transcription/translation system.

13. The method of claim 12, wherein the vector is transcribed and translated prior to or along with nucleic acids encoding one or more proteins or polypeptides.

14. The method of claim 1, wherein the nucleic acids are expressed in an organism.

15. The method of claim 1, wherein the nucleic acids are under control of a promoter selected from the group consisting of constitutive, inducible and tissue-specific.

16. An elongation factor (EF-Sep) comprising an amino acid sequence at least 90% identical to SEQ ID NO: 1, SEQ ID NO:2, SEQ ID NO:3, or SEQ ID NO:4, wherein the amino acid sequence comprises the amino acids of SEQ ID NO: 1, SEQ ID NO:2, SEQ ID NO:3, or SEQ ID NO:4 at positions corresponding to amino acid number 67, 217, 219, 229, and 274 of SEQ ID NO: 1, SEQ ID NO:2, SEQ ID NO:3, or SEQ ID NO:4,
   a substitution mutation corresponding to amino acid number 216 of SEQ ID NO: 1, SEQ ID NO:2, SEQ ID NO:3, or SEQ ID NO:4, and
   wherein the EF-Sep can bind to a Sep-tRNA$^{Sep}$ and can catalyze the covalent transfer of the phosphoserine amino acid of the Sep-tRNA$^{Sep}$ onto a polypeptide.

17. The EF-Sep of claim 16, comprising an amino acid sequence at least 90% identical to SEQ ID NO:3, wherein the amino acid sequence comprises the amino acids of SEQ ID NO:3 at positions corresponding to amino acid number 67, 217, 219, 229, and 274 of SEQ ID NO: 1, SEQ ID NO:2, SEQ ID NO:3, or SEQ ID NO:4, and
   wherein amino acid number 216 is valine.

18. An EF-Sep comprising an amino acid binding pocket for aminoacylated tRNA,
   wherein the binding pocket comprises the binding pocket for aminoacylated tRNA of SEQ ID NO:3 with an asparagine-to-valine substitution at amino acid residue 216 (N216V) of SEQ ID NO:3, and
   wherein the EF-Sep can bind to a Sep-tRNA$^{Sep}$ and can catalyze the covalent transfer of the phosphoserine amino acid of the Sep-tRNA$^{Sep}$ onto a polypeptide.

* * * * *